(12) United States Patent
Dekel et al.

(10) Patent No.: US 11,684,477 B2
(45) Date of Patent: Jun. 27, 2023

(54) REPAIR OF SHOULDER-JOINT LESIONS

(71) Applicant: OTS Medical Ltd., Herev LeEt (IL)

(72) Inventors: Assaf Dekel, Savyon (IL); Nir Lilach, Kfar Yehoshua (IL)

(73) Assignee: OTS Medical Ltd., Herzliya (IL)

( * ) Notice: Subject to any disclaimer, the term of this patent is extended or adjusted under 35 U.S.C. 154(b) by 0 days.

(21) Appl. No.: 17/987,047

(22) Filed: Nov. 15, 2022

(65) Prior Publication Data
US 2023/0074972 A1    Mar. 9, 2023

Related U.S. Application Data

(63) Continuation of application No. 17/522,034, filed on Nov. 9, 2021, now Pat. No. 11,529,236.

(60) Provisional application No. 63/216,590, filed on Jun. 30, 2021, provisional application No. 63/156,418, filed on Mar. 4, 2021.

(51) Int. Cl.
*A61F 2/28* (2006.01)
*A61F 2/30* (2006.01)

(52) U.S. Cl.
CPC ........ *A61F 2/2846* (2013.01); *A61F 2/30749* (2013.01); *A61F 2002/285* (2013.01); *A61F 2002/2835* (2013.01); *A61F 2002/2853* (2013.01); *A61F 2002/30461* (2013.01); *A61F 2002/30784* (2013.01); *A61F 2310/00359* (2013.01)

(58) Field of Classification Search
CPC .......... A61F 2/2846; A61F 2002/30461; A61F 2002/2835; A61F 2/30749; A61F 2002/285
See application file for complete search history.

(56) References Cited

U.S. PATENT DOCUMENTS

| 9,345,471 | B2 | 5/2016 | Sullivan |
| 9,526,621 | B2 | 12/2016 | Kuslich |
| 9,925,058 | B2 | 3/2018 | Wolfe et al. |
| 10,172,703 | B2 | 1/2019 | Adams et al. |
| 10,905,409 | B2 | 2/2021 | Brown et al. |
| 2006/0276871 | A1 | 12/2006 | Lamson et al. |
| 2007/0010857 | A1 | 1/2007 | Sugimoto et al. |
| 2007/0185532 | A1 | 8/2007 | Stone et al. |
| 2010/0203155 | A1 | 8/2010 | Wei et al. |
| 2012/0158053 | A1 | 6/2012 | Paulos |
| 2012/0239085 | A1 | 9/2012 | Schlotterback et al. |
| 2013/0110165 | A1 | 5/2013 | Burkhart et al. |
| 2013/0197530 | A1 | 8/2013 | McKay |
| 2013/0261634 | A1 | 10/2013 | McKay |

(Continued)

FOREIGN PATENT DOCUMENTS

| EP | 1366718 | 12/2003 |
| WO | WO 2009/113076 | 9/2009 |
| WO | WO 2022/185310 | 9/2022 |

OTHER PUBLICATIONS

International Search Report and the Written Opinion dated Jun. 23, 2022 From the International Searching Authority Re. Application No. PCT/IL2022/050232. (17 Pages).

(Continued)

*Primary Examiner* — Javier G Blanco

(57) ABSTRACT

The present invention relates to bone-implants for treating a lesion on a bone, comprising: a bone anchor, a container in communication with the bone anchor and an osteoconductive bone-filler material inside the container, and methods thereof.

14 Claims, 46 Drawing Sheets

(56) References Cited

U.S. PATENT DOCUMENTS

| | | |
|---|---|---|
| 2014/0031939 A1 | 1/2014 | Wolfe et al. |
| 2014/0200676 A1 | 7/2014 | Shimko et al. |
| 2017/0105716 A1 | 4/2017 | Burkhart |
| 2017/0150963 A1 | 6/2017 | Coleman |
| 2018/0214143 A1 | 4/2018 | Brown et al. |
| 2019/0274790 A1 | 9/2019 | Karmon |
| 2019/0290256 A1 | 9/2019 | Kehoe |
| 2022/0280300 A1 | 9/2022 | Dekel et al. |

OTHER PUBLICATIONS

Interview Summary dated Jun. 29, 2022 from US Patent and Trademark Office Re. U.S. Appl. No. 17/522,034. (3 pages).
Notice of Allowance dated Aug. 17, 2022 together with Interview Summary dated Aug. 4, 2022 from US Patent and Trademark Office Re. U.S. Appl. No. 17/522,034. (10 pages).
Official Action dated Apr. 22, 2022 from US Patent and Trademark Office Re. U.S. Appl. No. 17/522,034. (13 pages).
LifeNet Health "Allograft Bio-Implant Solutions", Sports Medicine Brochure: 1-16, 2015.
Moroder et al. "The Arthroscopic Bankart-Plus Procedure for Treatment of Anterior Shoulder Instability With Small to Intermediate Glenoid Defects", Arthroscopy Techniques 7(4):379-384, Apr. 2018.

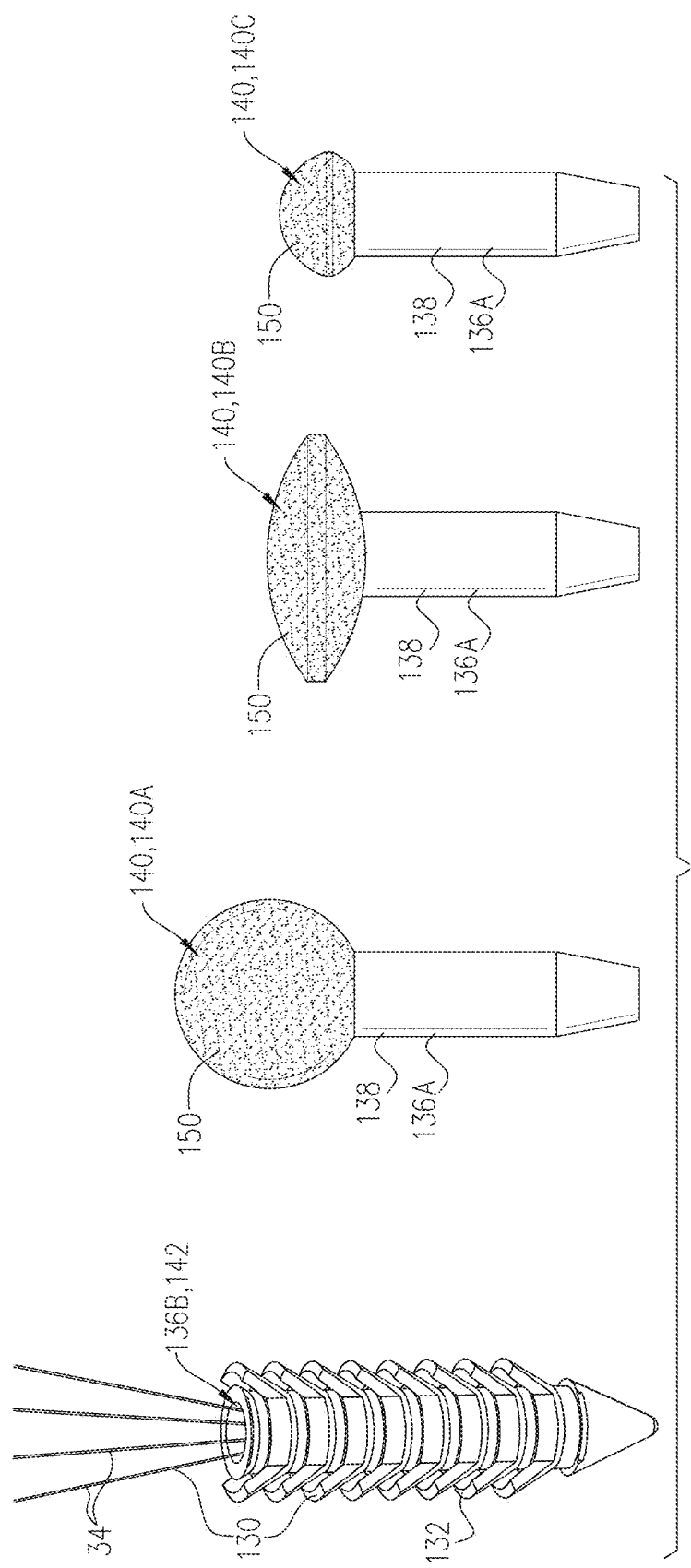

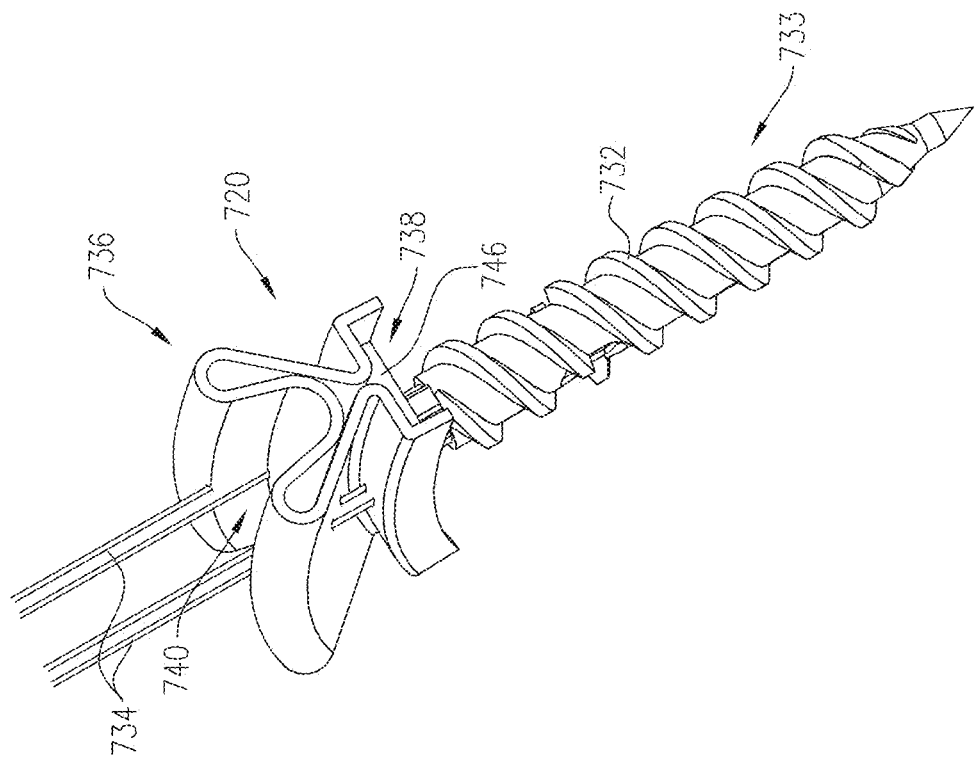

Figure 24e
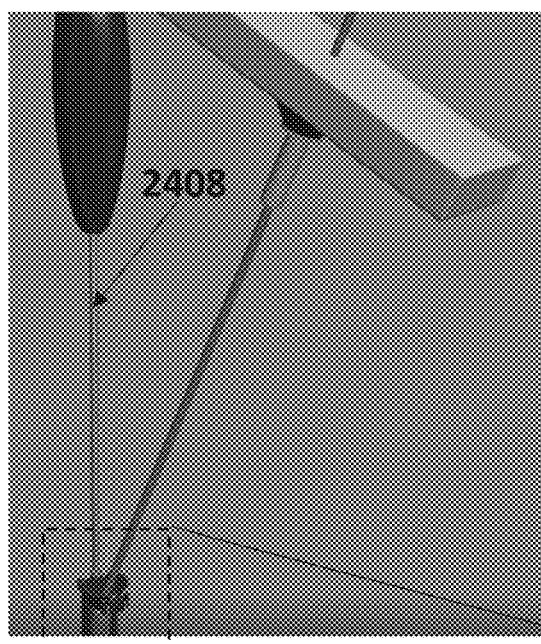
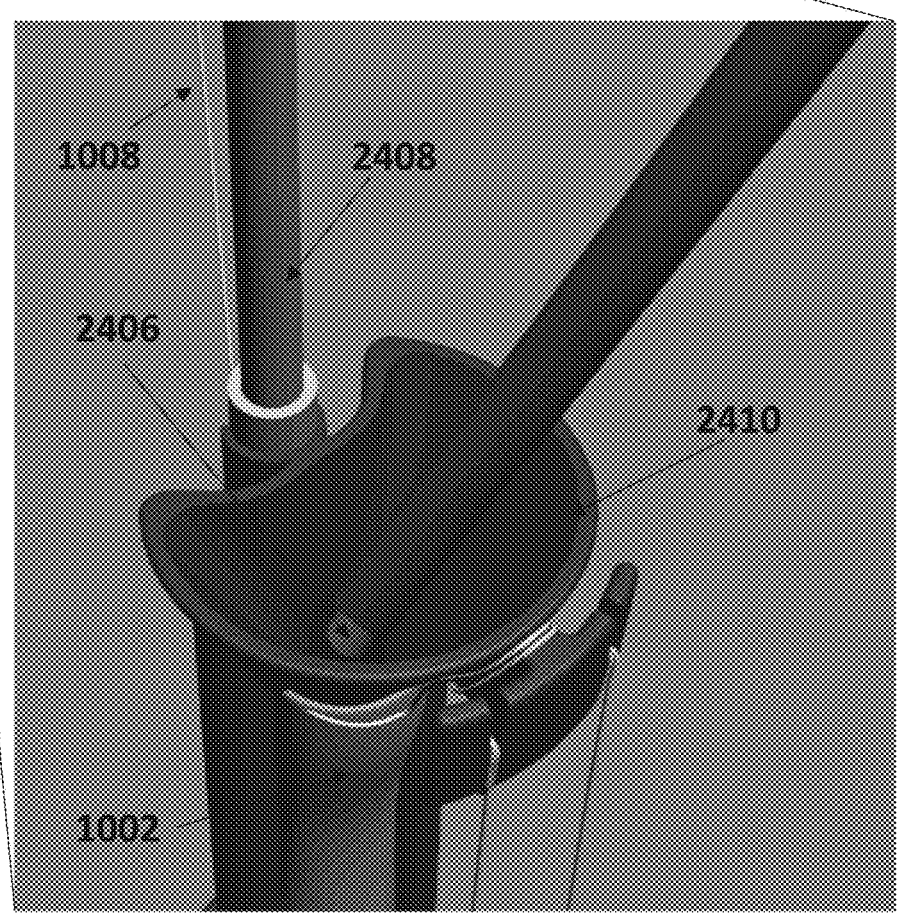
Figure 24f

Figure 24k
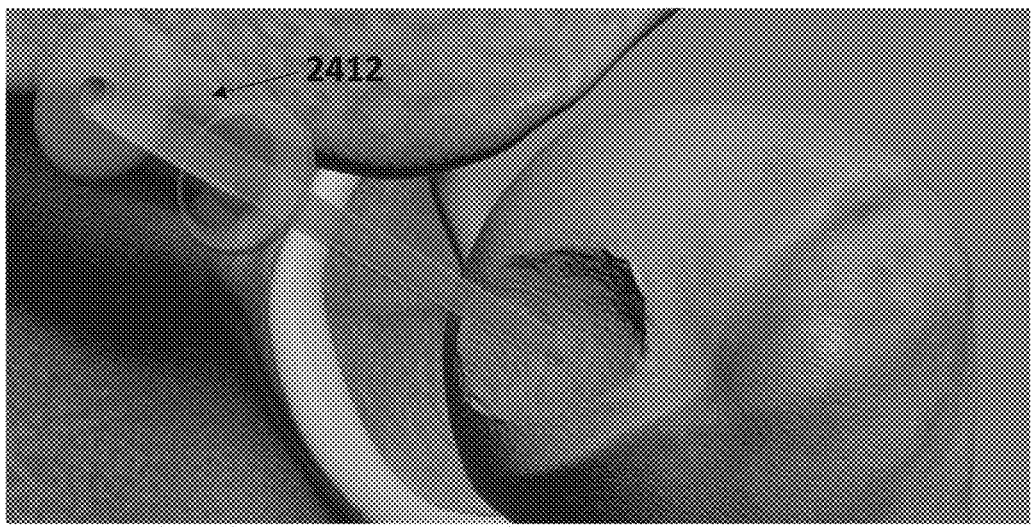
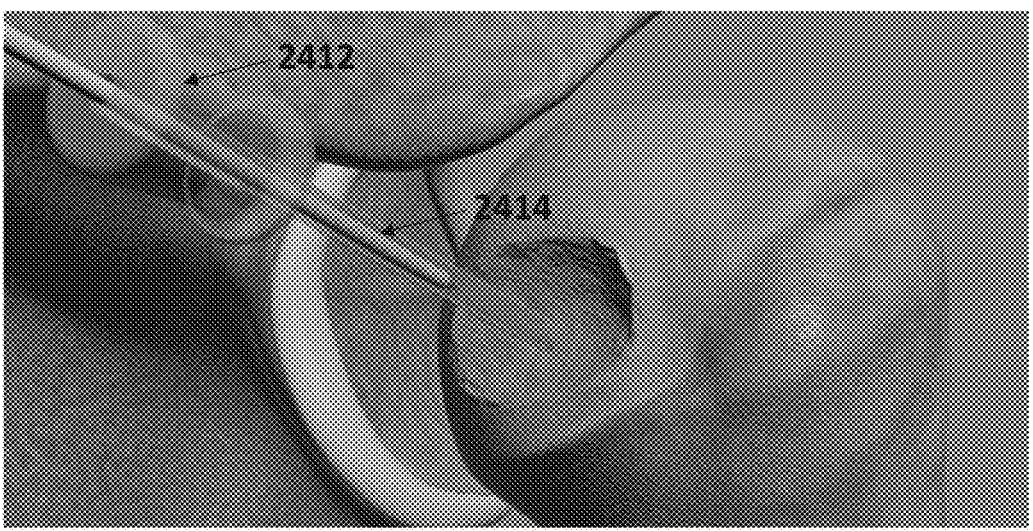
Figure 24l
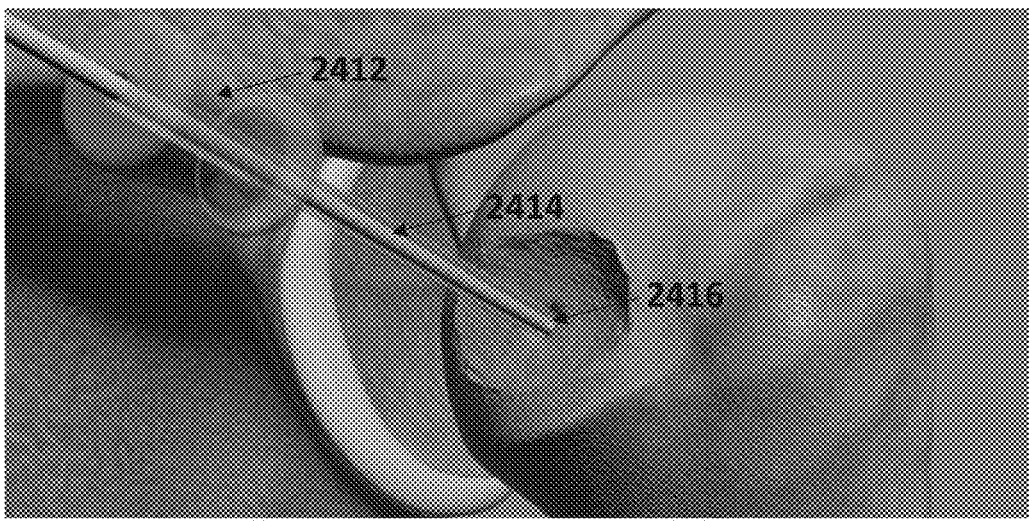
Figure 24m

Figure 24v
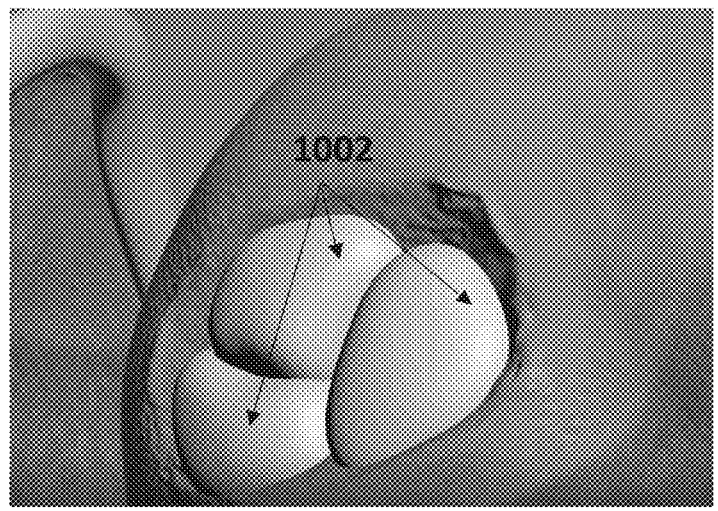
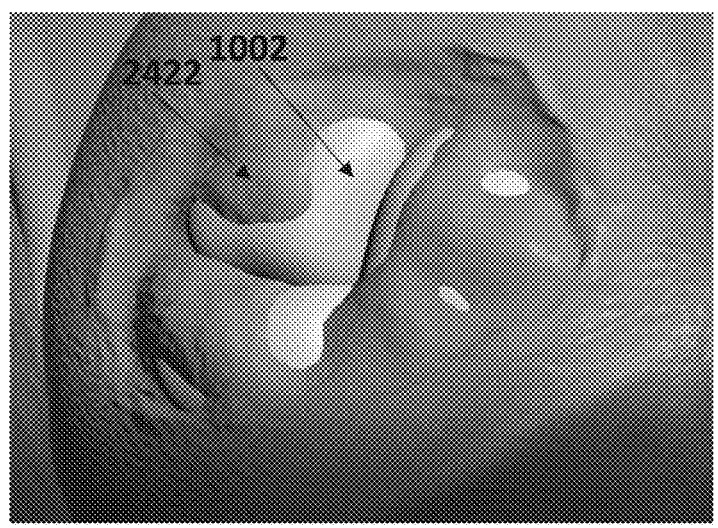
Figure 24w
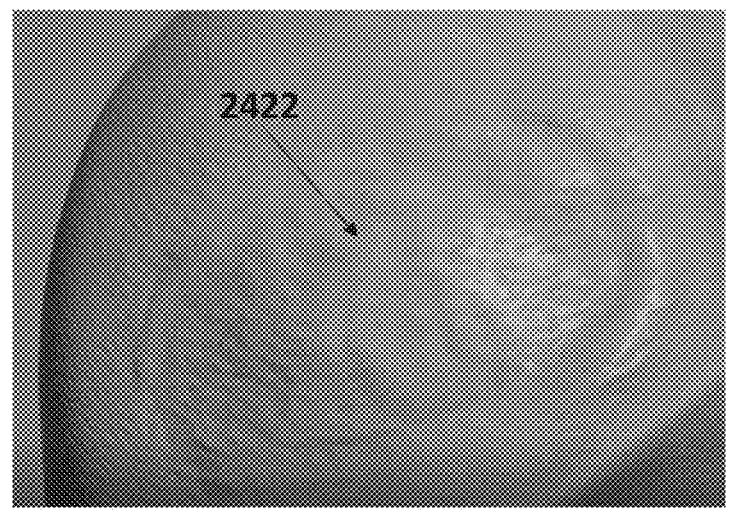
Figure 24x

REPAIR OF SHOULDER-JOINT LESIONS

RELATED APPLICATIONS

This application is a continuation of U.S. patent application Ser. No. 17/522,034 filed on Nov. 9, 2021, which claims the benefit of priority of U.S. Provisional Patent Application Nos. 63/156,418 filed on Mar. 4, 2021 and 63/216,590 filed on Jun. 30, 2021.

The contents of the above applications are all incorporated by reference as if fully set forth herein in their entirety.

FIELD AND BACKGROUND OF THE INVENTION

The present invention, in some embodiments thereof, relates to means and methods for repairing shoulder-joint lesions and, more particularly, but not exclusively, to minimally-invasive surgical means and methods for repairing shoulder-joint lesions. In anterior shoulder dislocations, the humeral head usually collides with the anterior rim of the glenoid, often causing a Hill-Sachs lesion and/or a Bankart lesion. A Hill-Sachs lesion is a compression fracture of the posterosuperolateral humeral head, while a Bankart lesion is a tear in the anterior (inferior) glenoid labrum of the shoulder.

Additional background art includes U.S. Pat. No. 10,905,409B2 disclosing a tissue repair assembly for attachment of tissue to bone or tissue to tissue having a soft anchoring implant with a length of suture there through for tensioning the implant and facilitating attachment of other tissue. The implant is a soft, flexible, three-dimensional structure that has a resident volume. An inserter tube facilitates the placement of the implant into bone or adjacent soft tissue where it may be deployed. Upon deployment, the soft anchoring implant shortens axially and expands radially, achieving a larger diameter than the hole through which it was placed, thus resisting pull out.

U.S. Patent Application Publication No. US20190290256A1 disclosing an all-suture anchor for attaching soft tissue to bone while creating an interference fit within a bone hole, and a deployment device for the all-suture anchor. The all-suture anchor includes an anchor body having first and second ends. The second end is folded toward the first end, creating a looped distal end of the anchor body, while the first and second ends of the anchor body form a proximal end. The anchor body is composed of a first material having a first density. A passing filament, of a second (different) density, is woven through the anchor body at passing locations such that a pair of free ends of the passing filament extends from the proximal end of the anchor body. The all-suture anchor additionally includes a binding filament bound axially at the proximal end of the anchor body around the first end and the second end of the anchor body.

U.S. Pat. No. 9,526,621B2 disclosing a method of correcting numerous bone abnormalities including bone tumors and cysts, avascular necrosis of the femoral head, tibial plateau fractures and compression fractures of the spine. The abnormality may be corrected by first accessing and boring into the damaged tissue or bone and reaming out the damaged and/or diseased area using any of the presently accepted procedures or the damaged area may be prepared by expanding a bag within the damaged bone to compact cancellous bone. After removal and/or compaction of the damaged tissue the bone is stabilized.

SUMMARY OF THE INVENTION

According to an aspect of some embodiments of the present invention there is provided a bone-implant for treating a lesion on a bone, comprising:
  a. a bone anchor;
  b. a container in communication with said anchor; and
  c. an osteoconductive bone-filler material inside said container.

According to some embodiments of the invention, said container is configured to act as said bone anchor for said bone-implant.

According to some embodiments of the invention, said container comprises a tubular sleeve.

According to some embodiments of the invention, the bone-implant further comprises one or more threads fixed to and extending proximally from said container.

According to some embodiments of the invention, said container and said one or more threads are arranged such that one or more knots formed upon knotting together of two or more longitudinal threads portions of the one or more threads allow a transition from an elongate, low-profile delivery configuration to a shortened radially-expanded deployment configuration of said container.

According to some embodiments of the invention, said one or more threads are configured to be used to attach an adjacent tissue to a location where said bone-implant is implanted.

According to some embodiments of the invention, said osteoconductive bone-filler material comprises one or more organic materials.

According to some embodiments of the invention, said one or more organic materials comprises one or more of bone marrow, bone marrow stem cells, osteogenic cells, preosteoblasts, osteoblasts, mesenchymal stem cells, bone marrow mesenchymal stem cells and pluripotent stem cells.

According to some embodiments of the invention, said container comprises one or more of:
  i. pores having sizes of from about 0.5 mm (height)×0.5 mm (width) to about 3 mm (height)×3 mm (width);
  ii. a porous scaffold;
  iii. an average of from about 20 CPI to about 30 CPI;
  iv. an average of from about 10 WPI to about 20 WPI.

According to some embodiments of the invention, said container comprises a biodegradable or non-biodegradable matrix.

According to some embodiments of the invention, said osteoconductive bone-filler material comprises a biodegradable or non-biodegradable matrix.

According to some embodiments of the invention, the bone-implant further comprises one or more additional sutures at a proximal end of said container for closing said proximal end after said osteoconductive bone-filler material is inserted in said container.

According to some embodiments of the invention, said container is configured to transition from an elongate, low-profile delivery configuration to a shortened radially-expanded deployment configuration against said bone upon distal sliding of said proximal end of said container along said one or more sutures toward a folded distal end of said container.

According to some embodiments of the invention, said container is configured to crumple during said transition from the elongate, low-profile delivery configuration to said shortened radially-expanded deployment configuration.

According to an aspect of some embodiments of the present invention there is provided a method for treating a lesion on a bone, the method comprising:

a. implanting a bone-void filler implant comprising a container with bone-void filler material in said lesion on said bone;

b. transitioning at least a portion of said bone-void filler implant from an elongate, low-profile delivery configuration to a shortened radially-expanded deployment configuration such that said bone-void filler implant at least partially fills said lesion, and said bone-filler material located in said container causes said bone-void filler implant to osseointegrate with said bone.

According to some embodiments of the invention, said transitioning comprises tying down one or more threads, said threads extending proximally from said bone-void filler implant.

According to some embodiments of the invention, said tying down comprises compressing said bone-void filler implant against said bone.

According to some embodiments of the invention, the method further comprises, after said transitioning, knotting together two or more longitudinal threads portions of said one or more threads.

According to some embodiments of the invention, the method further comprises, before implanting said bone anchor, drilling a whole in said bone to allow said bone anchor to be implanted.

According to some embodiments of the invention, said implanting said bone anchor comprises implanting said bone anchor in said lesion while at least a portion of said bone-void filler implant is disposed outside said lesion.

Following is a non-exclusive list including some examples of embodiments of the invention. The invention also includes embodiments which include fewer than all the features in an example and embodiments using features from multiple examples, also if not expressly listed below.

Example 1. A bone-implant for treating a lesion on a bone, comprising:
  a. a bone anchor;
  b. a container in communication with said anchor; and
  c. an osteoconductive bone-filler material inside said container.

Example 2. The bone-implant according to example 1, wherein said container is configured to act as said bone anchor for said bone-implant.

Example 3. The bone-implant according to example 1 or example 2, wherein said container comprises a tubular sleeve.

Example 4. The bone-implant according to any one of examples 1-3, further comprising one or more threads fixed to and extending proximally from said container.

Example 5. The bone-implant according to any one of examples 1-4, wherein said container and said one or more threads are arranged such that one or more knots formed upon knotting together of two or more longitudinal threads portions of the one or more threads allow a transition from an elongate, low-profile delivery configuration to a shortened radially-expanded deployment configuration of said container.

Example 6. The bone-implant according to any one of examples 1-5, wherein said one or more threads are configured to be used to attach an adjacent tissue to a location where said bone-implant is implanted.

Example 7. The bone-implant according to any one of examples 1-6, wherein said osteoconductive bone-filler material comprises one or more organic materials.

Example 8. The bone-implant according to any one of examples 1-7, wherein said one or more organic materials comprises one or more of bone marrow, bone marrow stem cells, osteogenic cells, preosteoblasts, osteoblasts, mesenchymal stem cells, bone marrow mesenchymal stem cells and pluripotent stem cells.

Example 9. The bone-implant according to any one of examples 1-8, wherein said container comprises a porous scaffold.

Example 10. The bone-implant according to any one of examples 1-9, wherein said container comprises pores having sizes of from about 0.5 mm (height)×0.5 mm (width) to about 3 mm (height)×3 mm (width).

Example 11. The bone-implant according to any one of examples 1-10, wherein said container comprises an average of from about 20 CPI to about 30 CPI.

Example 12. The bone-implant according to any one of examples 1-11, wherein said container comprises an average of from about 10 WPI to about 20 WPI.

Example 13. The bone-implant according to any one of examples 1-12, wherein said container comprises a biodegradable or non-biodegradable matrix.

Example 14. The bone-implant according to any one of examples 1-13, wherein said osteoconductive bone-filler material comprises a biodegradable or non-biodegradable matrix.

Example 15. The bone-implant according to any one of examples 1-14, further comprising one or more additional sutures at said proximal end for closing said proximal end after said osteoconductive bone-filler material is inserted in said container.

Example 16. The bone-implant according to any one of examples 1-15, wherein said container is configured to transition from an elongate, low-profile delivery configuration to a shortened radially-expanded deployment configuration against said bone upon distal sliding of said proximal end of said tubular sleeve along said one or more sutures toward said distal folded end.

Example 17. The bone-implant according to any one of examples 1-16, wherein said container is configured to crumple during said transition from the elongate, low-profile delivery configuration to said shortened radially-expanded deployment configuration.

Example 18. An implant system comprising the bone-implant according to example 1, the implant system further comprising an anchor inserter having a proximal end and a distal end;
  wherein said distal end of said anchor inserter is in communication to said container;
  wherein proximal portions of said one or more threads extend towards said proximal end of said anchor inserter.

Example 19. A method for treating a lesion on a bone, the method comprising:

a. implanting a bone-void filler implant comprising a container with bone-void filler material in said lesion on said bone;

b. transitioning at least a portion of said bone-void filler implant from an elongate, low-profile delivery configuration to a shortened radially-expanded deployment configuration such that said bone-void filler implant at least partially fills said lesion, and said bone-filler material located in said container causes said bone-void filler implant to osseointegrate with said bone.

Example 20. The method according to example 19, wherein said transitioning comprises tying down one or more threads, said threads extending proximally from said bone-void filler implant.

Example 21. The method according to example 19 or example 20, wherein said tying down comprises compressing said bone-void filler implant against said bone.

Example 22. The method according to any one of examples 19-21, further comprising, after said transitioning, knotting together two or more longitudinal threads portions of said one or more threads.

Example 23. The method according to any one of examples 19-22, further comprising, before implanting said bone anchor, drilling a whole in said bone to allow said bone anchor to be implanted.

Example 24. The method according to any one of examples 19-23, wherein implanting said bone anchor comprises implanting said bone anchor in said lesion while at least a portion of said bone-void filler implant is disposed outside said lesion.

According to an aspect of some embodiments of the present invention there is provided a bone-implant assembly is provided for treating a Hill-Sachs lesion on a humeral head. According to some embodiments of the invention, the bone-implant assembly comprises a suture anchor, which comprises (a) a bone anchor, which is configured to be implanted in the Hill-Sachs lesion on the humeral head, and (b) one or more sutures fixed to and extending proximally from the bone anchor. According to some embodiments of the invention, the bone-implant assembly further comprises a bone-void filler implant, which comprises an osteoconductive bone-filler material, and is coupled to the suture anchor.

According to some embodiments of the invention, in order to treat the Hill-Sachs lesion on the humeral head, the bone anchor is implanted in the Hill-Sachs lesion such that the one or more sutures fixed to the bone anchor extend proximally from the bone anchor out of the Hill-Sachs lesion. According to some embodiments of the invention, at least a portion of the bone-void filler implant is advanced over the one or more sutures toward the implanted bone anchor, such that the bone-void filler implant at least partially fills the Hill-Sachs lesion. In some embodiments, after the bone-void filler implant has been advanced toward the implanted bone anchor, the bone-void filler implant is tied down using the one or more sutures According to some embodiments of the invention, one or more than one bone-void filler implant may be implanted in the Hill-Sachs lesion, depending on the specific size and shape of the lesion and the size(s) and shape(s) of the implants.

According to some embodiments of the invention, over time, the one or more bone-void filler implants osseointegrate with the humeral head, thereby filling and treating the Hill-Sachs lesion.

According to an aspect of some embodiments of the present invention there is provided a bone-implant assembly is provided for treating a Bankart lesion. According to some embodiments of the invention, the bone-implant assembly comprises a bone anchor, which is shaped so as to define a distal portion configured to be implanted in the glenoid rim. According to some embodiments of the invention, the bone-implant assembly further comprises an elongate labrum receptacle, which is shaped so as to define (a) a distal glenoid-facing surface and (b) a proximal trough that (i) faces proximally away from the distal glenoid-facing surface and (ii) is shaped so as to receive a detached anteroinferior labrum.

According to some embodiments of the invention, the elongate labrum receptacle is configured to be coupled to a proximal portion of the bone anchor such that (a) the distal glenoid-facing surface rests against the glenoid rim and (b) the proximal trough faces proximally away from the glenoid rim, toward the detached anteroinferior labrum, in order to receive the detached anteroinferior labrum. According to some embodiments of the invention, the elongate labrum receptacle thus augments and enlarges the glenoid rim, in order to enable reattachment of the detached anteroinferior labrum to the glenoid rim.

According to some embodiments of the invention, the bone-implant assembly further comprises one or more sutures fixed to and extending proximally from the proximal portion of the bone anchor. According to some embodiments of the invention, the one or more sutures pass through the distal glenoid-facing surface of the elongate labrum receptacle and, optionally, the proximal trough. The elongate labrum receptacle is advanceable over the one or more sutures to the proximal portion of the bone anchor.

According to an aspect of some embodiments of the present invention there is provided a bone-implant assembly for treating a Hill-Sachs lesion on a humeral head, the bone-implant assembly including:

a suture anchor, which includes (a) a bone anchor, which is configured to be implanted in the Hill-Sachs lesion on the humeral head, and (b) one or more sutures fixed to and extending proximally from bone anchor 32; and a bone-void filler implant, which includes an osteoconductive bone-filler material, and is coupled to the suture anchor.

According to some embodiments of the invention, the bone-void filler implant includes a porous scaffold.

According to some embodiments of the invention, the osteoconductive bone-filler material includes a biodegradable or non-biodegradable matrix.

According to some embodiments of the invention, the bone anchor is threaded.

According to some embodiments of the invention, the bone-void filler implant is at least coupled to the one or more sutures of the suture anchor, so as to be coupled to the suture anchor.

According to some embodiments of the invention, the bone-void filler implant is at least coupled to the bone anchor, so as to be coupled to the suture anchor.

According to some embodiments of the invention, the bone-void filler implant is couplable to the bone anchor.

According to some embodiments of the invention, the bone-void filler implant and the bone anchor include respective couplers, which are shaped so as to be couplable to each other.

According to some embodiments of the invention, the bone-void filler implant is at least coupled to the bone anchor, so as to be coupled to the suture anchor.

According to some embodiments of the invention, the bone-void filler implant (a) has a proximal portion that is slidably coupled to the one or more sutures, so as to be coupled to the suture anchor, and (b) is configured to transition from an elongate, low-profile delivery configuration to a shortened radially-expanded deployment configuration against the humeral head upon distal sliding of the proximal portion of the bone-void filler implant along the one or more sutures toward the bone anchor.

According to some embodiments of the invention, a distal portion of the bone-void filler implant is fixed to the bone anchor.

According to some embodiments of the invention, a distal portion of the bone-void filler implant is non-slidably fixed to the one or more sutures.

According to some embodiments of the invention, the bone-void filler implant includes a patch.

According to some embodiments of the invention, a length of the patch is between 1 and 15 times a width of the patch when the bone-void filler implant is in the elongate, low-profile delivery configuration.

According to some embodiments of the invention, the patch is arranged as a tubular sleeve.

According to some embodiments of the invention, the patch is shaped so as to define at least first and second holes therethrough between first and second surfaces of the patch opposite each other, and at least one of the sutures passes through the first hole in a direction from the first surface to the second surface, and through the second hole in a direction from the second surface to the first surface.

According to some embodiments of the invention, the patch is configured, when in the shortened radially-expanded deployment configuration, to be accordion-pleated.

According to some embodiments of the invention, the patch is configured to crumple during a transition from the elongate, low-profile delivery configuration to the shortened radially-expanded deployment configuration.

According to some embodiments of the invention, the patch and the one or more sutures are arranged such that one or more knots formed upon knotting together of two or more longitudinal suture portions of the one or more sutures are covered by the patch.

According to some embodiments of the invention, the patch is arranged as a tubular sleeve, and the tubular sleeve and the one or more sutures are arranged such that the one or more knots formed upon the knotting together of the two or more longitudinal suture portions of the one or more sutures are within a proximal portion of the tubular sleeve, such that the one or more knots are covered by the tubular sleeve of the patch.

According to some embodiments of the invention, the bone-void filler implant has a greatest lateral dimension of between 0.2 and 4 cm when in the shortened radially-expanded deployment configuration.

According to some embodiments of the invention, an implant system is provided that includes the bone-implant assembly and further includes a delivery tube having proximal and distal end openings, the bone-implant assembly is partially disposed within the delivery tube such that (a) at least a portion of the bone anchor, (b) the bone-void filler implant, and (c) respective distal portions of the one or more sutures are disposed within the delivery tube with the proximal portion of the bone-void filler implant proximal to the bone anchor, and respective proximal portions of the one or more sutures extend out of the proximal end opening of the delivery tube.

According to some embodiments of the invention, at least two longitudinal suture portions of the sutures are loosely knotted together when the bone-implant assembly is partially disposed within the delivery tube.

According to some embodiments of the invention, the delivery tube has an external diameter of no more than 7 mm.

According to some embodiments of the invention, the bone-void filler implant is shaped as a ball.

According to some embodiments of the invention, the one or more sutures pass through the ball.

According to some embodiments of the invention, the ball is generally spherical.

According to some embodiments of the invention, the ball is generally ellipsoidal.

According to some embodiments of the invention, the bone-void filler implant includes a sponge impregnated with the osteoconductive bone-filler material.

According to some embodiments of the invention, the bone-void filler implant includes a sponge impregnated with the osteoconductive bone-filler material.

According to some embodiments of the invention, the bone-void filler implant includes a bone.

According to some embodiments of the invention, the bone-void filler implant is shaped as slices.

According to some embodiments of the invention, the bone-void filler implant includes a tubular woven mesh, which is configured to define one or more radial bulges when in a shortened radially-expanded deployment configuration.

According to an aspect of some embodiments of the present invention there is provided a method for treating a Hill-Sachs lesion on a humeral head, the method including:

implanting a bone anchor of a suture anchor of a bone-implant assembly in the Hill-Sachs lesion on the humeral head, such that one or more sutures fixed to the bone anchor extend proximally from the bone anchor out of the Hill-Sachs lesion; and advancing at least a portion of a bone-void filler implant of the bone-implant assembly over the one or more sutures toward the implanted bone anchor, such that the bone-void filler implant at least partially fills the Hill-Sachs lesion, and osteoconductive bone-filler material of the bone-void filler implant causes the bone-void filler implant to osseointegrate with the humeral head.

According to some embodiments of the invention, the method further includes, after advancing the bone-void filler implant toward the implanted bone anchor, tying down the bone-void filler implant using the one or more sutures.

According to some embodiments of the invention, tying down the bone-void filler implant using the one or more sutures includes compressing the bone-void filler implant against the humeral head.

According to some embodiments of the invention, the method further includes, after advancing the bone-void filler implant toward the implanted bone anchor, knotting together two or more longitudinal suture portions of the one or more sutures.

According to some embodiments of the invention, the bone-void filler implant is at least coupled to the one or more sutures of the suture anchor, so as to be coupled to the suture anchor.

According to some embodiments of the invention, the bone-void filler implant is at least coupled to the bone anchor, so as to be coupled to the suture anchor.

According to some embodiments of the invention, the method further includes coupling the bone-void filler implant to the bone anchor.

According to some embodiments of the invention, the bone-void filler implant is at least coupled to the bone anchor, so as to be coupled to the suture anchor.

According to some embodiments of the invention, implanting the bone anchor includes implanting the bone anchor in the Hill-Sachs lesion while at least a portion of the bone-void filler implant is disposed outside the Hill-Sachs lesion.

According to some embodiments of the invention, implanting the bone anchor includes implanting the bone anchor in the Hill-Sachs lesion while at least a portion of the bone-void filler implant is disposed within the Hill-Sachs lesion.

According to some embodiments of the invention, advancing the bone-void filler implant over the one or more sutures toward the implanted bone anchor includes transitioning the bone-void filler implant from an elongate, low-profile delivery configuration to a shortened radially-expanded deployment configuration against the humeral head, by distally sliding a proximal portion of the bone-void filler implant along the one or more sutures toward the implanted bone anchor.

According to some embodiments of the invention, a distal portion of the bone-void filler implant is fixed to the bone anchor.

According to some embodiments of the invention, a distal portion of the bone-void filler implant is non-slidably fixed to the one or more sutures.

According to some embodiments of the invention, the bone-void filler implant includes a patch.

According to some embodiments of the invention, a length of the patch is between 1 and 15 times a width of the patch when the bone-void filler implant is in the elongate, low-profile delivery configuration.

According to some embodiments of the invention, the patch is arranged as a tubular sleeve.

According to some embodiments of the invention, the patch is shaped so as to define at least first and second holes therethrough between first and second surfaces of the patch opposite each other, and at least one of the sutures passes through the first hole in a direction from the first surface to the second surface, and through the second hole in a direction from the second surface to the first surface.

According to some embodiments of the invention, the patch is configured, when in the shortened radially-expanded deployment configuration, to be accordion-pleated.

According to some embodiments of the invention, the patch is configured to crumple during a transition from the elongate, low-profile delivery configuration to the shortened radially-expanded deployment configuration.

According to some embodiments of the invention, the method further includes, after advancing the bone-void filler implant toward the implanted bone anchor, knotting together two or more longitudinal suture portions of the one or more sutures.

According to some embodiments of the invention, knotting together the two or more longitudinal suture portions of the one or more sutures includes making one or more knots such that the one or more knots are covered by the patch.

According to some embodiments of the invention, the method further includes, after making the one or more knots, cutting off excess portions of the two or more longitudinal suture portions such that proximal ends of the two or more longitudinal suture portions are covered by the patch.

According to some embodiments of the invention, the patch is arranged as a tubular sleeve, and making the one or more knots includes making the one or more knots within a proximal portion of the tubular sleeve, such that the one or more knots are covered by the tubular sleeve of the patch.

According to some embodiments of the invention, the method further includes, after making the one or more knots, cutting off excess portions of the two or more longitudinal suture portions such that proximal ends of the two or more longitudinal suture portions are covered by the tubular sleeve.

According to some embodiments of the invention, the method further includes, before implanting the bone anchor, introducing the bone-implant assembly into the Hill-Sachs lesion while the bone-implant assembly is partially disposed within a delivery tube such that (a) at least a portion of the bone anchor, (b) the bone-void filler implant, and (c) respective distal portions of the one or more sutures are disposed within the delivery tube with the proximal portion of the bone-void filler implant proximal to the bone anchor, such that respective proximal portions of the one or more sutures extend out of a proximal end opening of the delivery tube.

According to some embodiments of the invention, introducing the bone-implant assembly into the Hill-Sachs lesion includes introducing the bone-implant assembly into the Hill-Sachs lesion while at least two longitudinal suture portions of the sutures are loosely knotted together when the bone-implant assembly is partially disposed within the delivery tube.

According to some embodiments of the invention, the bone-void filler implant is shaped as a ball.

According to some embodiments of the invention, the one or more sutures pass through the ball.

According to some embodiments of the invention, the ball is generally spherical.

According to some embodiments of the invention, the ball is generally ellipsoidal.

According to some embodiments of the invention, the bone-void filler implant includes a sponge impregnated with the osteoconductive bone-filler material.

According to some embodiments of the invention, the bone-void filler implant includes a sponge impregnated with the osteoconductive bone-filler material.

According to some embodiments of the invention, the bone-void filler implant includes a bone.

According to some embodiments of the invention, the bone-void filler implant is shaped as slices.

According to some embodiments of the invention, the bone-void filler implant includes a tubular woven mesh, which is configured to define one or more radial bulges when in a shortened radially-expanded deployment configuration.

According to an aspect of some embodiments of the present invention there is provided a bone-implant assembly for treating a Bankart lesion characterized by detachment of an anteroinferior labrum from a glenoid rim, the bone-implant assembly including:

a bone anchor, which is shaped so as to define a distal portion configured to be implanted in the glenoid rim; and an elongate labrum receptacle, which is shaped so as to define (a) a distal glenoid-facing surface and (b) a proximal trough that (i) faces proximally away from the distal glenoid-facing surface and (ii) is shaped so as to receive the detached anteroinferior labrum, wherein the elongate labrum receptacle is configured to be coupled to a proximal portion of the bone anchor such that the distal glenoid-facing surface of the elongate labrum receptacle rests against the glenoid rim and the proximal trough faces proximally away from the glenoid rim toward the detached anteroinferior labrum in order to receive the detached anteroinferior labrum.

According to some embodiments of the invention, the proximal trough extends along an entire length of the elongate labrum receptacle and is open at both ends of the elongate labrum receptacle.

According to some embodiments of the invention, the proximal trough has a constant depth along the entire length of the elongate labrum receptacle.

According to some embodiments of the invention, the proximal trough has a length of between 0.5 and 2 cm.

According to some embodiments of the invention, the proximal trough has a greatest width of between 1 and 10 mm.

According to some embodiments of the invention, the proximal trough has a depth of between 1 and 10 mm.

According to some embodiments of the invention, the proximal trough has a length of between 0.5 and 2 cm.

According to some embodiments of the invention, the proximal trough has a greatest width of between 1 and 10 mm.

According to some embodiments of the invention, the distal glenoid-facing surface of the elongate labrum receptacle has a greatest width of between 1 and 12 mm.

According to some embodiments of the invention, the proximal trough includes a textile.

According to some embodiments of the invention, the textile is porous.

According to some embodiments of the invention, the proximal trough is flexible.

According to some embodiments of the invention, the bone-implant assembly further includes one or more sutures (a) fixed to and extending proximally from the proximal portion of the bone anchor, and (b) passing through the distal glenoid-facing surface of the elongate labrum receptacle, and the elongate labrum receptacle is advanceable over the one or more sutures to the proximal portion of the bone anchor.

According to some embodiments of the invention, two or more longitudinal suture portions of the one or more sutures are configured to be knotted together when passing through the distal glenoid-facing surface of the elongate labrum receptacle, so as to couple the elongate labrum receptacle to the proximal portion of the bone anchor.

According to some embodiments of the invention, each of the one or more openings has a cross-sectional area of between 0.2 and 10 mm2.

According to some embodiments of the invention, the distal glenoid-facing surface of the elongate labrum receptacle is shaped so as to define exactly two openings through which the one or more sutures pass, and each of the exactly two openings has a cross-sectional area of between 0.04 and 1.5 mm2.

According to some embodiments of the invention, the elongate labrum receptacle further includes a rigid base frame, which at least partially defines the distal glenoid-facing surface.

According to some embodiments of the invention, a distal surface of the rigid base frame defines at least a portion of the distal glenoid-facing surface of the elongate labrum receptacle.

According to some embodiments of the invention, the proximal portion of the bone anchor is shaped so as to define an anchor head, one of the anchor head and the rigid base frame is shaped so as to define at least one protrusion, and the other of the anchor head and the rigid base frame is shaped so as to define at least one protrusion receptacle configured to receive the at least one protrusion so as to prevent rotation of the elongate labrum receptacle with respect to the bone anchor when the elongate labrum receptacle is coupled to the bone anchor.

According to some embodiments of the invention, the at least one protrusion and the at least one protrusion receptacle are non-circular.

According to some embodiments of the invention, the proximal trough is more flexible than the rigid base frame.

According to some embodiments of the invention, the proximal portion of the bone anchor is shaped so as to define an anchor head, one of the anchor head and the rigid base frame is shaped so as to define at least one protrusion, and the other of the anchor head and the distal glenoid-facing surface of the elongate labrum receptacle is shaped so as to define at least one protrusion receptacle configured to receive the at least one protrusion so as to prevent rotation of the elongate labrum receptacle with respect to the bone anchor when the elongate labrum receptacle is coupled to the bone anchor.

According to some embodiments of the invention, the at least one protrusion and the at least one protrusion receptacle are non-circular.

According to some embodiments of the invention, the bone-implant assembly includes a plurality of bone anchors shaped so as to define a respective plurality of distal portions configured to be implanted in the glenoid rim.

According to some embodiments of the invention, the bone-implant assembly includes a plurality of elongate labrum receptacles, each of which is configured to be coupled to a proximal portion of at least one of the bone anchors.

According to some embodiments of the invention, the elongate labrum receptacle is configured to be coupled to respective proximal portions of at least two of the plurality of bone anchors.

According to some embodiments of the invention, the bone-implant assembly further includes a plurality of sutures (a) fixed to and extending proximally from the proximal portions of the bone anchors, respectively, and (b) passing through the distal glenoid-facing surface of the elongate labrum receptacle, and the elongate labrum receptacle is advanceable over the sutures to the proximal portions of the bone anchors, respectively.

According to some embodiments of the invention, the bone-implant assembly includes exactly a first number of bone anchors, the distal glenoid-facing surface of the elongate labrum receptacle is shaped so as to define exactly a second number of openings through which the sutures pass, respectively, the second number equal to two times the first number, and each of the openings has a cross-sectional area of between 0.04 and 1.5 mm2.

According to some embodiments of the invention, the at least two bone anchors are shaped so as to define respective anchor heads and respective protrusions that protrude proximally from the respective anchor head, and the distal glenoid-facing surface of the elongate labrum receptacle is shaped so as to define respective slots configured to receive the respective protrusions of the respective bone anchors, so as to prevent rotation of the elongate labrum receptacle with respect to the bone anchors when the elongate labrum receptacle is coupled to the bone anchors.

According to some embodiments of the invention, the at least two bone anchors are shaped so as to define respective anchor heads that are shaped so as to define respective slots, and the distal glenoid-facing surface of the elongate labrum receptacle is shaped so as to define respective protrusions, which are configured to be inserted into the respective slots of the anchor heads, so as to prevent rotation of the elongate labrum receptacle with respect to the bone anchors when the elongate labrum receptacle is coupled to the bone anchors.

According to some embodiments of the invention, the elongate labrum receptacle further includes a plurality of rigid base frames, which at least partially define the distal glenoid-facing surface.

According to some embodiments of the invention, the at least two bone anchors are shaped so as to define respective anchor heads and respective protrusions that protrude proximally from the respective anchor heads, and the rigid base frames are shaped so as to define respective protrusion receptacles configured to receive the respective protrusions so as to prevent rotation of the elongate labrum receptacle with respect to the bone anchors when the elongate labrum receptacle is coupled to the bone anchors.

According to some embodiments of the invention, the at least two bone anchors are shaped so as to define respective anchor heads that are shaped so as to define respective slots, and the rigid base frames are shaped so as to define respective protrusions, which are configured to be inserted into the respective slots of the anchor heads, so as to prevent rotation of the elongate labrum receptacle with respect to the bone anchors when the elongate labrum receptacle is coupled to the bone anchors.

According to an aspect of some embodiments of the present invention there is provided a method for treating a Bankart lesion characterized by detachment of an anteroinferior labrum from a glenoid rim, the method including:

implanting a distal portion of a bone anchor in the glenoid rim;

coupling an elongate labrum receptacle to a proximal portion of the bone anchor such that a distal glenoid-facing surface of the elongate labrum receptacle rests against the glenoid rim and a proximal trough of the elongate labrum receptacle faces proximally away from the distal glenoid-facing surface and the glenoid rim, toward the detached anteroinferior labrum; and inserting the detached anteroinferior labrum into the proximal trough.

According to some embodiments of the invention, the bone-implant assembly further includes one or more sutures (a) fixed to and extending proximally from the proximal portion of the bone anchor, and (b) passing through the distal glenoid-facing surface of the elongate labrum receptacle, and coupling the elongate labrum receptacle to the proximal portion of the bone anchor includes advancing the elongate labrum receptacle over the one or more sutures to the proximal portion of the bone anchor.

According to some embodiments of the invention, coupling the elongate labrum receptacle to the proximal portion of the bone anchor includes knotting together two or more longitudinal suture portions of the one or more sutures.

According to some embodiments of the invention, the method further includes suturing the detached anteroinferior labrum to the proximal trough using the one or more sutures.

According to some embodiments of the invention, the elongate labrum receptacle further includes a rigid base frame, which at least partially defines the distal glenoid-facing surface.

According to some embodiments of the invention, a distal surface of the rigid base frame defines at least a portion of the distal glenoid-facing surface of the elongate labrum receptacle.

According to some embodiments of the invention, the proximal portion of the bone anchor is shaped so as to define an anchor head, one of the anchor head and the rigid base frame is shaped so as to define at least one protrusion, the other of the anchor head and the rigid base frame is shaped so as to define at least one protrusion receptacle configured to receive the at least one protrusion, and coupling the elongate labrum receptacle to the proximal portion of the bone anchor includes inserting the at least one protrusion into the at least one protrusion receptacle so as to prevent rotation of the elongate labrum receptacle with respect to the bone anchor.

According to some embodiments of the invention, the at least one protrusion and the at least one protrusion receptacle are non-circular.

According to some embodiments of the invention, the proximal trough is more flexible than the rigid base frame.

According to some embodiments of the invention, the proximal portion of the bone anchor is shaped so as to define an anchor head, one of the anchor head and the rigid base frame is shaped so as to define at least one protrusion, the other of the anchor head and the distal glenoid-facing surface of the elongate labrum receptacle is shaped so as to define at least one protrusion receptacle configured to receive the at least one protrusion, and coupling the elongate labrum receptacle to the proximal portion of the bone anchor includes inserting the at least one protrusion into the at least one protrusion receptacle so as to prevent rotation of the elongate labrum receptacle with respect to the bone anchor.

According to some embodiments of the invention, the at least one protrusion and the at least one protrusion receptacle are non-circular.

According to some embodiments of the invention, the proximal trough extends along an entire length of the elongate labrum receptacle and is open at both ends of the elongate labrum receptacle.

According to some embodiments of the invention, the proximal trough has a constant depth along the entire length of the elongate labrum receptacle.

According to some embodiments of the invention, the proximal trough includes a textile.

According to some embodiments of the invention, the textile is porous.

According to some embodiments of the invention, the proximal trough is flexible.

According to some embodiments of the invention, implanting the distal portion of the bone anchor in the glenoid rim includes implanting a plurality of distal portions of a respective plurality of bone anchors in the glenoid rim.

According to some embodiments of the invention, coupling the elongate labrum receptacle to the proximal portion of the bone anchor includes coupling each of a plurality of elongate labrum receptacles to a proximal portion of at least one of the bone anchors.

According to some embodiments of the invention, coupling the elongate labrum receptacle to the proximal portion of the bone anchor includes coupling the elongate labrum receptacle to respective proximal portions of at least two of the plurality of bone anchors.

According to some embodiments of the invention, the bone-implant assembly further includes a plurality of sutures (a) fixed to and extending proximally from the proximal portions of the bone anchors, respectively, and (b) passing through the distal glenoid-facing surface of the elongate labrum receptacle, and coupling the elongate labrum receptacle to the proximal portion of the bone anchor includes advancing the elongate labrum receptacle over the sutures to the proximal portions of the bone anchors, respectively.

According to some embodiments of the invention, the at least two bone anchors are shaped so as to define respective anchor heads and respective protrusions that protrude proximally from the respective anchor heads, the distal glenoid-facing surface of the elongate labrum receptacle is shaped so as to define respective slots configured to receive the respective protrusions of the respective bone anchors, and coupling the elongate labrum receptacle to the proximal portions of the bone anchors includes inserting the protrusions into the respective slots so as to prevent rotation of the elongate labrum receptacle with respect to the bone anchors.

According to some embodiments of the invention, the at least two bone anchors are shaped so as to define respective anchor heads that are shaped so as to define respective slots, the distal glenoid-facing surface of the elongate labrum receptacle is shaped so as to define respective protrusions, which are configured to be inserted into the respective slots of the anchor heads, so as to prevent rotation of the elongate labrum receptacle with respect to the bone anchors when the elongate labrum receptacle is coupled to the bone anchors, and coupling the elongate labrum receptacle to the proximal portions of the bone anchors includes inserting the protrusions into the respective slots so as to prevent rotation of the elongate labrum receptacle with respect to the bone anchors.

According to some embodiments of the invention, the elongate labrum receptacle further includes a plurality of rigid base frames, which at least partially define the distal glenoid-facing surface.

According to some embodiments of the invention, the at least two bone anchors are shaped so as to define respective anchor heads and respective protrusions that protrude proximally from the respective anchor heads, the rigid base frames are shaped so as to define respective protrusion receptacles configured to receive the respective protrusions, and coupling the elongate labrum receptacle to the proximal portions of the bone anchors includes inserting the respective protrusions into the respective protrusion receptacles so as to prevent rotation of the elongate labrum receptacle with respect to the bone anchors.

According to some embodiments of the invention, the at least two bone anchors are shaped so as to define respective anchor heads that are shaped so as to define respective slots, the rigid base frames are shaped so as to define respective protrusions, which are configured to be inserted into the respective slots of the anchor heads, so as to prevent rotation of the elongate labrum receptacle with respect to the bone anchors when the elongate labrum receptacle is coupled to the bone anchors, and coupling the elongate labrum receptacle to the proximal portions of the bone anchors includes inserting the respective protrusions into the respective protrusion receptacles so as to prevent rotation of the elongate labrum receptacle with respect to the bone anchors.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4 is a schematic illustration of a kit comprising a plurality of one or more bone-implant assemblies of FIGS. 3A-B and a plurality of interchangeable bone-void filter implants, according to some embodiments of the invention;

FIGS. 12A-12B are schematic illustrations of a bone-implant assembly for treating a Bankart lesion, according to some embodiments of the invention;

FIGS. 24a, 24b, 24c, 24d, 24e, 24f, 24g, 24h, 24i, 24j, 24k, 24l, 24m, 24n, 24o, 24p, 24q, 24r, 24s, 24t, 24u, 24v, 24w and 24x are schematic illustrations of an exemplary procedure, according to some embodiments of the invention.

DESCRIPTION OF SPECIFIC EMBODIMENTS OF THE INVENTION

Figure 1:
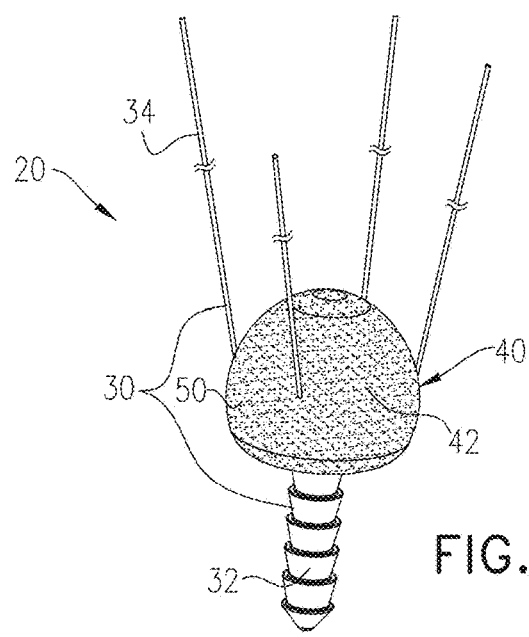
FIG. 1 is a schematic illustration of a bone-implant assembly for treating a Hill-Sachs lesion on a humeral head, according to some embodiments of the invention.

The present invention, in some embodiments thereof, relates to means and methods for repairing shoulder-joint lesions and, more particularly, but not exclusively, to minimally-invasive surgical means and methods for repairing shoulder-joint lesions.

Overview

An aspect of some embodiments of the invention relates to bone implants comprising one or more anchors and comprising one or more bone filling materials. In some embodiments, the bone filling materials are encased in an implant body and/or implant container (referred also just as "container"). In some embodiments, the implant container is attached to an anchor, the anchor configured to be attached to a bone and/or a part of a bone. In some embodiments, the implant body is configured to be the anchor. In some embodiments, the anchor is a soft tissue anchor. In some embodiments, the anchor is an all-suture anchor. In some embodiments, the anchor is a screw and/or other anchors known in the art. In some embodiments, the bone implant comprises one or more threads to change the configuration of the implant body/container. In some embodiments, one or more threads change the configuration of the implant body/container from a long, low profile, implant body/container to a compressed, wide profile implant body/container. In some embodiments, the one or more threads compress the implant body/container towards the anchor and/or the bone. In some embodiments, the implant body/container comprises an internal empty space for inserting the one or more bone filling materials. In some embodiments, the implant body/container comprises one or more additional threads for closing said implant body/container after the insertion of the one or more bone filling materials therein. In some embodiments, the one or more threads are configured to be used to hold one or more tissues to the bone. In some embodiments, the implant body is compressed towards the anchor not by threads, but it is physically pushed towards the anchor by a user. In some embodiments, there is an attaching mechanism between a part of the implant body/container and the anchor configured to maintain the implant body/container in the compressed, wide profile. For example a locking mechanism, an interlacing mechanism, etc.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is made to FIG. 1, which is a schematic illustration of a bone-implant assembly 20 for treating a Hill-Sachs lesion 22 on a humeral head 24, in accordance with some embodiments of the present invention.

Figure 2:
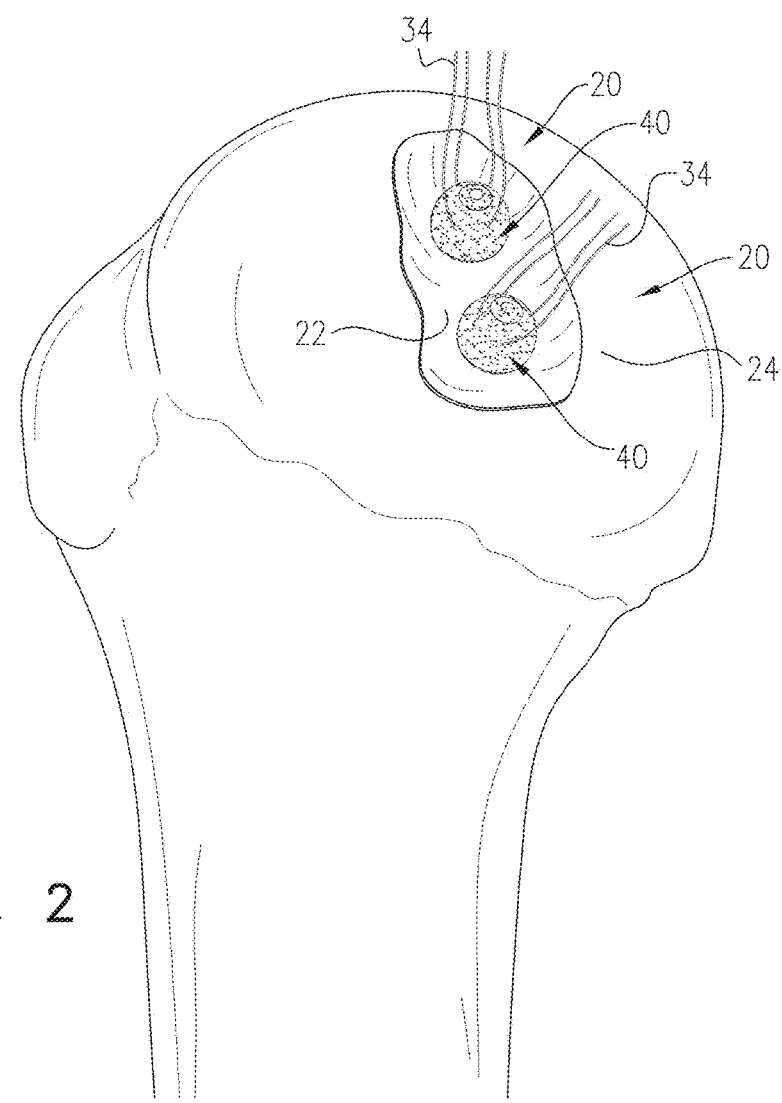
FIG. 2 is a schematic illustration of the bone-implant assembly of FIG. 1 partially deployed in a Hill-Sachs lesion on a humeral head, according to some embodiments of the invention.

Reference is also made to FIG. 2, which is a schematic illustration of bone-implant assembly 20 partially deployed in Hill-Sachs lesion 22 on humeral head 24, in accordance with some embodiments of the present invention.

In some embodiments, bone-implant assembly 20 comprises:

a suture anchor 30, which comprises (a) a bone anchor 32, which is configured to be implanted in Hill-Sachs lesion 22 on humeral head 24, such as shown in FIG. 2, and (b) typically, one or more (e.g., two or four) sutures 34 fixed to and extending proximally from bone anchor 32; and a bone-void filler implant 40, which comprises an osteoconductive bone-filler material 42, and is coupled to suture anchor 30.

In some embodiments, bone anchor 32 may comprise any bone anchor known in the art. In some embodiments, bone anchor 32 optionally is a screw-in anchor, in which case the anchor is threaded, as is known in the art. In some embodiments, alternatively, bone anchor 32 may be a non-screw-in anchor, which may be configured to change its morphology after being pushed into the bone, as is known in the art. In some embodiments, bone anchor 32 may be biodegradable (absorbable) or non-biodegradable (nonabsorbable), as is known in the bone anchor art. For example, bone anchor 32 may comprise titanium or PEEK, as is known in the art. In some embodiments, optionally, bone anchor 32 has a diameter of at least 1.3 mm, no more than 5 mm (such as no more than 2.8 mm), and/or between 1.3 and 5 mm, such as between 1.3 and 2.8 mm, e.g., 1.3 mm, 1.8 mm, 2.3 mm, or 2.8 mm.

In some embodiments, the one or more sutures 34 may comprise any sutures known in the art, such as braided, unbraided, absorbable, nonabsorbable, or hybrid types. In some embodiments, optionally, the one or more sutures 34 are coupled to an eyelet of bone anchor 32.

In some embodiments, the one or more sutures 34 define one or more longitudinal suture portions, which may be formed from separate sutures or one or more sutures looped through the head of bone anchor 32.

In some embodiments, bone-void filler implant 40 comprises a porous scaffold.

In some embodiments, osteoconductive bone-filler material 42 comprises a biodegradable or non-biodegradable matrix.

For example, osteoconductive bone-filler material 42 may comprise a polyester braid tube, distributed by Secant group (Telford, Pa., USA), calcium phosphate spheres distributed by Himed (Old Bethpage, N.Y., USA).

In some embodiments, bone-void filler implant 40 is coupled at least to the one or more sutures 34 of the suture anchor 30, so as to be coupled to suture anchor 30, such as shown in FIGS. 1 and 2, and described hereinbelow with reference to FIGS. 6A and 6B.

In some embodiments, alternatively or additionally, bone-void filler implant 40 is coupled bone anchor 32, so as to be coupled to suture anchor 30.

In some embodiments, bone-void filler implant 40 is shaped as a ball 50. In some embodiments, optionally, the one or more sutures 34 pass through ball 50, such as shown in FIGS. 1 and 2.

In some embodiments, ball 50 is generally spherical or generally ellipsoidal.

In some embodiments, bone-void filler implant 40 comprises a sponge impregnated with osteoconductive bone-filler material 42.

In some embodiments, bone-void filler implant 40 comprises bone (either autologous bone or allograft bone, such as from a bone bank).

Reference is still made to FIG. 2. In some embodiments, in order to treat Hill-Sachs lesion 22 on humeral head 24, bone anchor 32 is implanted in Hill-Sachs lesion 22 on humeral head 24, such that the one or more sutures 34 fixed to bone anchor 32 extend proximally from bone anchor 32 out of Hill-Sachs lesion 22. In some embodiments, at least a portion (e.g., all) of bone-void filler implant 40 is advanced over the one or more sutures 34 toward implanted bone anchor 32, such that bone-void filler implant 40 at least partially fills Hill-Sachs lesion 22. In some embodiments, at least after bone-void filler implant 40 has been advanced over the one or more sutures 34 toward implanted bone anchor 32, bone-void filler implant 40 is in contact with bone anchor 32, such as shown in FIG. 2. In some embodiments, optionally, the bone-void filler implant is in contact with the bone anchor even before the bone-void filler implant has been advanced over the one or more sutures 34 toward implanted bone anchor 32.

In some embodiments, alternatively, the one or more sutures 34 are not provided, in which case bone-void filler implant 40 is advanced toward bone anchor 32 without being advanced over sutures. In some embodiments, further alternatively, bone-void filler implant 40 is coupled to bone anchor 32 prior to implantation of the bone anchor in the Hill-Sachs lesion.

In some embodiments, during implantation of bone anchor 32 in Hill-Sachs lesion 22, at least a portion of bone-void filler implant 40 (e.g., an entirety of bone-void filler implant 40) is disposed outside Hill-Sachs lesion 22, and the at least a portion of bone-void filler implant 40 disposed outside Hill-Sachs lesion 22 is advanced into Hill-Sachs lesion 22 over the one or more sutures 34 after the implantation of bone anchor 32.

Figure 10A:
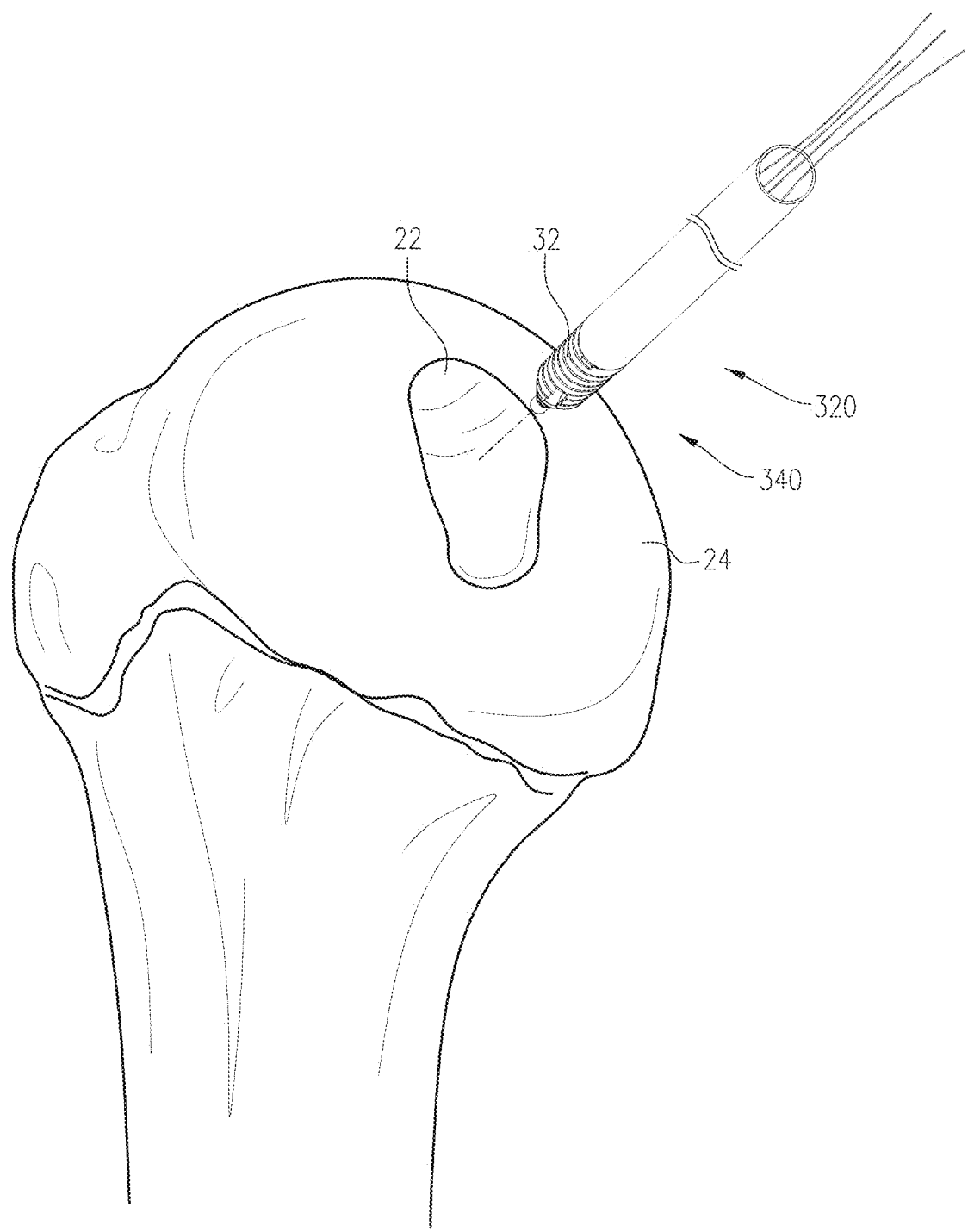
FIGS. 10A, 10B, 10C, 10D, 10E, 10F, 10G and 10H are schematic illustrations of a method for treating a Hill-Sachs lesion on a humeral head using the implant system of FIG. 9, according to some embodiments of the invention.
Figure 10B:
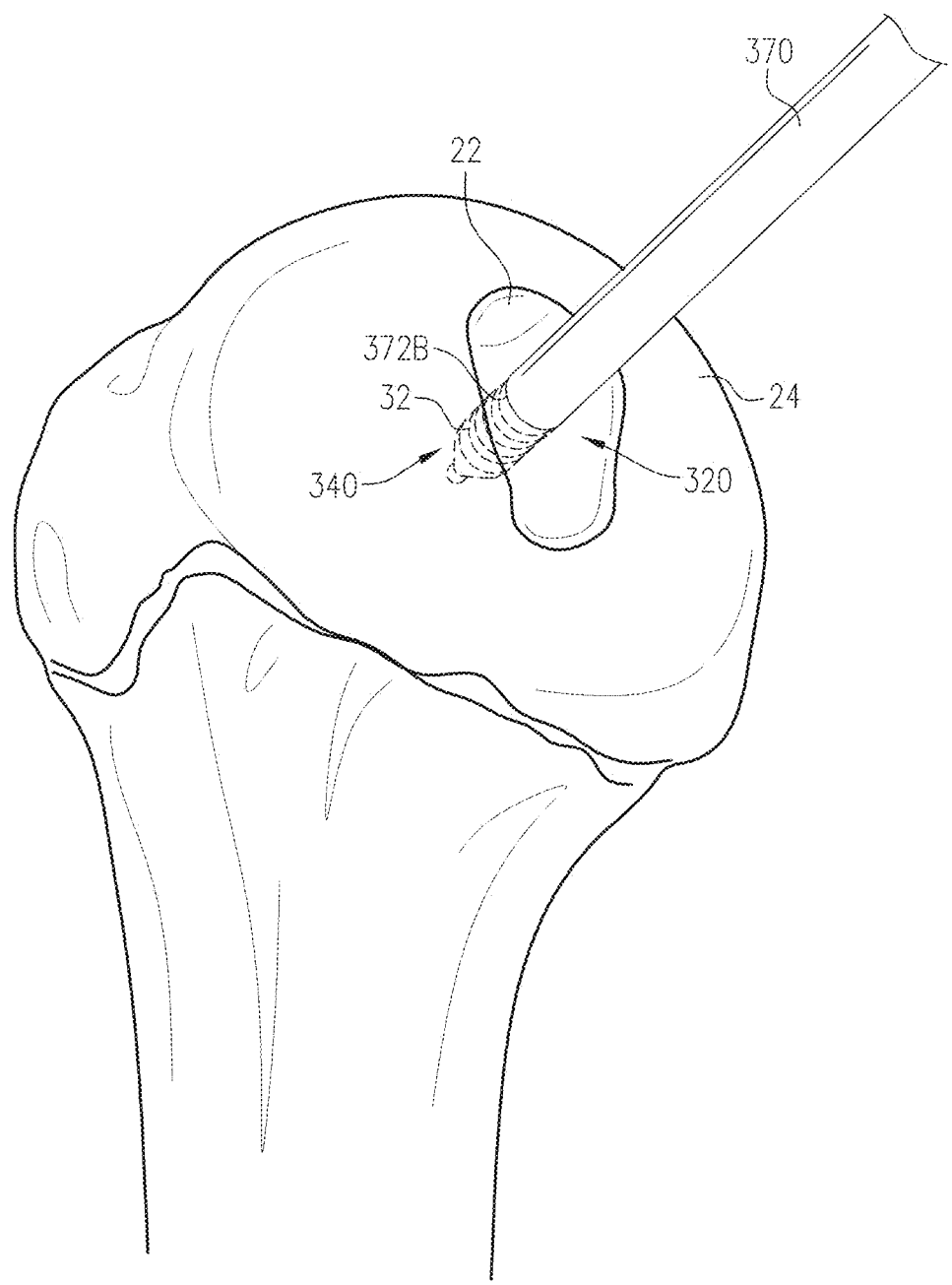
Figure 10C:
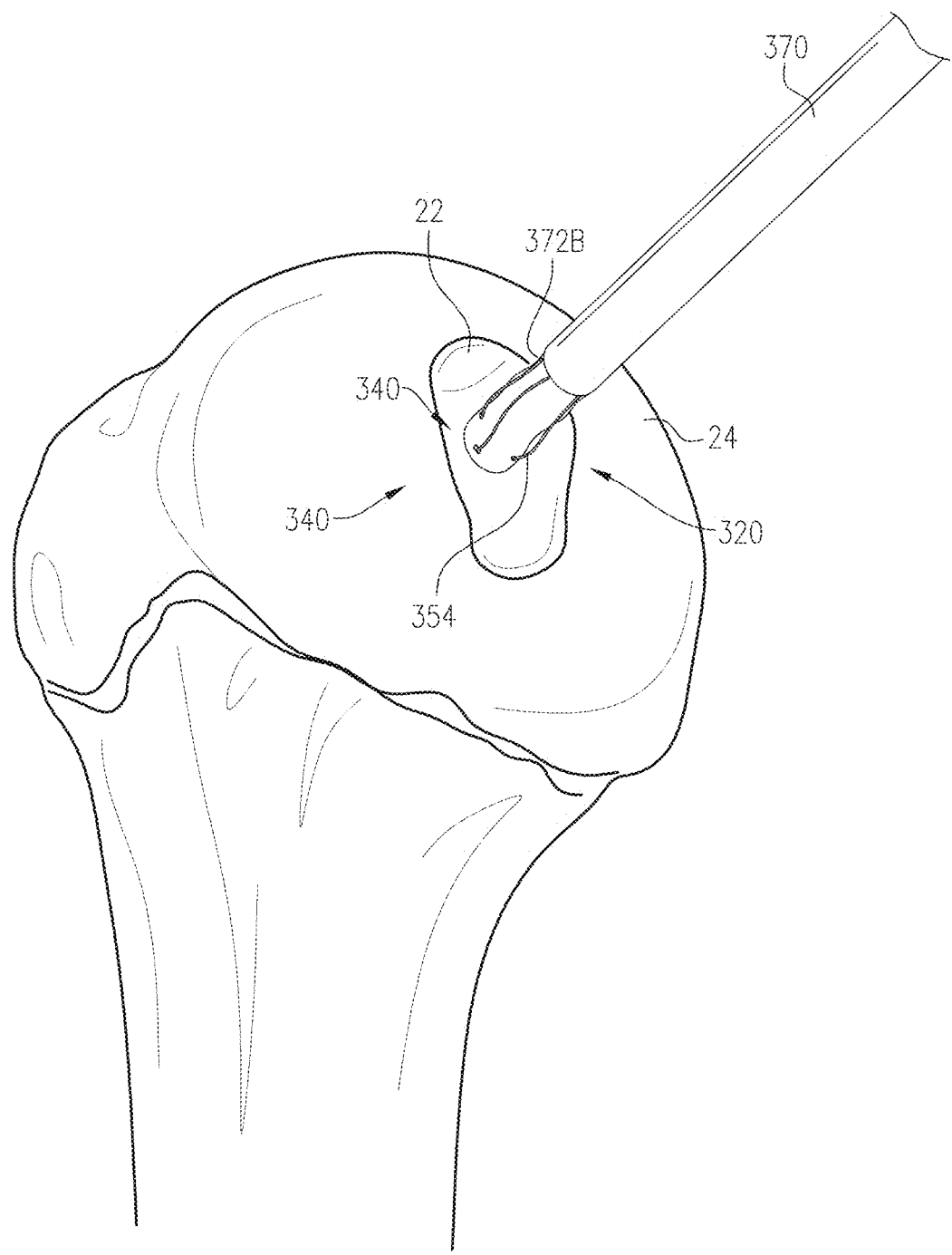
Figure 10D:
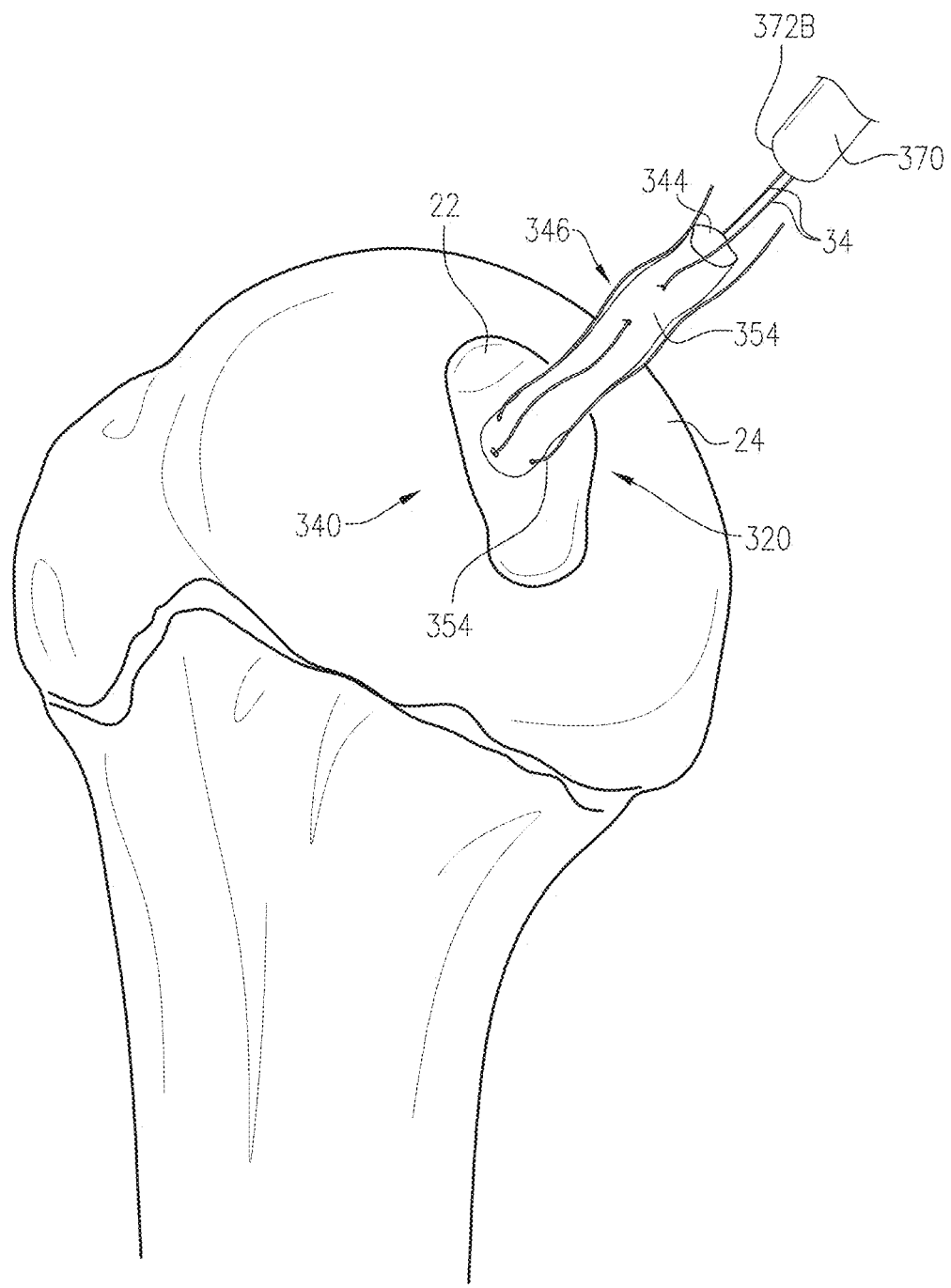
Figure 10F:
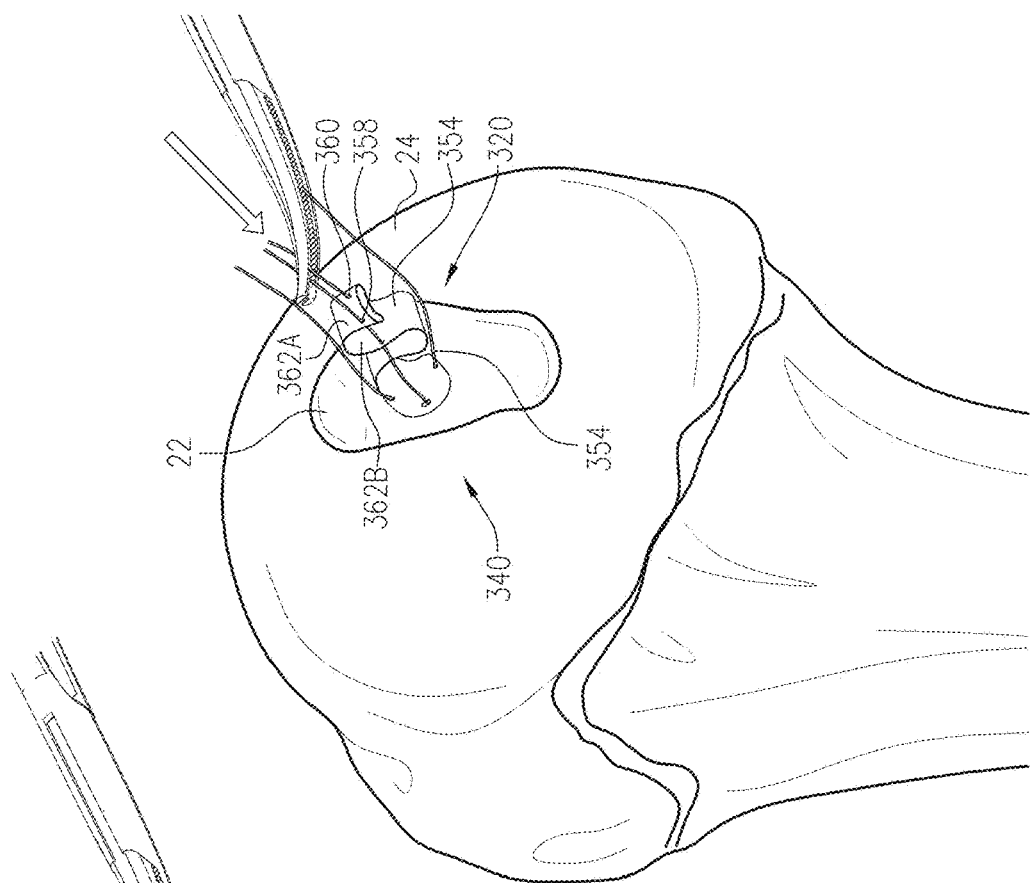
Figure 10E:
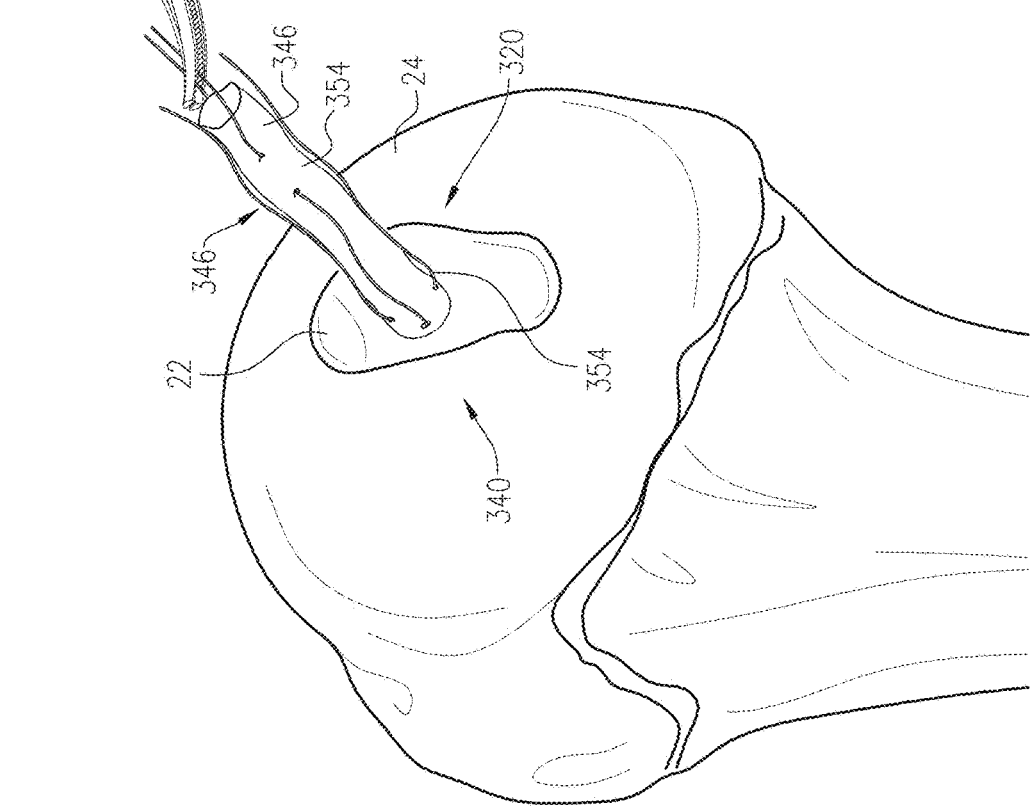
Figure 10H:
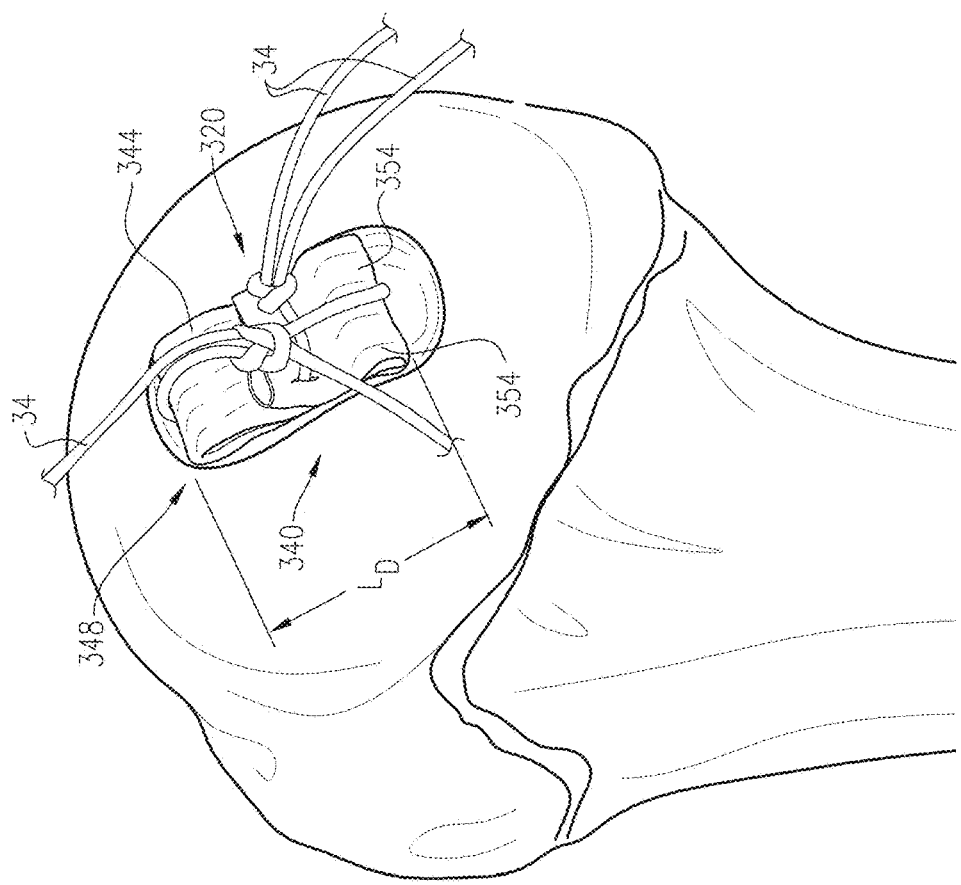
Figure 10G:
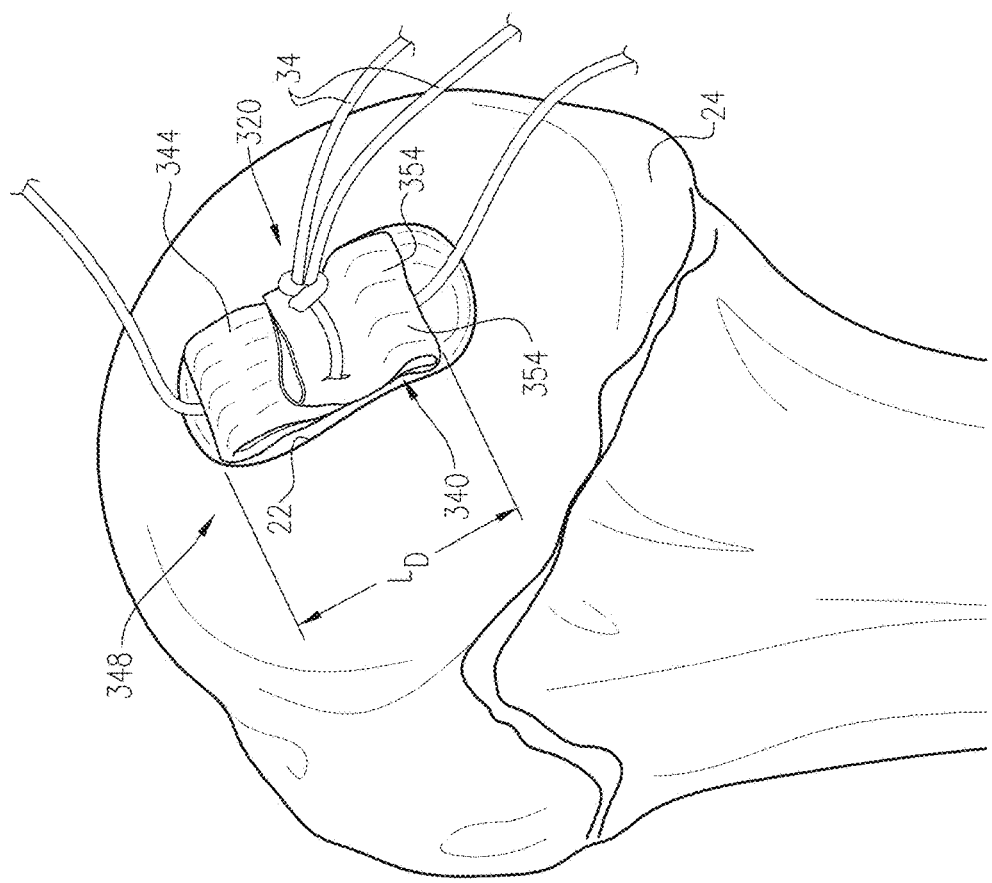

In some embodiments, after bone-void filler implant 40 has been advanced toward implanted bone anchor 32, bone-void filler implant 40 is tied down using the one or more sutures 34 (not shown in FIG. 2, but shown for bone-void filler implant 340 in FIGS. 10G-H). In some embodiments, optionally, tying down bone-void filler implant 40 using the one or more sutures 34 compresses bone-void filler implant 40 against humeral head 24 (and/or against bone anchor 32).

In some embodiments, one or more than one bone-void filler implant 40 may be implanted in Hill-Sachs lesion 22, depending on the specific size and shape of the lesion and the size(s) and shape(s) of the implants.

In some embodiments, over time, the one or more bone-void filler implants 40 osseointegrate with humeral head 24, thereby filling and treating Hill-Sachs lesion 22.

Figure 3A:
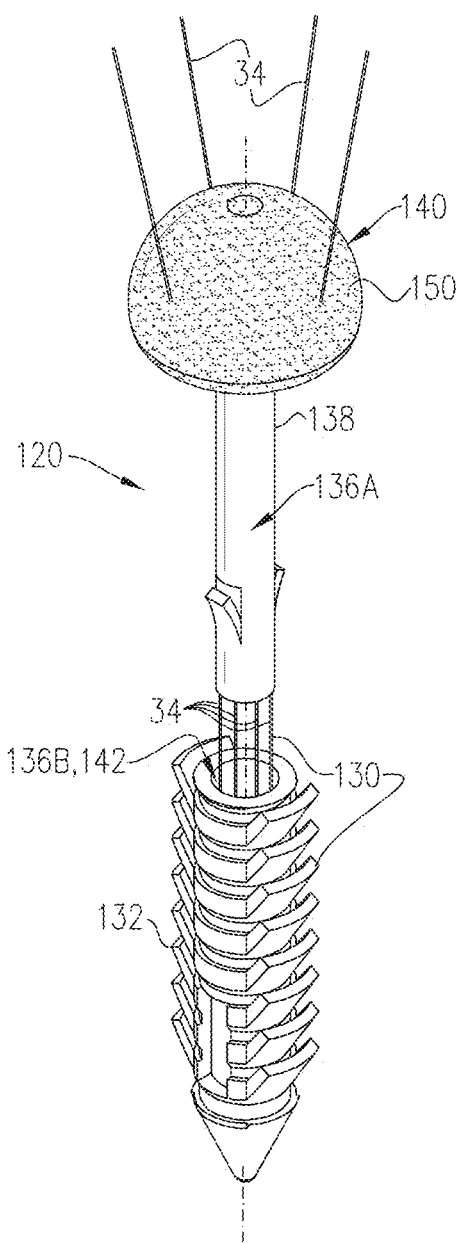
FIGS. 3A-B are schematic illustrations of another bone-implant assembly, according to some embodiments of the invention.
Figure 3B:
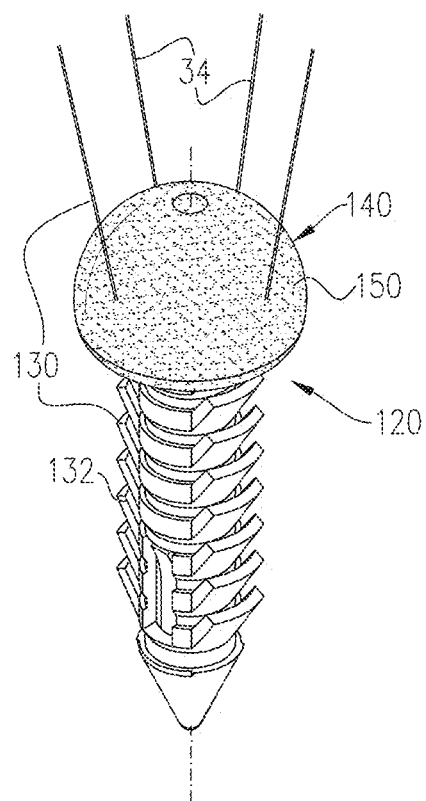

Reference is now made to FIGS. 3A-3B, which are schematic illustrations of a bone-implant assembly 120, in accordance with some embodiments of the present invention. In some embodiments, bone-implant assembly 120 is one configuration of bone-implant assembly 20, described hereinabove with reference to FIGS. 1 and 2, and may implement any of the features thereof, mutatis mutandis.

In some embodiments, bone-implant assembly 120 comprises a suture anchor 130 and a bone-void filler implant 140. In some embodiments, suture anchor 130 comprises a bone anchor 132 and one or more sutures 34 fixed to and extending proximally from bone anchor 132. In some embodiments, bone-void filler implant 140 is coupled to suture anchor 130, such as via the one or more sutures 34. In some embodiments, suture anchor 130, bone anchor 132, the one or more sutures 34, and bone-void filler implant 140 may implement any of the features of suture anchor 30, bone anchor 32, the one or more sutures 34, and bone-void filler implant 40, respectively, as described hereinabove with reference to FIGS. 1-2, mutatis mutandis. Like reference numerals refer to like parts.

In some embodiments, bone-void filler implant 140 is couplable to bone anchor 132. In some embodiments, bone-void filler implant 140 and bone anchor 132 comprise respective couplers 136A and 136B, which are shaped so as to be couplable to each other, optionally such that the couplers cannot be decoupled from each other without damaging bone-implant assembly 120.

In some embodiments, coupler 136A is male and coupler 136B is female. In some embodiments, for example, coupler 136A of bone-void filler implant 140 may be shaped so as to define a shaft 138, and coupler 136B of bone anchor 132 may be shaped so as to define a channel 142 that is shaped so as to receive shaft 138 therein. In some embodiments, coupler 136A is female and coupler 136B is male (configuration not shown).

In some embodiments, the one or more sutures 34 may extend through bone-void filler implant 140, such as through an internal space defined through shaft 138 of bone-void filler implant 140, if provided, and/or through a ball 150 thereof.

Reference is now made to FIG. 4, which is a schematic illustration of a kit 152 comprising a plurality of one or more bone-implant assemblies 120 and a plurality of interchangeable bone-void filter implants 140, in accordance with some embodiments of the present invention. (A single interchangeable bone-void filter implant 140 is shown in FIGS. 3A-3B.) In some embodiments, interchangeable bone-void filter implants 140 differ from one another in size and/or shape. In some embodiments, based on the specific shape of a subject's Hill-Sachs lesion 22, the surgeon selects one or more interchangeable bone-void filter implants 140 and couples them to respective suture anchors 130. In some embodiments, interchangeable bone-void filter implants 140 and suture anchors 130 may implement any of the features of bone-void filter implant 40 and suture anchor 30, respectively, described hereinabove with reference to FIGS. 1 and 2, mutatis mutandis.

In some embodiments, as described above, interchangeable bone-void filter implants 140 differ from one another in size and/or shape. In some embodiments, for example, a bone-void filler implant 140A may be generally spherical, a bone-void filler implant 140B may be generally ellipsoidal, and a bone-void filler implant 140C may be partially generally spherical and partially generally ellipsoidal.

Figure 5:
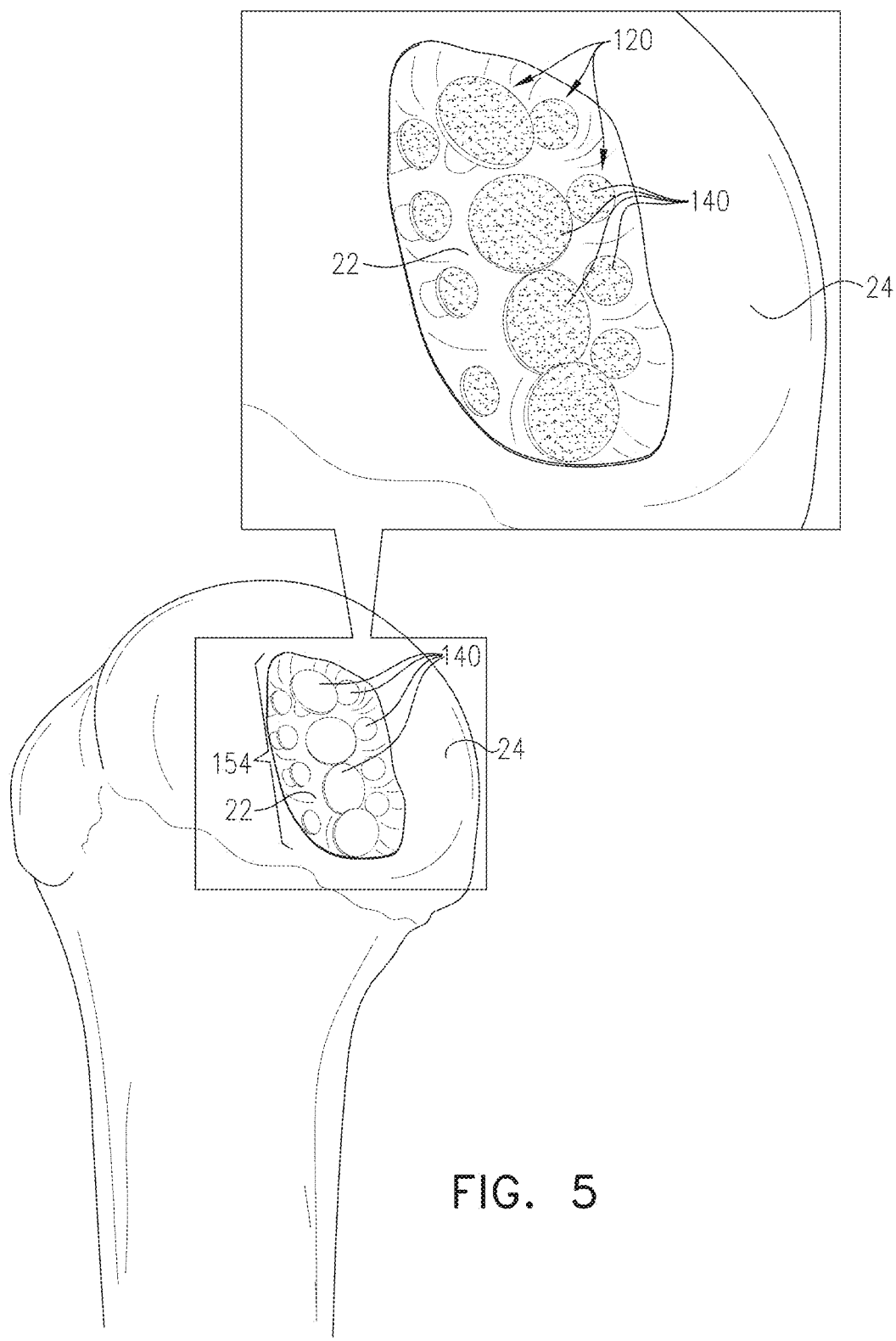
FIG. 5 is a schematic illustration of a plurality of bone-implant assemblies of the kit of FIG. 4 partially deployed in a Hill-Sachs lesion on a humeral head, according to some embodiments of the invention.

Reference is now made to FIG. 5, which is a schematic illustration of a plurality of bone-implant assemblies 120 of kit 154 partially deployed in Hill-Sachs lesion 22 on humeral head 24, in accordance with some embodiments of the present invention. In some embodiments, although bone-implant assemblies 120 are shown as comprising respective bone-void filler implants 140, bone-implant assemblies 120 may alternatively comprise bone-void filler implants 40, described hereinabove with reference to FIGS. 1-2 and 3A-3B, mutatis mutandis. In addition, although the one or more sutures 34 are typically provided (and optionally used for typing down the bone-void filler implants), the sutures are not shown in FIG. 5.

In some embodiments, such as shown, the respective bone-void filler implants 140 of bone-implant assemblies 120 have different sizes and/or shapes in order to accommodate and fill the specific shape of the subject's Hill-Sachs lesion 22.

In some embodiments, between one and five bone-implant assemblies 120 are used to fill Hill-Sachs lesion 22, depending on the size and shape of the specific Hill-Sachs lesion 22.

Figure 6A:
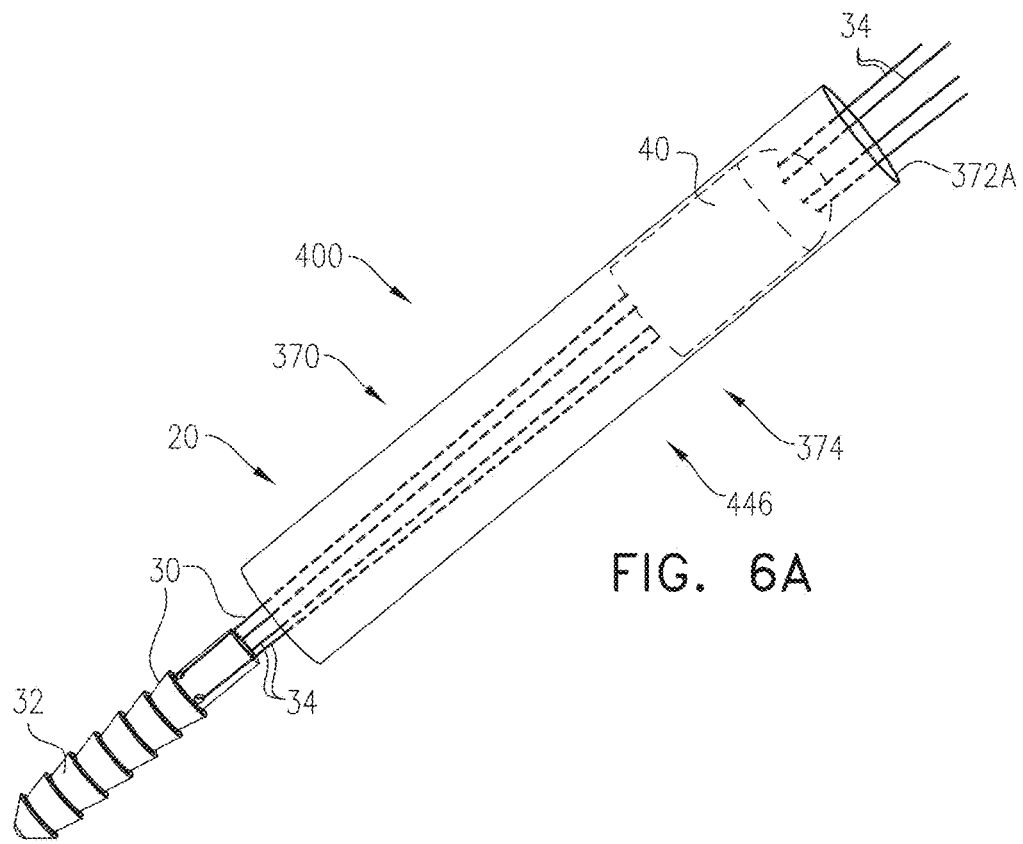
FIGS. 6A-B are schematic illustrations of a portion of a method for treating a Hill-Sachs lesion using an implant system, according to some embodiments of the invention.
Figure 6B:
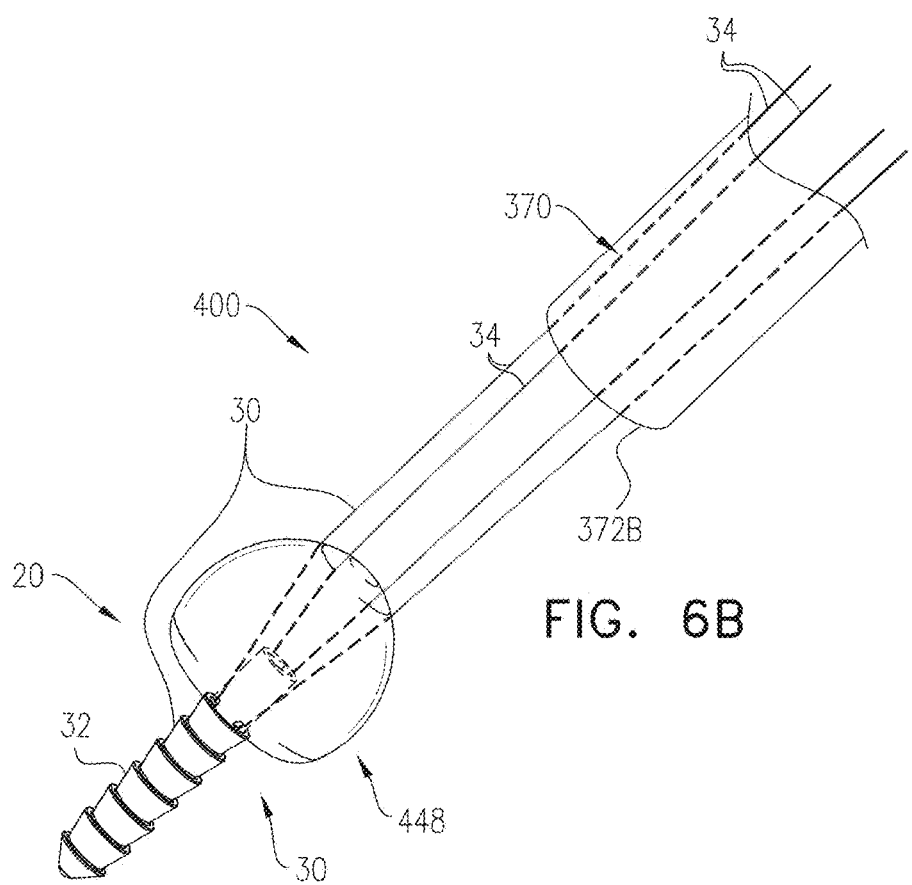

Reference is again made to FIGS. 1 and 2, and is additionally made to FIGS. 6A-6B, which are schematic illustrations of a portion of a method for treating Hill-Sachs lesion 22 using an implant system 400, in accordance with some embodiments of the present invention. In some embodiments, implant system 400 comprises a bone-implant assembly 20, described hereinabove with reference to FIGS. 1 and 2, and delivery tube 370, described hereinbelow with reference to FIGS. 9 and 10A-D. In some embodiments, as described above, and as can be seen in FIG. 6A, typically bone-void filler implant 40 is at least coupled to the one or more sutures 34 of suture anchor 30, so as to be coupled to the suture anchor.

In some embodiments, such as shown in FIG. 6A, bone-implant assembly 20 is partially disposed within delivery tube 370 such that (a) at least a portion of bone anchor 32, (b) bone-void filler implant 40, and (c) the respective distal portions of the one or more sutures 34 are disposed within delivery tube 370. In some embodiments, respective proximal portions 376 of the one or more sutures 34 extend out of proximal end opening 372A of delivery tube 370.

In some embodiments, bone-void filler implant 40 is configured to transition from a low-profile compressed delivery configuration 446 when disposed within delivery tube 370, such as shown in FIG. 6A, to an expanded deployment configuration 448 upon release from delivery tube 370, such as shown in FIG. 6B. In some embodiments, bone-void filler implant 40 is configured to automatically transition from low-profile compressed delivery configuration 446 to expanded deployment configuration 448 upon release from delivery tube 370.

Figure 7:
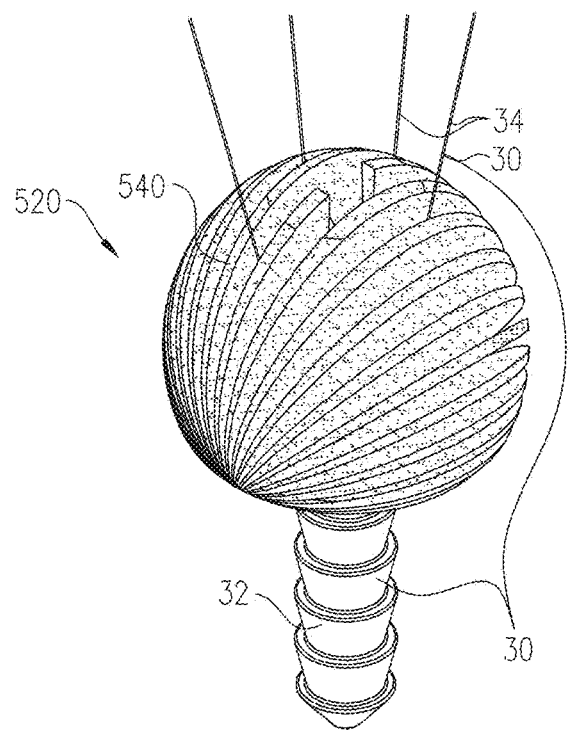
FIG. 7 is a schematic illustration of a bone-implant assembly, according to some embodiments of the invention.

Reference is now made to FIG. 7, which is a schematic illustration of a bone-implant assembly 520, in accordance with some embodiments of the present invention. In some embodiments, other than as described below, bone-implant assembly 520 is generally similar to bone-implant assembly 20, described hereinabove with reference to FIGS. 1 and 2, and may implement any of the features thereof, mutatis mutandis. Like reference numerals refer to like parts.

In some embodiments, a bone-void filler implant 540 of bone-implant assembly 520 is shaped so as define thin slices, e.g., radiating out from a distal portion of bone-void filler implant 540 that is coupled to bone anchor 32. In some embodiments, for example, the thin slices may be fan-shaped or shaped like Hasselback potatoes. In some embodiments, for example, bone-void filler implant 540 may define between three and 50 slices, such as between five and 30 slices.

Figures 8A, 8B, 8C:
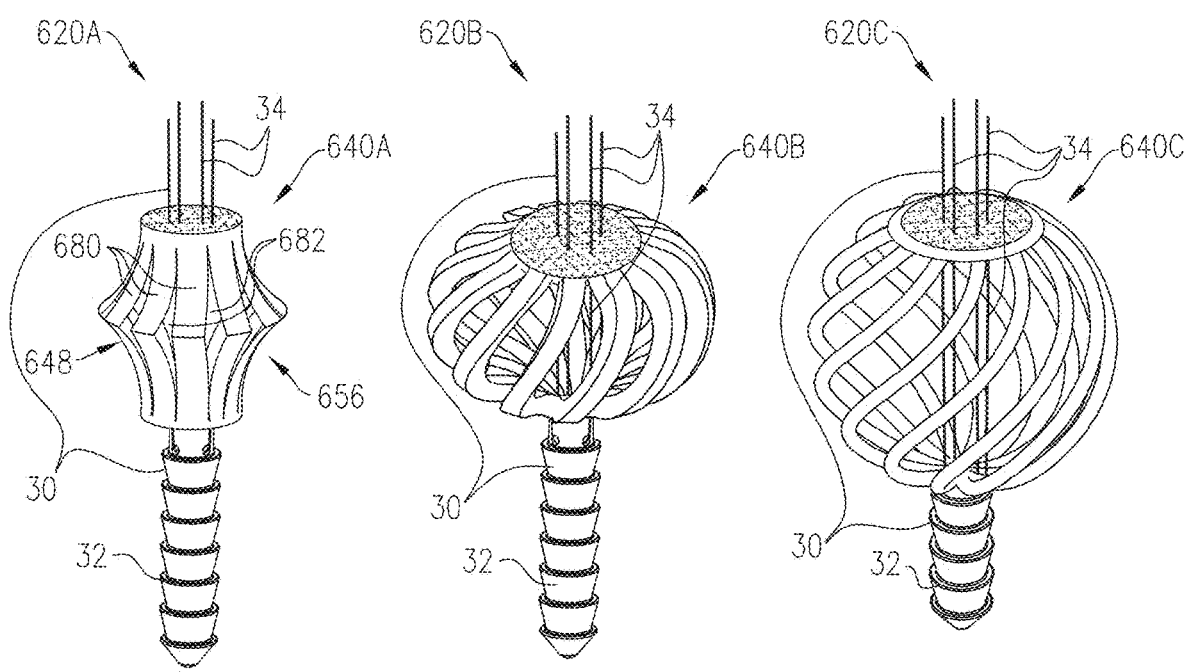
FIGS. 8A, 8B and 8C are schematic illustrations of additional bone-implant assemblies, according to some embodiments of the invention.

Reference is now made to FIGS. 8A-8C, which are schematic illustrations of bone-implant assemblies 620A, 620B, and 620C, in accordance with respective embodiments of the present invention. In some embodiments, other than as described below, bone-implant assemblies 620A, 620B, and 620C are generally similar to bone-implant assembly 20, described hereinabove with reference to FIGS. 1 and 2, and may implement any of the features thereof, mutatis mutandis. Like reference numerals refer to like parts.

In some embodiments, a bone-void filler implant 640A of bone-implant assembly 620A comprises a tubular sleeve 656. In some embodiments, either the material of tubular sleeve 656 comprises osteoconductive bone-filler material 42, or tubular sleeve 656 contains osteoconductive bone-filler material 42 within an internal space defined by the tubular sleeve. In some embodiments, bone-void filler implant 640A is configured to transition from an elongate, low-profile delivery configuration (not shown) to a shortened radially-expanded deployment configuration 648 (as shown in FIG. 8A) against humeral head 24 upon distal sliding of a proximal portion 644 of bone-void filler implant 640A along the one or more sutures 34 toward bone anchor 32.

In some embodiments, when bone-void filler implant 640A is in shortened radially-expanded deployment configuration 648, tubular sleeve 656 is shaped so as to define one or more radial bulges 680, typically a plurality of radial bulges 680 that bulge is respective different radial directions, such as shown. In some embodiments, tubular sleeve 656 may thus have a shape somewhat similar to some slitted Chinese paper lanterns, as is known in the decorative arts.

In some embodiments, optionally, tubular sleeve 656 is shaped so as to define one or more axially-oriented slits 682, typically a plurality of slits, which help bone-void filler implant 640A transition to shortened radially-expanded deployment configuration 648, such that tubular sleeve 656 defines the one or more radial bulges 680. In some embodiments, optionally, the number of slits equals the number of radial bulges.

In some embodiments, optionally, tubular sleeve 656 comprises a woven mesh.

In some embodiments, bone-void filler implants 640B and 640C of bone-implant assemblies 620B and 620C, respectively, comprise thin elongate elements that are curved so as to define a hollow ball-shaped sleeve. In some embodiments, bone-implant assemblies 620B and 620C are generally similar to bone-implant assembly 620A, and may implement any of the features thereof, mutatis mutandis.

Figure 9:
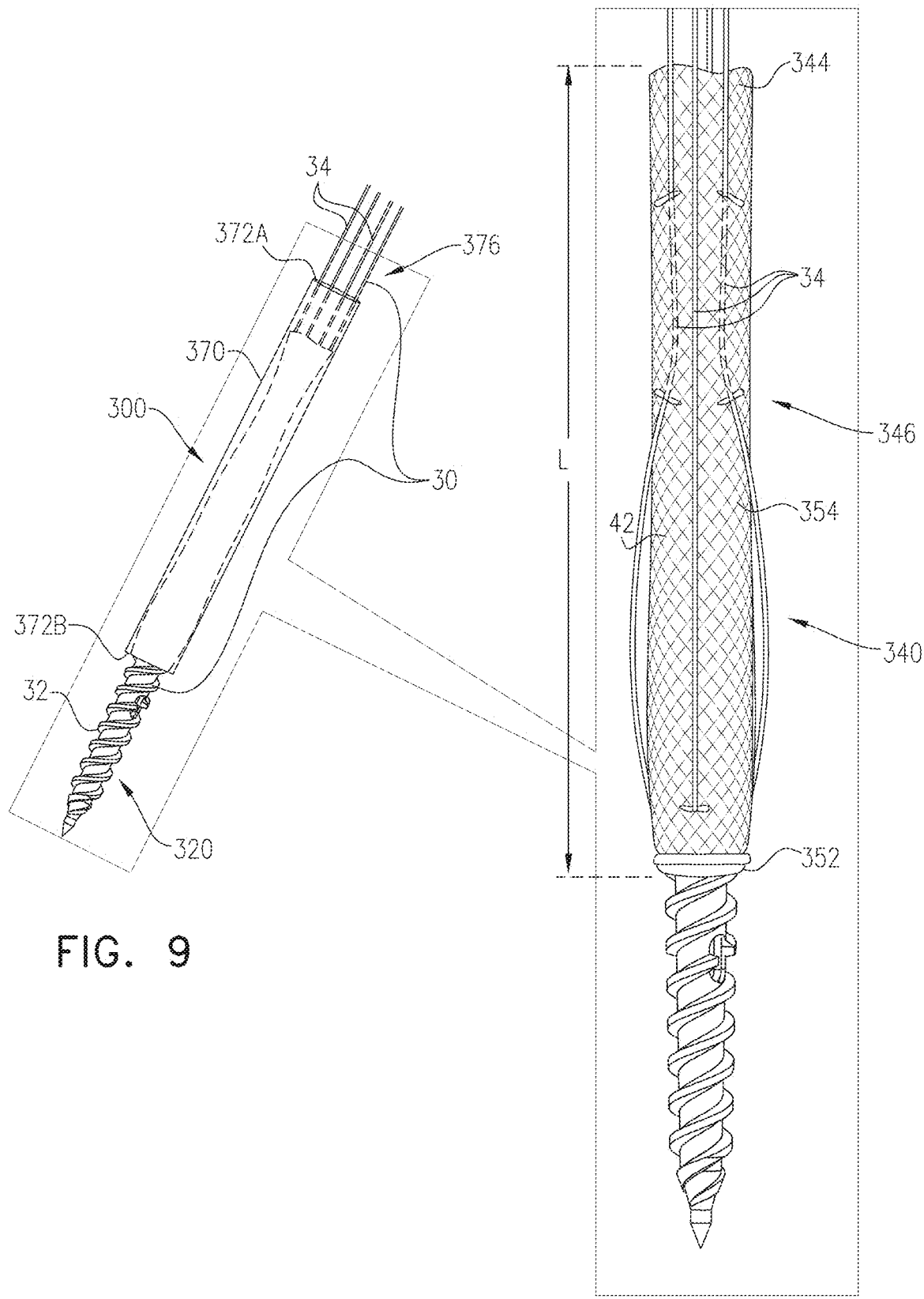
FIG. 9 is a schematic illustration of an implant system, according to some embodiments of the invention.

Reference is now made to FIG. 9, which is a schematic illustration of an implant system 300, in accordance with some embodiments of the present invention. Reference is also made to FIGS. 10A-H, which are schematic illustrations of a method for treating Hill-Sachs lesion 22 on humeral head 24 using implant system 300, in accordance with some embodiments of the present invention.

In some embodiments, implant system 300 comprises a bone-implant assembly 320, which may implement any of the features of bone-implant assembly 20, described hereinabove with reference to FIGS. 1 and 2, mutatis mutandis. Like reference numerals refer to like parts.

In some embodiments, bone-implant assembly 320 comprises, in addition to suture anchor 30, a bone-void filler implant 340, which may implement any of the features of bone-void filler implant 40, described hereinabove with reference to FIGS. 1 and 2, mutatis mutandis. In some embodiments, bone-void filler implant 340 has a proximal portion 344 that is slidably coupled to the one or more sutures 34, so as to be coupled to suture anchor 30, such as can be seen in the transition between FIGS. 10D and 10F. In some embodiments, bone-void filler implant 340 is configured to transition from an elongate, low-profile delivery configuration 346, labeled in FIGS. 9 and 10D-E, to a shortened radially-expanded deployment configuration 348 against humeral head 24, labeled in FIGS. 10G and 10H, upon distal sliding of proximal portion 344 of bone-void filler implant 340 along the one or more sutures 34 toward bone anchor 32, such as shown in FIG. 10F. In FIGS. 9 and 10A-10E bone-void filler implant 340 is in elongate, low-profile delivery configuration 346, as can best be seen in FIGS. 9, 10D, and 10E. In some embodiments, the surgeon's control over the extent of the transition to low-profile delivery configuration 346 provides control of how tightly bone-void filler implant 340 is pressed against humeral head 24.

In some embodiments, bone-void filler implant 340 is at least coupled to bone anchor 32, so as to be coupled to suture anchor 30. In some embodiments, for example, such as can be seen in FIG. 9, a distal portion 352 of bone-void filler implant 340 may be fixed to bone anchor 32 (in which case, a portion of bone-void filler implant 340 is introduced into Hill-Sachs lesion 22 as bone anchor 32 is introduced). In some embodiments, distal portion 352 of bone-void filler implant 340 is not fixed to bone anchor 32, and distally slides along the one or more sutures 34 toward bone anchor 32 as and/or after proximal portion 344 of bone-void filler implant 340 slides along the one or more sutures 34.

In some embodiments, alternatively or additionally, a distal portion of bone-void filler implant 340 is non-slidably fixed to the one or more sutures 34 (configuration not shown).

In some embodiments, bone-void filler implant 340 comprises a patch 354.

In some embodiments, patch 354 is arranged as tubular sleeve 356, such as shown in the figures. In some embodiments, either the material of tubular sleeve 356 comprises osteoconductive bone-filler material 42, or tubular sleeve 356 contains osteoconductive bone-filler material 42 within an internal space defined by the tubular sleeve.

In some embodiments, a length L of patch 354 is between 1 and 15 times, e.g., between 3 and 10 times, a width W of patch 354 (labeled in FIG. 9) when bone-void filler implant 340 is in elongate, low-profile delivery configuration 346. In some embodiments, alternatively or additionally, the length L of patch 354 is between 20 and 60 mm, such as 40 mm, and the width W of patch 354 is between 3 and 10 mm, such as 5 mm.

In some embodiments, bone-void filler implant 340 has a greatest lateral dimension $L_D$ of between 0.2 and 4 cm, such as between 1 and 3 cm, e.g., 1.35 cm, when in the shortened radially-expanded deployment configuration (labeled in FIGS. 10G and 10H).

In some embodiments, patch 354 is shaped so as to define at least first and second holes 358 and 360 therethrough between first and second surfaces 362A and 362B of patch 354 opposite each other, as labeled in FIG. 10F. In some embodiments, at least one of sutures 34 passes through first hole 358 in a direction 364A from first surface 362A to second surface 362B, and through second hole 360 in a direction 364B from second surface 362B to first surface 362A.

In some embodiments, patch 354 is configured, when in the shortened radially-expanded deployment configuration 348, to be accordion-pleated, such as shown in FIGS. 10F-H.

In some embodiments, patch 354 is configured to crumple during a transition from elongate, low-profile delivery configuration 346 to shortened radially-expanded deployment configuration 348.

In some embodiments, patch 354 thus may be considered a collapsing tower.

Reference is made to FIGS. 9 and 10A-10D. In some embodiments, implant system 300 system further comprises a delivery tube 370 having proximal and distal end openings 372A and 372B. In some embodiments, such as shown in FIG. 9, bone-implant assembly 320 is partially disposed within delivery tube 370 such that (a) at least a portion of bone anchor 32, (b) bone-void filler implant 340, and (c) respective distal portions of the one or more sutures 34 are disposed within delivery tube 370 with proximal portion 344 of bone-void filler implant 340 proximal to bone anchor 32. In some embodiments, respective proximal portions 376 of the one or more sutures 34 extend out of proximal end opening 372A of delivery tube 370.

In some embodiments, at least two longitudinal suture portions of the sutures 34 are loosely knotted together when bone-implant assembly 320 is partially disposed within delivery tube 370.

In some embodiments, delivery tube 370 has an external diameter of no more than 7 mm, such as no more than 6 mm, e.g., no more than 5 mm.

Reference is made to FIGS. 10A-10H. In some embodiments of the present invention, a method is provided for treating Hill-Sachs lesion 22 on humeral head 24.

As show in FIGS. 10A-10B, bone anchor 32 of suture anchor 30 of bone-implant assembly 20 is implanted in Hill-Sachs lesion 22 on humeral head 24, such that one or more sutures 34 fixed to bone anchor 32 extend proximally from bone anchor 32 out of Hill-Sachs lesion 22.

In some embodiments, such as shown in FIG. 10B, bone anchor 32 is implanted in Hill-Sachs lesion 22 while at least a portion of bone-void filler implant 40 is disposed outside Hill-Sachs lesion 22.

In some embodiments, such as shown in FIG. 10B, bone anchor 32 is implanted in Hill-Sachs lesion 22 while at least a portion of bone-void filler implant 40 is disposed within Hill-Sachs lesion 22.

As shown in FIGS. 10D-10G, at least a portion of bone-void filler implant 40 of bone-implant assembly 20 is advanced over the one or more sutures 34 toward implanted bone anchor 32, such that bone-void filler implant 40 at least partially fills Hill-Sachs lesion 22.

In some embodiments, optionally, as shown in FIGS. 10D-10G, advancing bone-void filler implant 40 over the one or more sutures 34 toward implanted bone anchor 32 comprises transitioning bone-void filler implant 40 from elongate, low-profile delivery configuration 346 to shortened radially-expanded deployment configuration 348 against humeral head 24, by distally sliding proximal portion 344 of bone-void filler implant 40 along the one or more sutures 34 toward implanted bone anchor 32.

In some embodiments, optionally, as shown in FIG. 10G-10H, after bone-void filler implant 40 has been advanced toward implanted bone anchor 32, bone-void filler implant 40 is tied down using the one or more sutures 34. In some embodiments, optionally, tying down bone-void filler implant 40 using the one or more sutures 34 compresses bone-void filler implant 40 against humeral head 24.

In some embodiments, optionally, as shown in FIGS. 10G-10H, after bone-void filler implant 40 has been advanced toward implanted bone anchor 32, at least two longitudinal suture portions of the one or more sutures 34 are knotted together.

Figure 11E:
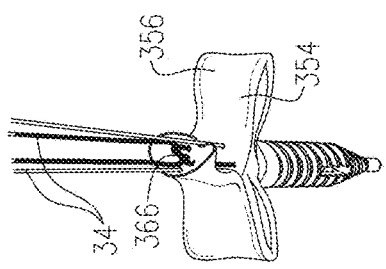
FIGS. 11A, 11B, 11C, 11D, 11E, 11F, 11G and 11H are schematic illustrations of a configuration of a bone-implant assembly and a method of knotting suture portions thereof, according to some embodiments of the invention.
Figure 11D:
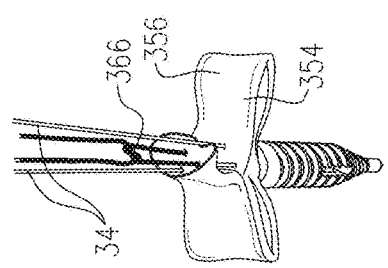
Figure 11C:
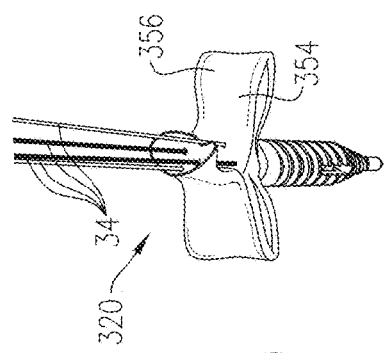
Figure 11H:
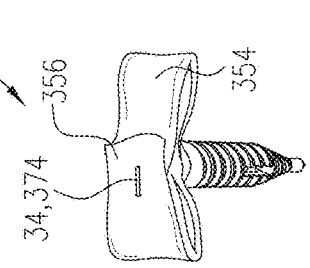

Reference is now made to FIGS. 11A-11H, which are schematic illustrations of a configuration of bone-implant assembly 320 and a method of knotting suture portions thereof, in accordance with some embodiments of the present invention. In some embodiments, patch 354 and the one or more sutures 34 are arranged such that one or more knots 366 formed upon knotting together of two or more longitudinal suture portions of the one or more sutures 34 together are covered by patch 354, such as shown in FIG. 11H. In some embodiments, in which patch 354 is arranged as tubular sleeve 356, tubular sleeve 356 and the one or more sutures 34 are arranged such that the one or more knots 366 formed upon the knotting together of the two or more longitudinal suture portions of the one or more sutures 34 are within a proximal portion 368 of tubular sleeve 356 (labeled in FIG. 11G), such that the one or more knots 366 are covered by tubular sleeve 356 of patch 354. It is noted that one or more longitudinal suture portions 374 of the two or more longitudinal suture portions of one or more sutures 34 may be disposed outside tubular sleeve 356, such as passing out of the sleeve and back in the sleeve, such as shown in FIG. 11H.

In some embodiments, the knotting method shown in FIGS. 11A-11H is performed after advancing bone-void filler implant 40 toward the implanted bone anchor 32, such as described hereinabove with reference to FIGS. 10A-10F. In some embodiments, the knotting method may optionally be performed at the steps of the method described hereinabove with reference to FIGS. 10G-10H, at which two or more longitudinal suture portions of the one or more sutures 34 are knotted together.

In some embodiments, in the knotting method shows in FIGS. 11A-11H, the two or more longitudinal suture portions of the one or more sutures 34 are knotted together by making one or more knots 366 (e.g., two or more knots 366, such as exactly two knots 366), such as shown in FIGS. 11D-11G, such that the one or more knots 366 are covered by the patch 354, such as shown in FIG. 11H.

In some embodiments, the method further comprises, after making the one or more knots 366, cutting off excess portions of the two or more longitudinal suture portions such that proximal ends of the two or more longitudinal suture portions are covered by patch 354.

Figure 11G:
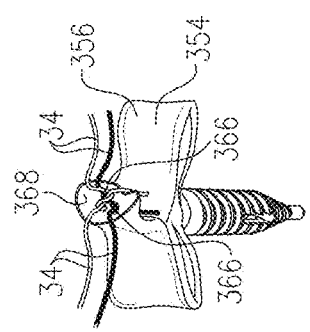
Figure 11F:
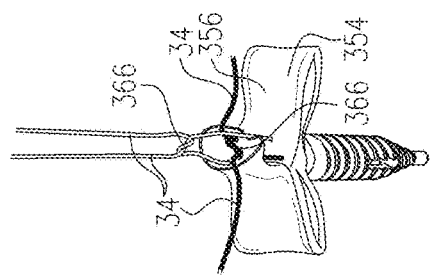
Figure 11B:
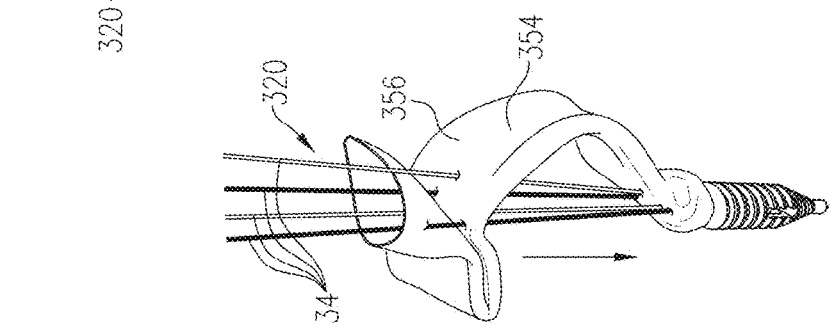
Figure 11A:
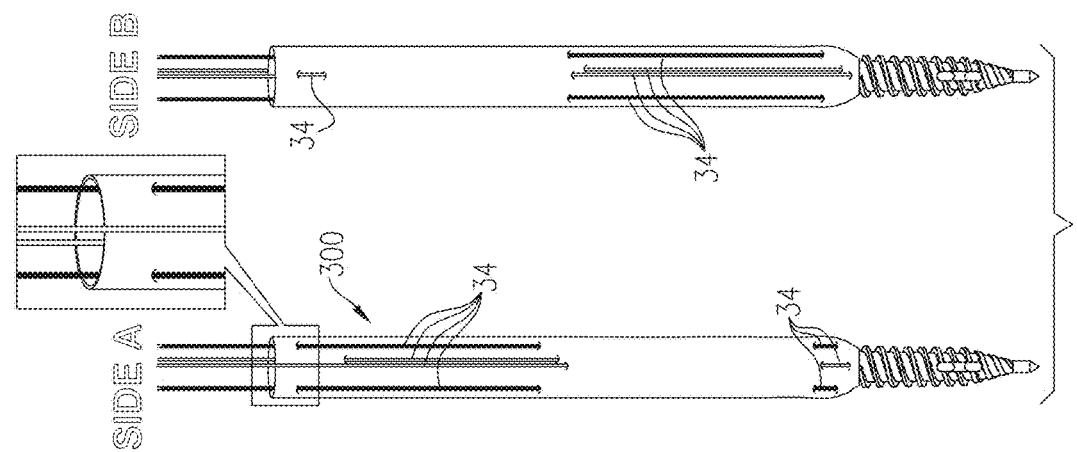

In some embodiments, in which patch 354 is arranged as tubular sleeve 356, the one or more knots 366 are made within proximal portion 368 of tubular sleeve 356, such as shown in FIG. 11G, such that the one or more knots 366 are covered by tubular sleeve 356 of the patch 354, such as shown in FIG. 11H.

In some embodiments, optionally, a knot pusher may be used for the knotting, such as a knot pusher commercially available from Anthrex, Inc. (Naples, Fla., USA).

Reference is now made to FIGS. 12A-12B, which are schematic illustrations of a bone-implant assembly 720 for treating a Bankart lesion 702, in accordance with some embodiments of the present invention. As is known in the art, a Bankart lesion 702 it can present a detachment of an anteroinferior labrum 704 from a glenoid rim 706.

Figure 13A:
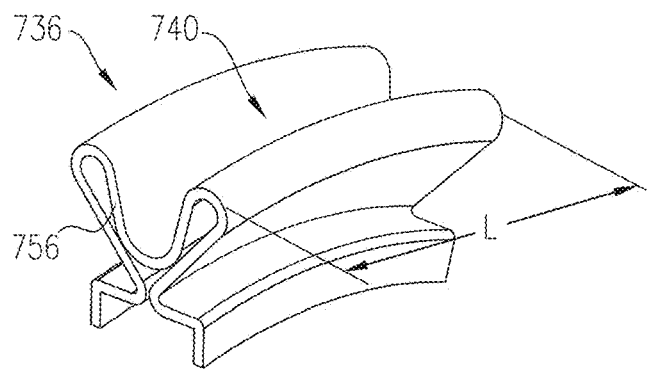
FIGS. 13A and 13B are schematic illustrations of an elongate labrum receptacle of the bone-implant assembly of FIGS. 12A-B, according to some embodiments of the invention.
Figure 13B:
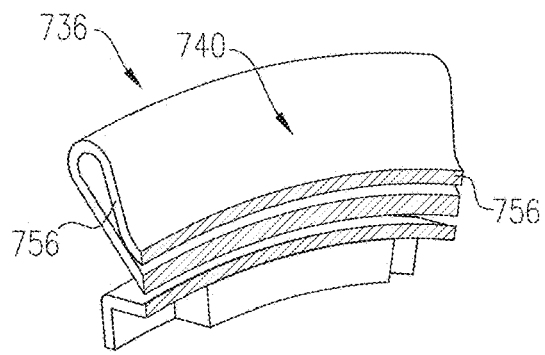

Reference is also made to FIGS. 13A and 13B, which are schematic illustrations of an elongate labrum receptacle 736 of bone-implant assembly 720, in accordance with some embodiments of the present invention.

Figure 14:
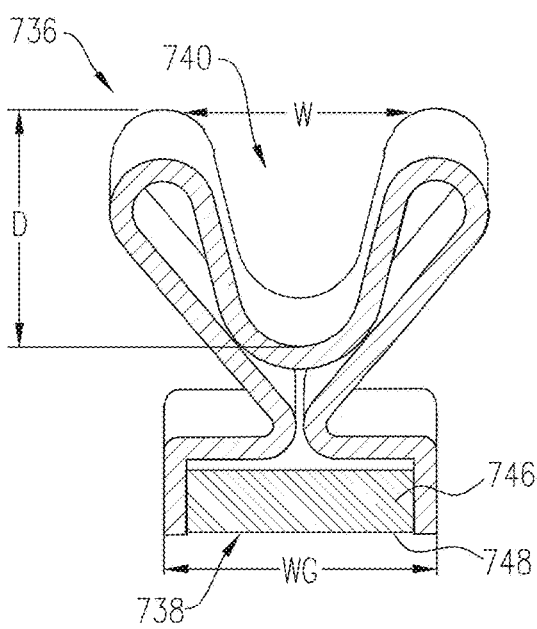
FIG. 14 is a schematic cross-sectional illustration of the elongate labrum receptacle of the bone-implant assembly of FIGS. 12A-B, according to some embodiments of the invention.

Reference is further made to FIG. 14, which is a schematic cross-sectional illustration of elongate labrum receptacle 736, in accordance with some embodiments of the present invention.

Figure 15A:
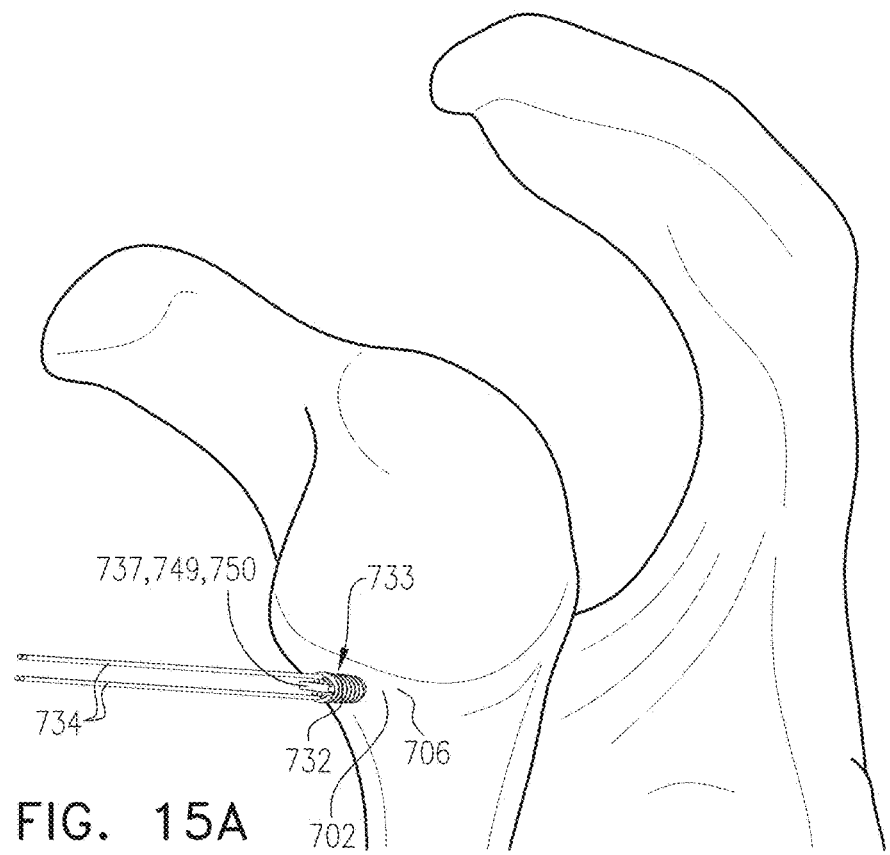
FIGS. 15A, 15B, 15C, 15D, 15E and 15F are schematic illustrations of a method for treating a Bankart lesion, according to some embodiments of the invention.
Figure 15B:
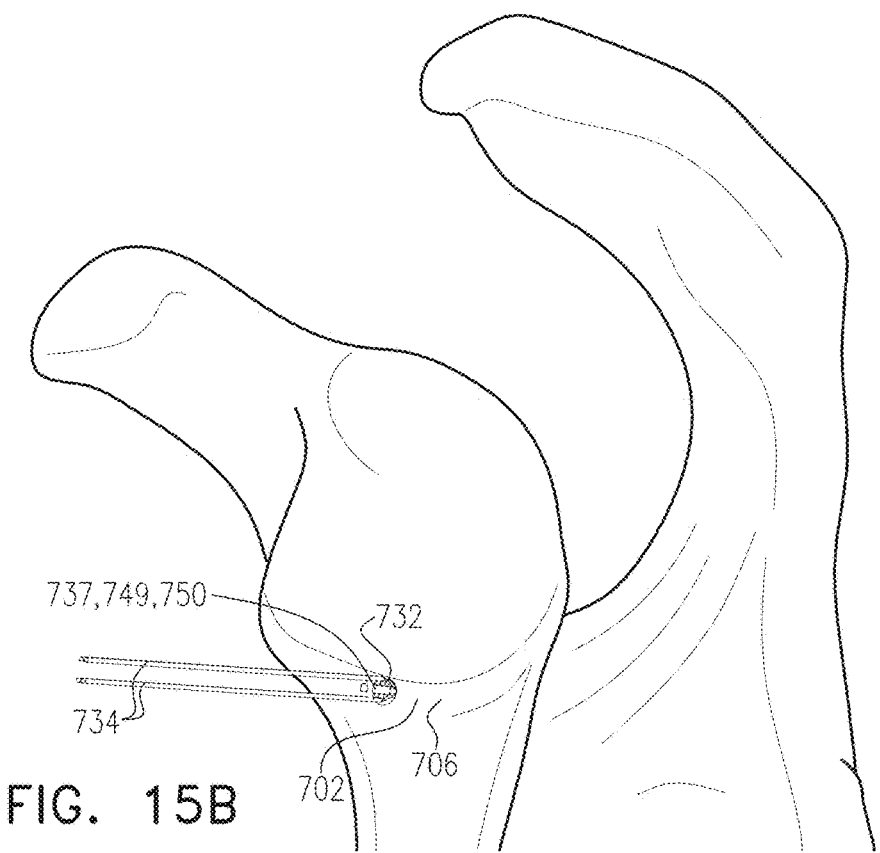
Figure 15C:
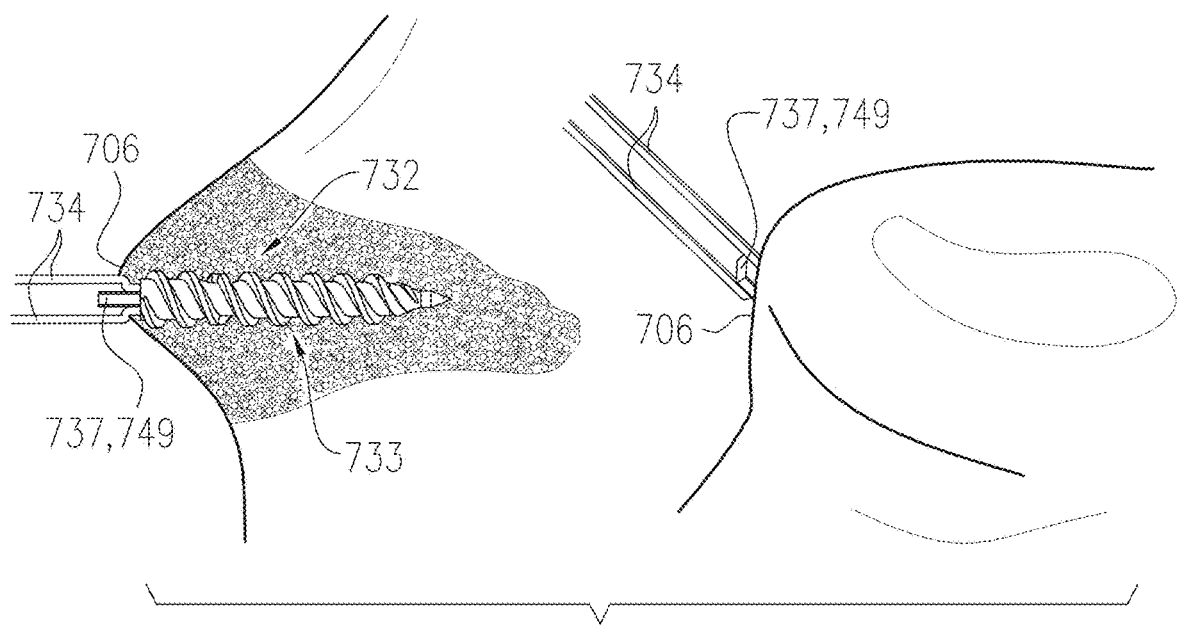
Figure 15D:
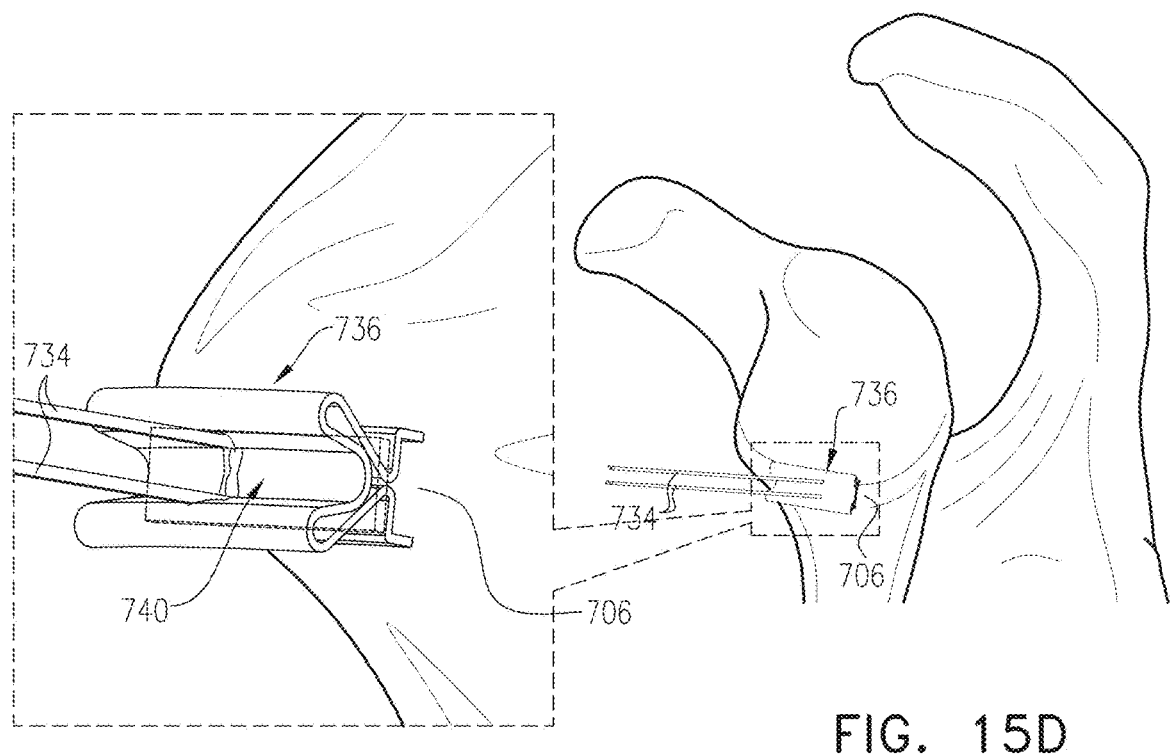
Figure 15E:
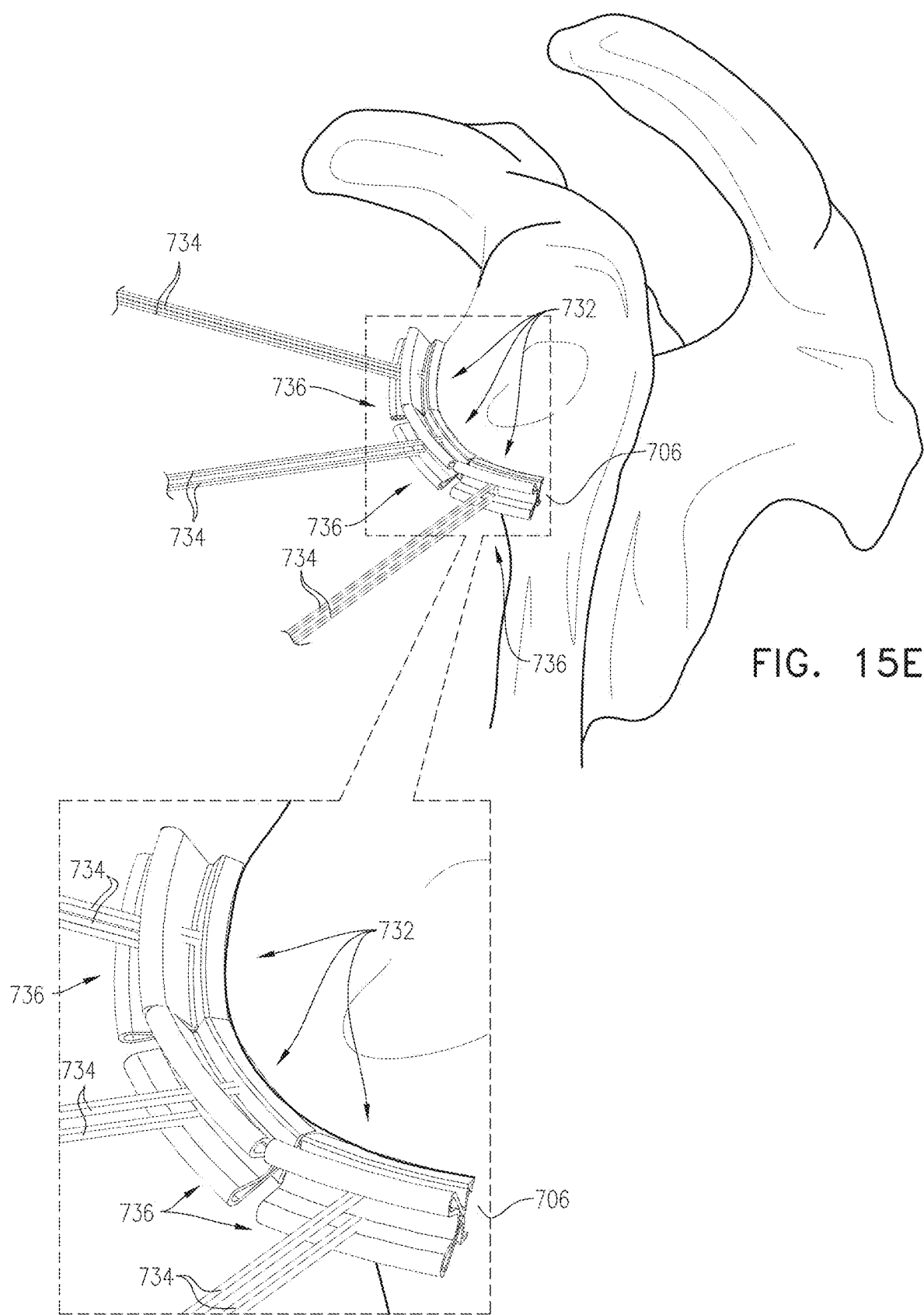
Figure 15F:
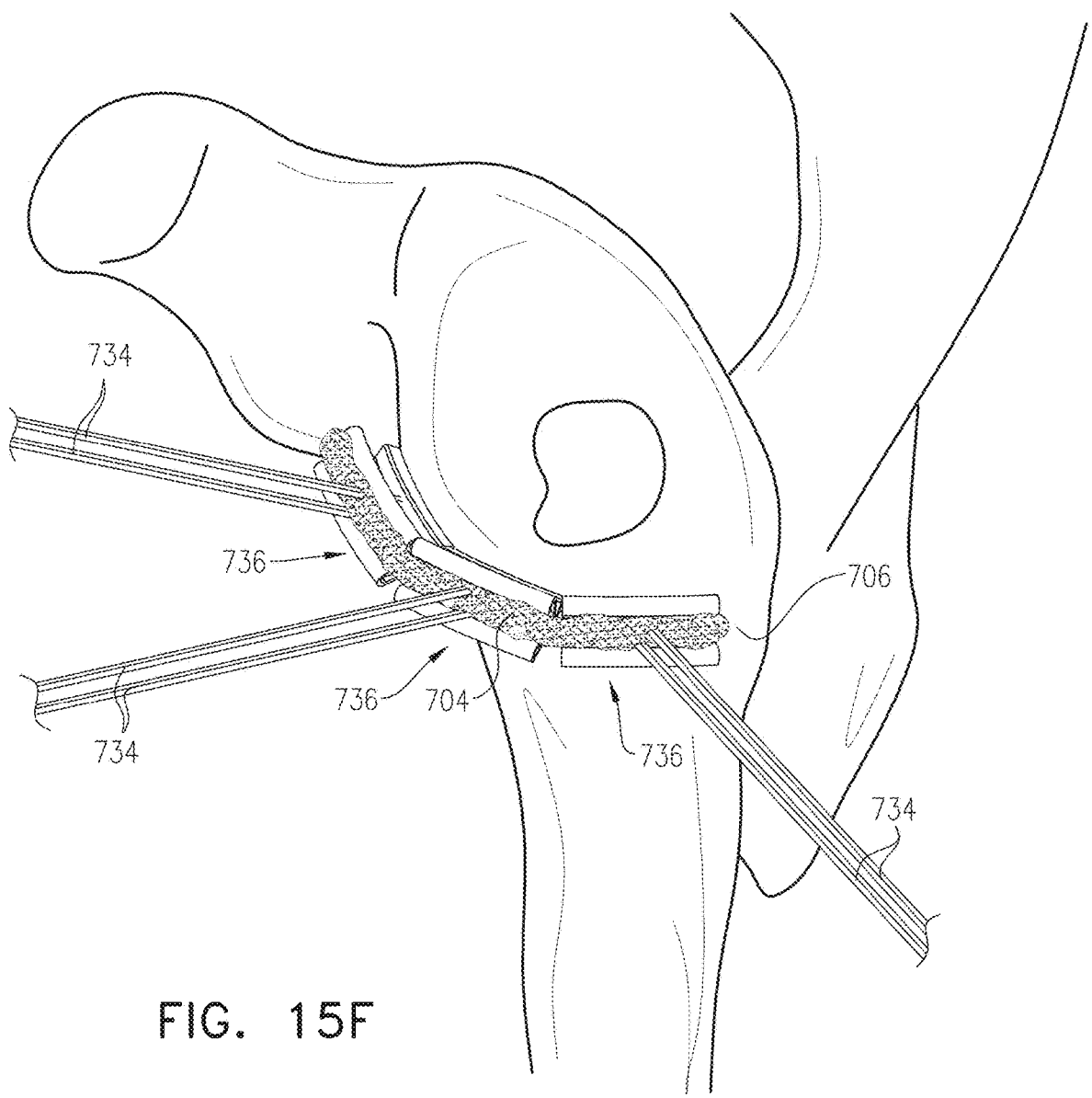

In some embodiments, bone-implant assembly 720 comprises:

a bone anchor 732, which is shaped so as to define a distal portion 733 configured to be implanted in glenoid rim 706; and elongate labrum receptacle 736, which is shaped so as to define (a) a distal glenoid-facing surface 738 and (b) a proximal trough 740 that (i) faces proximally away from distal glenoid-facing surface 738 and (ii) is shaped so as to receive detached anteroinferior labrum 704, such as shown in FIG. 15F.

As used in the present application, including in the claims, a "trough" is any long depression or hollow, as between two ridges or waves.

In some embodiments, elongate labrum receptacle 736 is configured to be coupled to a proximal portion 737 of bone anchor 732 such that (a) distal glenoid-facing surface 738 rests against glenoid rim 706 and (b) proximal trough 740 faces proximally away from glenoid rim 706, toward detached anteroinferior labrum 704, in order to receive detached anteroinferior labrum 704.

In some embodiments, bone-implant assembly 720 further comprises one or more sutures 734 fixed to and extending proximally from proximal portion 737 of bone anchor 732. In some embodiments, the one or more sutures 734 pass through distal glenoid-facing surface 738 of elongate labrum receptacle 736 and, optionally, proximal trough 740. In some embodiments, elongate labrum receptacle 736 is advanceable over the one or more sutures 734 to proximal portion 737 of bone anchor 732.

As can be seen in FIG. 12A, in some embodiments, distal glenoid-facing surface 738 is shaped so as to define one or more openings 744 through which the one or more sutures 734 pass. In some embodiments, optionally, each of the one or more openings 744 has a cross-sectional area of between 0.04 and 1.5 mm2, such as been 0.04 and 1 mm2, e.g., 1 mm2. In some embodiments, optionally, the one or more openings 744 are open to an edge of distal glenoid-facing surface 738, such as shown. In some embodiments, alternatively, the one or more openings 744 are positioned away from the edge (configuration not shown).

In some embodiments, distal glenoid-facing surface 738 of elongate labrum receptacle 736 is shaped so as to define exactly two openings 744 through which the one or more sutures 734 pass, and each of the exactly two openings 744 has a cross-sectional area of between 0.2 and 10 mm2.

In some embodiments, in which the one or more sutures 734 also pass through proximal trough 740, proximal trough 740 is shaped so as to define one or more openings through which the one or more sutures 734 pass; during manufacture, these openings may be made either before the sutures are passed through the openings, or may be made as the sutures are passed through (for example, for configurations in which proximal trough 740 comprises a flexible material such as a textile).

In some embodiments, two or more longitudinal suture portions 735 of the one or more sutures 734 are configured to be knotted together when passing through distal glenoid-facing surface 738 of elongate labrum receptacle 736, so as to couple elongate labrum receptacle 736 to proximal portion 737 of bone anchor 732.

In some embodiments, such as shown in FIGS. 12A-12B and 14, elongate labrum receptacle 736 further comprises a rigid base frame 746, which at least partially defines distal glenoid-facing surface 738. In some embodiments, a distal surface 748 of rigid base frame 746 defines at least a portion of distal glenoid-facing surface 738 of the elongate labrum receptacle 736, i.e., distal surface 748 of rigid base frame 746 is exposed distally. In some embodiments, alternatively or additionally, elongate labrum receptacle 736 comprises a material more flexible than the material of rigid base frame 746. In some embodiments, this material defines distal glenoid-facing surface 738. In some embodiments, rigid base frame 746 at least partially defines distal glenoid-facing surface 738 by providing structure to the more flexible material.

In some embodiments, proximal trough 740 is more flexible than rigid base frame 746.

In some embodiments, as can be seen in FIG. 12A, proximal portion 737 of bone anchor 732 is shaped so as to define an anchor head 749. In some embodiments, one of anchor head 749 and rigid base frame 746 is shaped so as to define at least one protrusion 750. In some embodiments, the other of anchor head 749 and rigid base frame 746 is shaped so as to define at least one protrusion receptacle 752 configured to receive the at least one protrusion 750 so as to prevent rotation of elongate labrum receptacle 736 with respect to bone anchor 732 when elongate labrum receptacle 736 is coupled to proximal portion 737 of bone anchor 732. In some embodiments, protrusion receptacle 752 may be an indentation or an aperture. In some embodiments, by way of example, in the configuration shown in FIGS. 12A-12B, anchor head 749 is shaped so as to define the at least one protrusion 750 that protrudes proximally from anchor head 749, and rigid base frame 746 is shaped so as to define the at least one protrusion receptacle 752.

In some embodiments, protrusion receptacle 752 has a cross-sectional area of between 0.2 and 10 mm2, such as between 0.5 and 5 mm2, e.g., 2.25 mm2.

In some embodiments, the at least one protrusion 750 and the at least one protrusion receptacle 752 are non-circular. In some embodiments, for example, the at least one protrusion receptacle 752 may be shaped as respective slots or elongate indentations, both of which may or may not be rectangular.

In some embodiments, in which protrusion receptacle 752 is rectangular, a length of the long side is between 0.5 and 5 mm, and a length of the short side is between 0.4 and 2 mm.

In some embodiments, elongate labrum receptacle 736 does not comprise rigid base frame 746 (not shown for bone-implant assembly 720, but similar to the configuration of bone-implant assembly 820 described hereinbelow with reference to FIGS. 16-19C, mutatis mutandis). In some embodiments, one of anchor head 749 and distal glenoid-facing surface 738 of elongate labrum receptacle 736 is shaped so as to define at least one protrusion. In some embodiments, the other of anchor head 749 and distal glenoid-facing surface 738 of elongate labrum receptacle 736 is shaped so as to define at least one protrusion receptacle configured to receive the at least one protrusion so as to prevent rotation of elongate labrum receptacle 736 with respect to bone anchor 732 when elongate labrum receptacle 736 is coupled to bone anchor 732.

In some embodiments, the at least one protrusion and the at least one protrusion receptacle are non-circular. In some embodiments, for example, the at least one protrusion receptacle may be shaped as respective slots or elongate indentations.

In some embodiments, proximal trough 740 extends along an entire length L of elongate labrum receptacle 736 and is open at both ends 756 of elongate labrum receptacle 736 (labeled in FIGS. 13A and 13B). In some embodiments, optionally, proximal trough 740 has a constant depth D (labeled in FIG. 14) along the entire length L of elongate labrum receptacle 736.

In some embodiments, proximal trough 740 has one or more of the following dimensions:
- a length L of between 0.5 and 2 cm, such as between 0.5 and 1.5 cm, e.g., 1 cm,
- a greatest width W of between 1 and 10 mm, such as between 2 and 8 mm, and/or
- a depth D of between 1 and 10 mm, such as between 1.5 and 5 mm, e.g., 2.5 mm.

In some embodiments, distal glenoid-facing surface 738 of elongate labrum receptacle 736 has a greatest width $W_G$ of between 1 and 12 mm, such as between 3 and 8 mm.

In some embodiments, proximal trough 740 comprises a textile. For some applications, the textile is porous.

In some embodiments, proximal trough 740 is flexible.

Reference is now made to FIGS. 15A-15F, which are schematic illustrations of a method for treating Bankart lesion 702, in accordance with some embodiments of the present invention.

In some embodiments, as shown in FIGS. 15A-15C, distal portion 733 of bone anchor 732 is implanted in glenoid rim 706. In some embodiments, optionally, as shown in FIGS. 15A-15B, one or more sutures 734 of bone-implant assembly 720 are fixed to and extend proximally from proximal portion 737 of bone anchor 732.

In some embodiments, as shown in FIG. 15D, elongate labrum receptacle 736 is coupled to proximal portion 737 of bone anchor 732 such that distal glenoid-facing surface 738 of elongate labrum receptacle 736 rests against glenoid rim 706 and proximal trough 740 of elongate labrum receptacle 736 faces proximally away from distal glenoid-facing surface 738 and glenoid rim 706, toward the detached anteroinferior labrum 704 (not visible in FIG. 15C, but shown in FIG. 15F, described hereinbelow).

In some embodiments, such as shown in FIG. 15D, two or more longitudinal suture portions 735 of the one or more sutures 734 are knotted together when passing through distal glenoid-facing surface 738 of elongate labrum receptacle 736, so as to couple elongate labrum receptacle 736 to proximal portion 737 of bone anchor 732.

FIG. 15E is described hereinbelow.

In some embodiments, as shown in FIG. 15F, detached anteroinferior labrum 704 is inserted into proximal trough 740 of elongate labrum receptacle 736.

In some embodiments, optionally, anteroinferior labrum 704 is sutured to proximal trough 740, typically using the one or more sutures 734. In some embodiments, alternatively, anteroinferior labrum 704 is sutured to proximal trough 740 using additional sutures, or is not sutured to proximal trough 740.

Reference is made to FIG. 15E. In some embodiments, bone-implant assembly 720 comprises a plurality of bone anchors 732. In some embodiments, bone-implant assembly 720 additionally comprises a plurality of elongate labrum receptacles 736, each of which is configured to be coupled to at least one of bone anchors 732. In some embodiments, for example, bone-implant assembly 720 may comprise the same number of bone anchors 732 and elongate labrum receptacles 736, such as shown in FIG. 15E.

Reference is again made to FIGS. 15A-15F. In some embodiments, a method is provided for treating Bankart lesion 702 characterized by detachment of anteroinferior labrum 704 from glenoid rim 706.

In some embodiments, as shown in FIGS. 15A-C, distal portion 733 of bone anchor 732 is implanted in glenoid rim 706.

In some embodiments, as shown in FIG. 15D, elongate labrum receptacle is coupled to proximal portion 737 of bone anchor 732 such that distal glenoid-facing surface 738 of elongate labrum receptacle 736 rests against glenoid rim 706 and proximal trough 740 of elongate labrum receptacle 736 faces proximally away from distal glenoid-facing surface 738 and glenoid rim 706, toward detached anteroinferior labrum 704.

In some embodiments, such as shown in FIG. 15D, elongate labrum receptacle 736 is coupled to proximal portion 737 of bone anchor 732 by advancing elongate labrum receptacle 736 over the one or more sutures 734 to proximal portion 737 of bone anchor 732. In some embodiments, optionally, elongate labrum receptacle 736 is coupled to proximal portion 737 of bone anchor 732 by knotting together two or more longitudinal suture portions 735 of the one or more sutures 734. In some embodiments, for example, a knot pusher may be used for the knotting, such as a knot pusher commercially available from Anthrex, Inc. (Naples, Fla., USA).

In some embodiments, such as shown in FIG. 15E, a plurality of distal portions 733 of a respective plurality of bone anchors 732 are implanted in glenoid rim 706. In some embodiments, such as shown in FIG. 15E, each of a plurality of elongate labrum receptacles 736 is coupled to proximal portion 737 of at least one of bone anchors 732.

In some embodiments, as shown in FIG. 15F, detached anteroinferior labrum 704 is inserted into proximal trough 740. In some embodiments, optionally, detached anteroinferior labrum 704 is sutured to proximal trough 740 using the one or more sutures 734.

Figure 16:
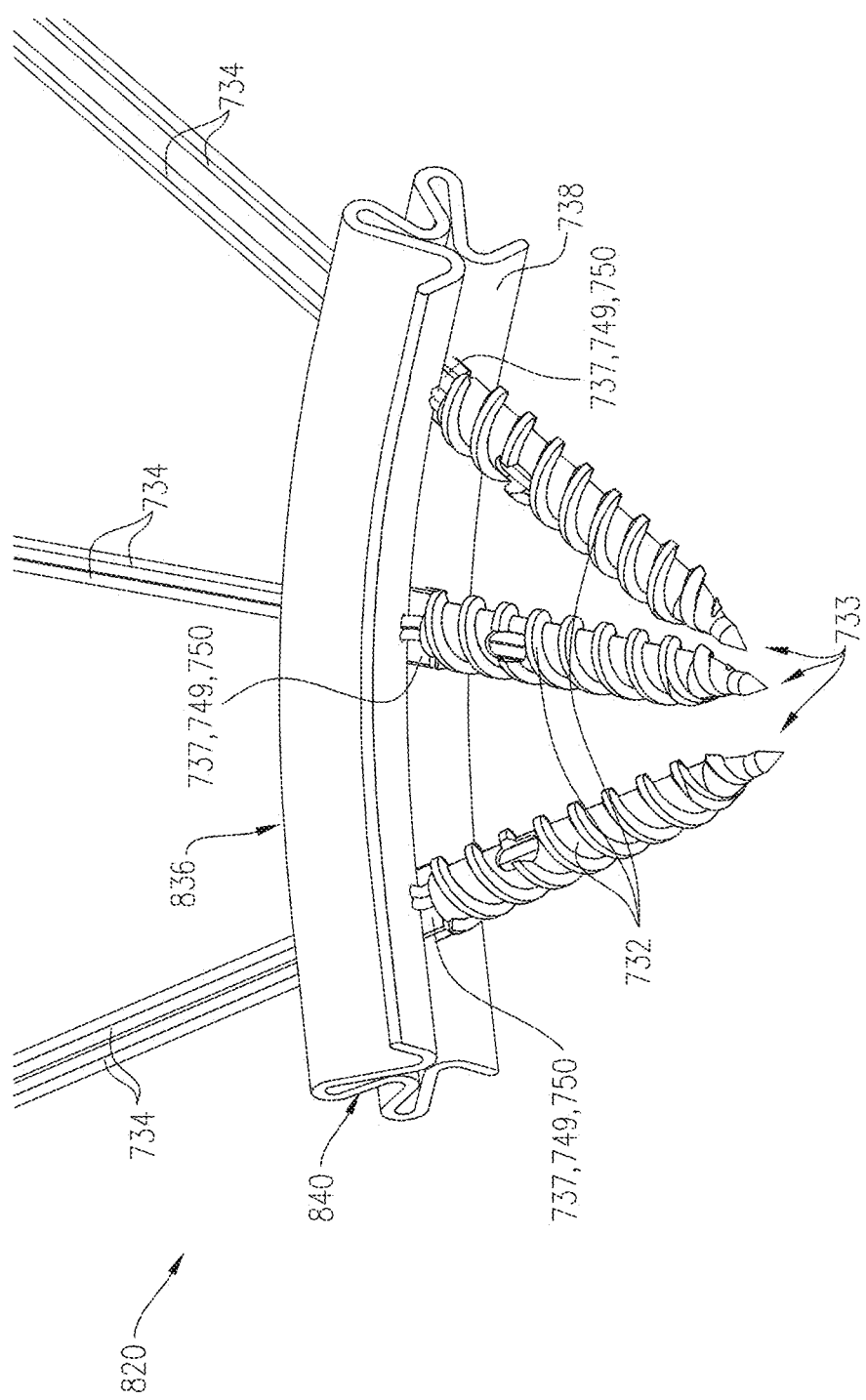
FIG. 16 is a schematic illustration of another bone-implant assembly for treating a Bankart lesion, according to some embodiments of the invention.

Reference is now made to FIG. 16, which is a schematic illustration of a bone-implant assembly 820 for treating Bankart lesion 702, in accordance with some embodiments of the present invention. In some embodiments, other than as described below, bone-implant assembly 820 is similar to bone-implant assembly 720, described hereinabove with reference to FIGS. 12A-15F, and may implement any of the features thereof, mutatis mutandis. Like reference numerals refer to like parts.

Figure 17A:
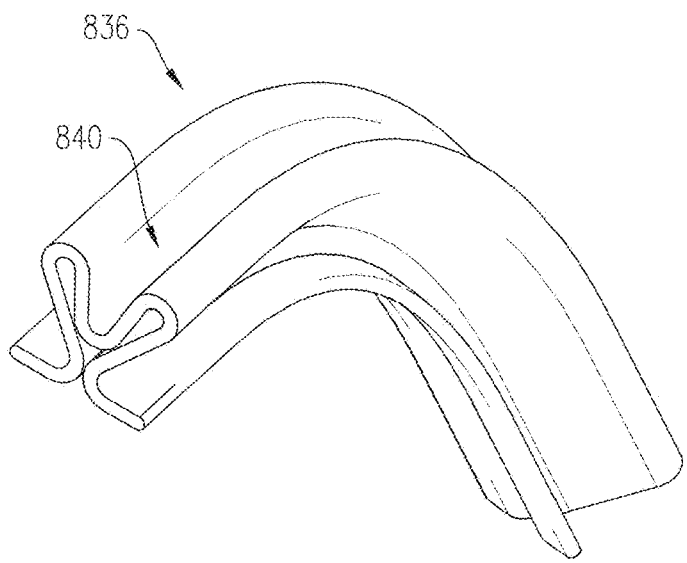
FIGS. 17A and 17B are schematic illustrations of an elongate labrum receptacle of the bone-implant assembly of FIG. 16, according to some embodiments of the invention.
Figure 17B:
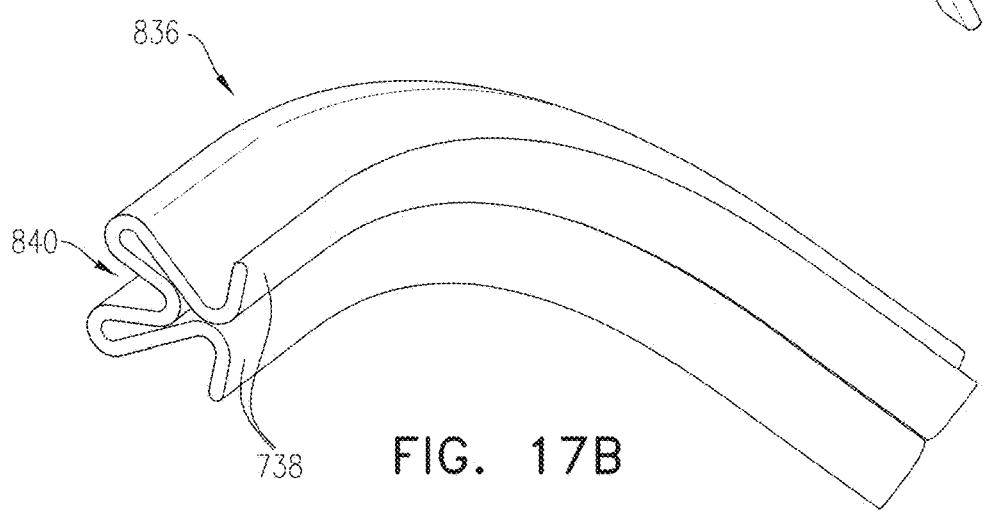

Reference is also made to FIGS. 17A and 17B, which are schematic illustrations of an elongate labrum receptacle 836 of bone-implant assembly 820, in accordance with some embodiments of the present invention. In some embodiments, other than as described below, elongate labrum receptacle 836 is similar to elongate labrum receptacle 736, described hereinabove with reference to FIGS. 12A-15F, and may implement any of the features thereof, mutatis mutandis.

Figure 18:
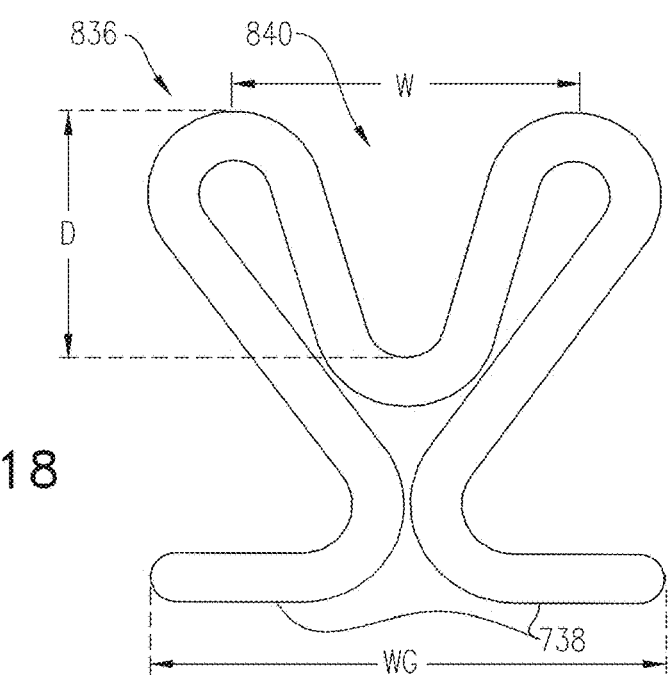
FIG. 18 is a schematic cross-sectional illustration of the elongate labrum receptacle of the bone-implant assembly of FIG. 16, according to some embodiments of the invention.

Reference is further made to FIG. 18, which is a schematic cross-sectional illustration of elongate labrum receptacle 836, in accordance with some embodiments of the present invention.

In some embodiments, bone-implant assembly 820 comprises:
 a plurality of bone anchors 732, which are shaped so as to define respective distal portions 733 configured to be implanted in glenoid rim 706; and
 elongate labrum receptacle 836, which is shaped so as to define (a) a distal glenoid-facing surface 838 and (b) a proximal trough 840 that (i) faces proximally away from distal glenoid-facing surface 838 and (ii) is shaped so as to receive detached anteroinferior labrum 704.

Figure 19A:
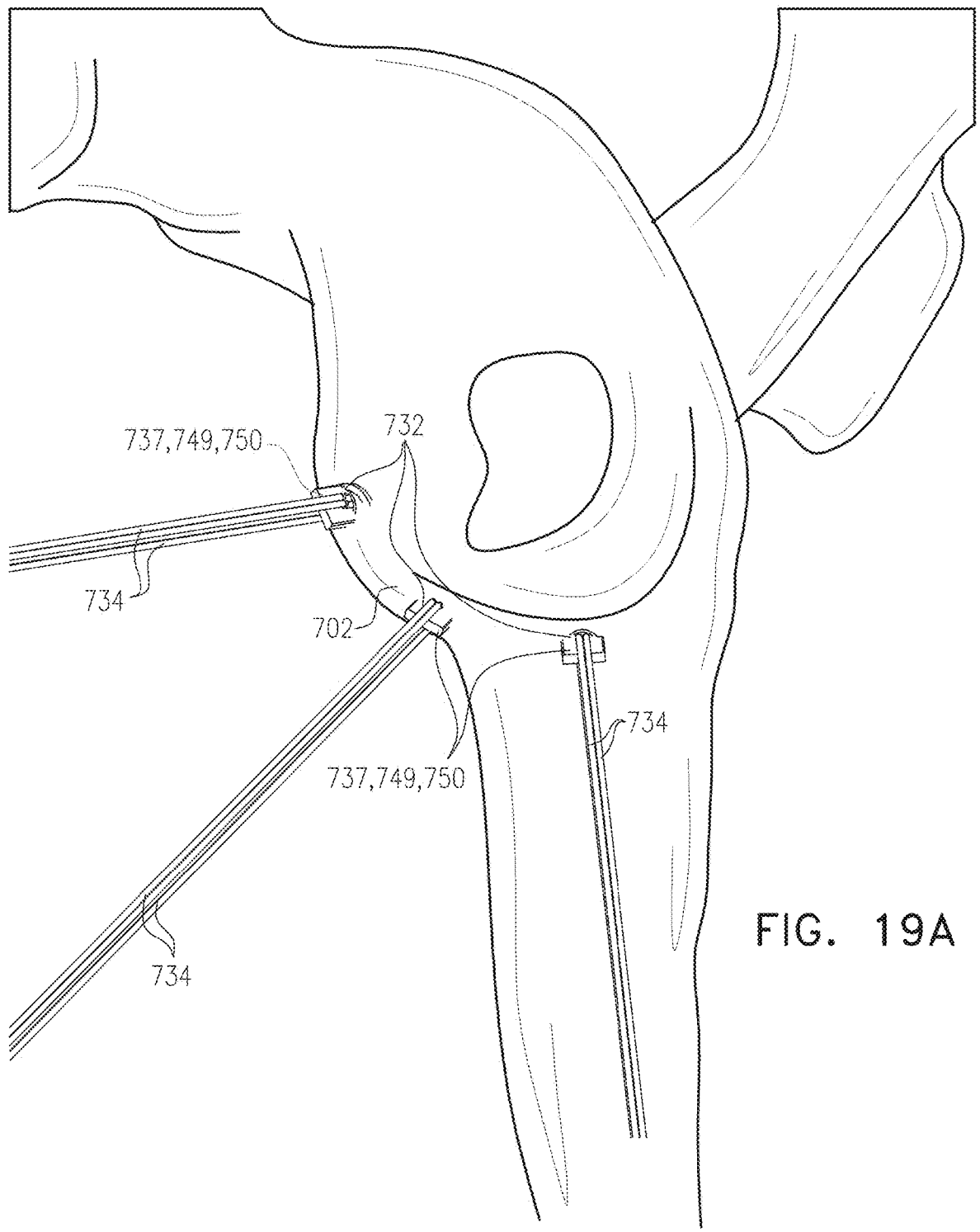
FIGS. 19A, 19B, 19C and 19D are schematic illustrations of a method for treating a Bankart lesion, according to some embodiments of the invention.
Figure 19B:
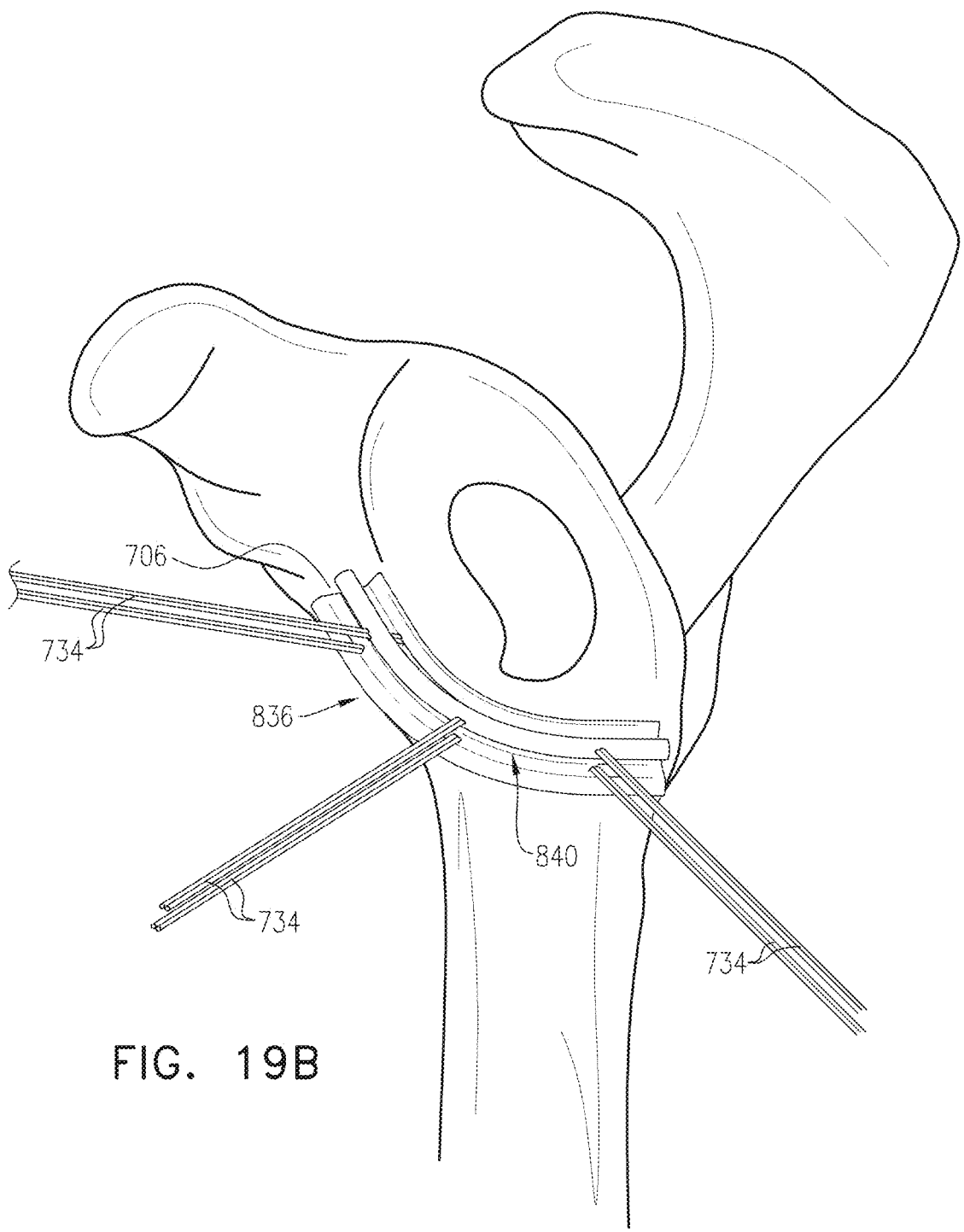
Figure 19C:
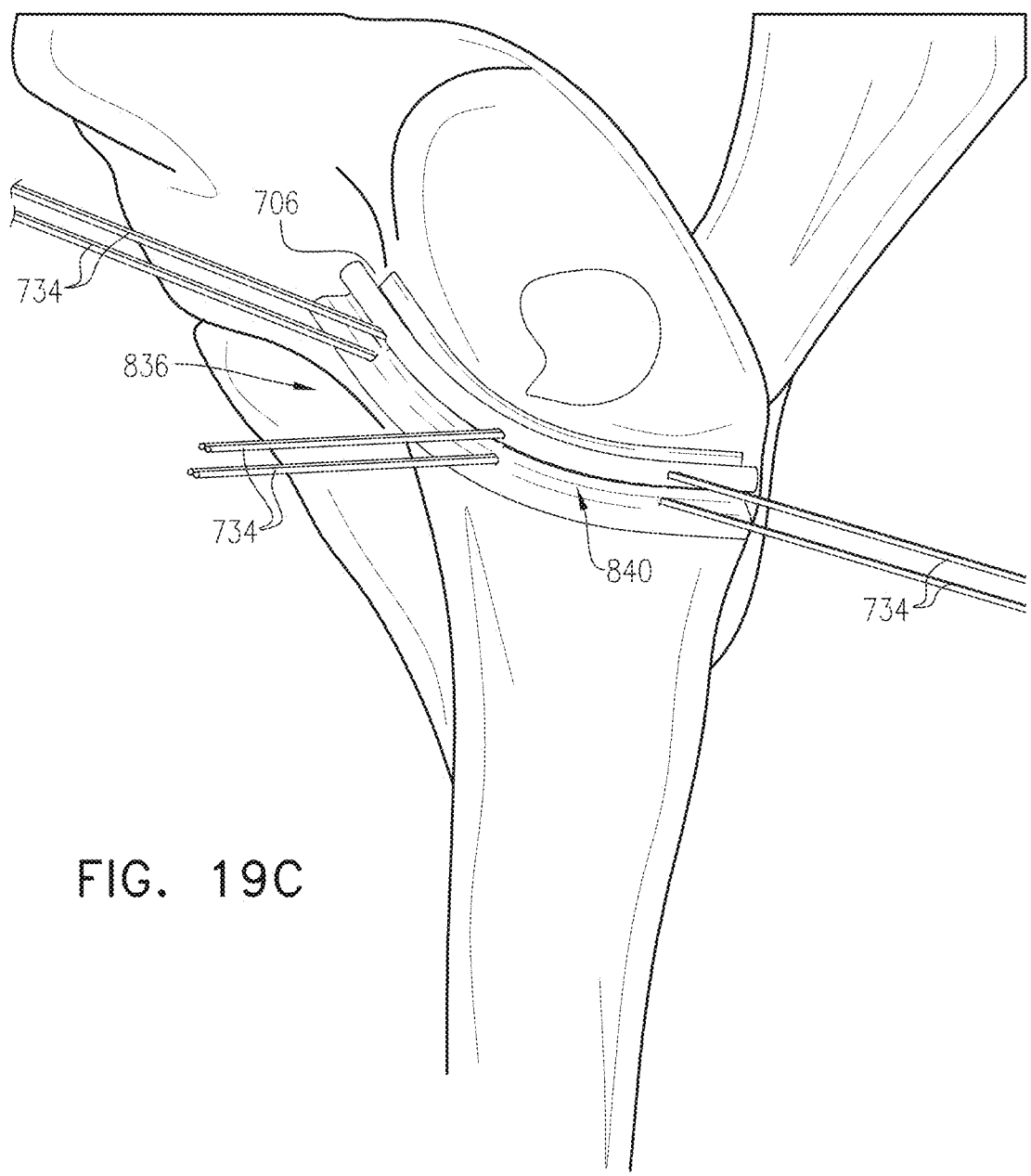
Figure 19D:
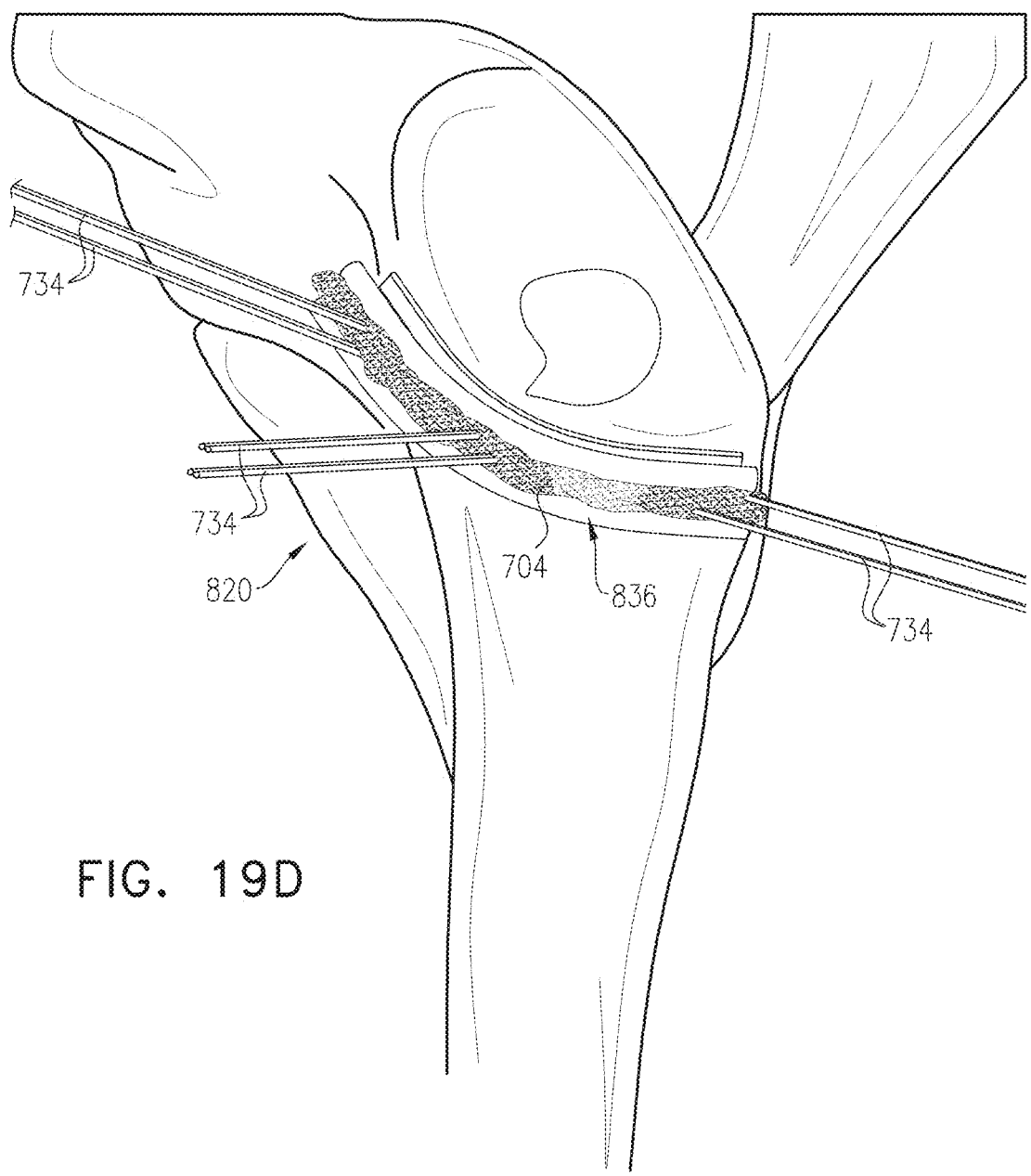

In some embodiments, elongate labrum receptacle 836 is configured to be coupled to respective proximal portions 737 of at least two of the plurality of bone anchors 732 such that (a) distal glenoid-facing surface 838 rests against glenoid rim 706 and (b) proximal trough 840 faces proximally away from glenoid rim 706, toward detached anteroinferior labrum 704, in order to receive detached anteroinferior labrum 704, such as shown in FIG. 19D.

In some embodiments, bone-implant assembly 820 further comprises a plurality of sutures 734 fixed to and extending proximally from proximal portions 737 of bone anchors 732, respectively. In some embodiments, sutures 734 pass through distal glenoid-facing surface 838 of elongate labrum receptacle 836, through proximal trough 840, or through both distal glenoid-facing surface 838 and proximal trough 840. In some embodiments, optionally, material of distal glenoid-facing surface 838 of elongate labrum receptacle 836 is not pre-shaped do define openings; instead, the openings are formed as the sutures 734 are penetrated through the material during manufacture. In some embodiments, elongate labrum receptacle 836 is advanceable over sutures 734 to proximal portions 737 of bone anchors 732, respectively.

In some embodiments, such as shown in FIGS. 16 and 19A-19D, each of the at least two bone anchors 732 is shaped so as to define anchor head 749 and at least one protrusion 750 that protrudes proximally from anchor head 749 (e.g., by at least 0.5 mm, no more than 5 mm, or between 0.5 and 5 mm, e.g., 1 mm). In some embodiments, distal glenoid-facing surface 838 of elongate labrum receptacle 836 is shaped so as to define a slot 853 configured to receive the at least one protrusion 750 of each of the at least two bone anchors 732, so as to prevent rotation of elongate labrum receptacle 836 with respect to bone anchors 732 when elongate labrum receptacle 836 is coupled to bone anchors 732.

In some embodiments, (configurations not shown), elongate labrum receptacle 836 further comprises a plurality of rigid base frames, which at least partially define distal glenoid-facing surface 838. In some embodiments, the rigid base frames are not shown in FIGS. 16-19D, but may be similar to rigid base frame 746, described hereinabove with reference to FIGS. 12A-12B and 14. In some embodiments, distal surfaces of the rigid base frames define at least a portion of distal glenoid-facing surface 838 of elongate labrum receptacle 836, i.e., the distal surfaces of the rigid base frames are exposed distally. In some embodiments, alternatively or additionally, elongate labrum receptacle 836 comprises a material more flexible than the material of the rigid base frames. In some embodiments, this material defines distal glenoid-facing surface 838. In some embodiments, the rigid base frames at least partially define distal glenoid-facing surface 838 by providing structure to the more flexible material. In some embodiments, proximal trough 840 is more flexible than the rigid base frames. In some embodiments, bone anchors 732 and the rigid base frames are shaped so as to define respective protrusions and protrusion receptacles, such as described for rigid base frame 746, described hereinabove with reference to FIGS. 12A-12B and 14.

In some embodiments, elongate labrum receptacle 836 does not comprise any rigid base frames, such as shown in FIGS. 16-19D.

In some embodiments, (configuration not shown), the at least two bone anchors 732 are shaped so as to define respective anchor heads 749 that are shaped so as to define respective slots. In some embodiments, distal glenoid-facing surface 838 of elongate labrum receptacle 836 is shaped so as to define respective protrusions, which are configured to be inserted into the respective slots of anchor heads 749, so as to prevent rotation of elongate labrum receptacle 836 with respect to bone anchors 732 when elongate labrum receptacle 836 is coupled to bone anchors 732.

In some embodiments, such as shown in FIGS. 16-19D, proximal trough 840 extends along an entire length of elongate labrum receptacle 836 and is open at both ends 856 of elongate labrum receptacle 836. In some embodiments, optionally, proximal trough 840 has a constant depth D2 along the entire length L2 of elongate labrum receptacle 836.

In some embodiments, proximal trough 840 has one or more of the following dimensions:
- a length of between 0.5 and 3 cm, such as between 1 and 2.5 cm, e.g., 2 cm,
- a greatest width W of between 1 and 10 mm, such as between 2 and 8 mm (labeled in FIG. 18), and/or
- a depth D of between 1 and 10 mm, such as between 1.5 and 5 mm, e.g., 2.5 mm (labeled in FIG. 18).

In some embodiments, distal glenoid-facing surface 838 of elongate labrum receptacle 836 has a greatest width $W_G$ of between 1 and 12 mm, such as between 3 and 8 mm.

In some embodiments, proximal trough 840 comprises a textile. In some embodiments, the textile is porous.

In some embodiments, proximal trough 840 is flexible.

Reference is now made to FIGS. 19A-19D, which are schematic illustrations of a method for treating Bankart lesion 702, in accordance with some embodiments of the present invention.

In some embodiments, as shown in FIG. 19A, distal portions 733 of bone anchors 732 are implanted in glenoid rim 706. In some embodiments, optionally, as shown in FIG. 19A, sutures 734 of bone-implant assembly 720 are fixed to and extend proximally from proximal portions 737 of bone anchors 732, respectively.

In some embodiments, as shown in FIG. 19B, elongate labrum receptacle 836 is coupled to proximal portions 737 of bone anchors 732, respectively, such that distal glenoid-facing surface 838 of elongate labrum receptacle 836 rests against glenoid rim 706 and proximal trough 840 of elongate labrum receptacle 836 faces proximally away from distal glenoid-facing surface 838 and glenoid rim 706, toward detached anteroinferior labrum 704 (not visible in FIG. 19B, but shown in FIG. 19D, described hereinbelow).

In some embodiments, such as shown in FIG. 19C, two or more longitudinal suture portions 735 of each of sutures 734 are knotted together when passing through distal glenoid-facing surface 838 of elongate labrum receptacle 836, so as to couple elongate labrum receptacle 836 to proximal portions 837 of bone anchors 732, respectively.

In some embodiments, as shown in FIG. 19D, detached anteroinferior labrum 704 is inserted into proximal trough 840.

In some embodiments, optionally, anteroinferior labrum 704 is sutured to proximal trough 840, typically using sutures 734. In some embodiments, alternatively, anteroinferior labrum 704 is sutured to proximal trough 840 using additional sutures, or is not sutured to proximal trough 840.

Exemplary Void Bone-Filler Implant

In some embodiments, the void bone-filler implant comprises an implant body or implant container (referred hereinafter as container) and a bone anchor (referred hereinafter as anchor). In some embodiments, the anchor is a bone screw anchor. In some embodiments, the anchor is any known anchor in the art adapted to be used in a bone. In some embodiments, the anchor is an all-suture anchor or soft tissue anchor or soft material \ textile based anchor. The terms "all-suture anchor" and "soft material\textile based bone anchor" are interchangeable in the meaning that both comprise an all-suture or soft material \ textile based anchor as means to be anchored in and to the bone. In some embodiments, the container fulfills both the role of containing the bone-void filler in the implant and the role of the bone anchor. Like reference numerals refer to like parts.

Figure 20:
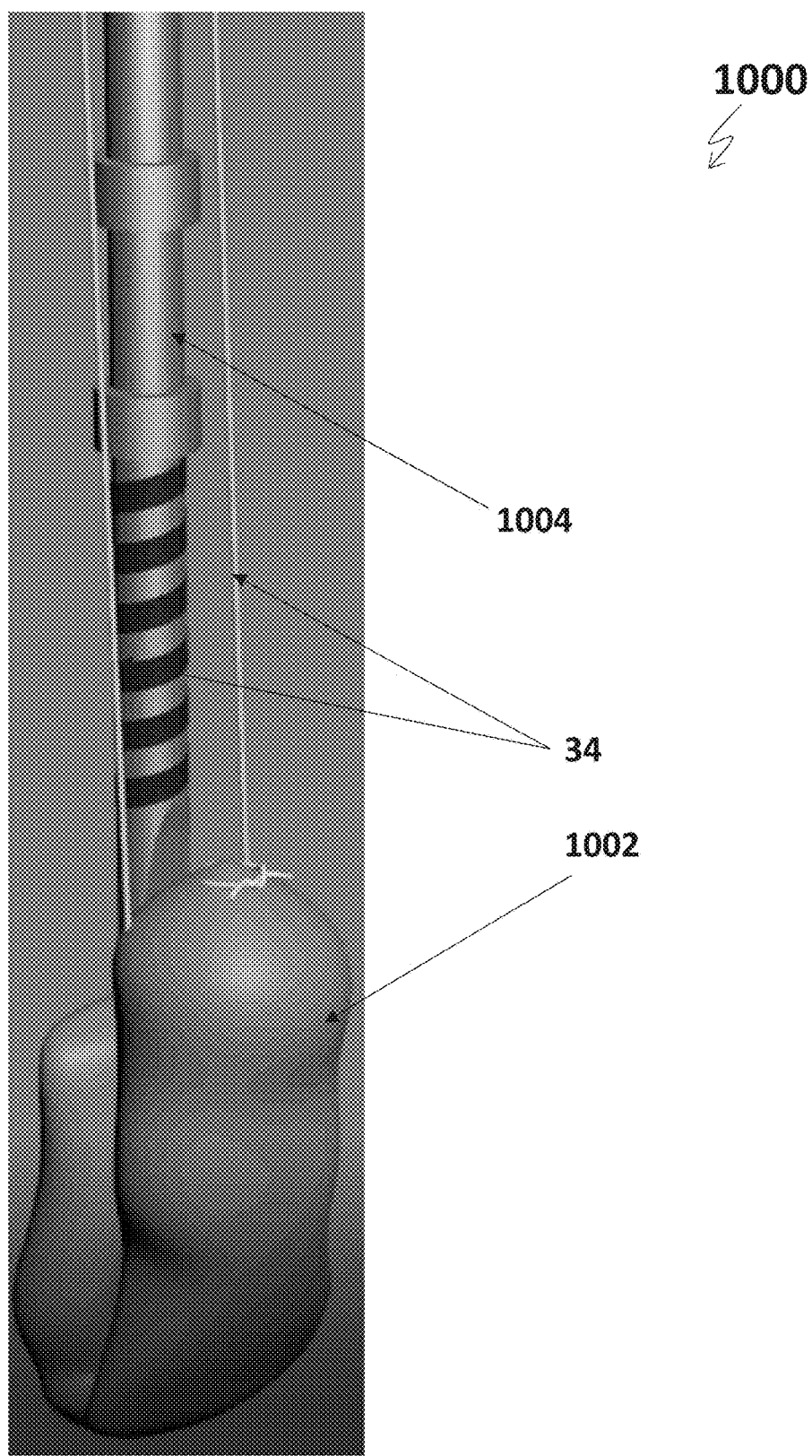
FIG. 20 is a schematic representation of an exemplary void bone-filler implant, according to some embodiments of the invention.

Reference is made to FIG. 20 showing a schematic representation of an exemplary a void bone-filler implant 1000, according to some embodiments of the invention. In some embodiments, the void bone-filler implant 1000 comprises an implant body/container 1002, which comprises an osteoconductive bone-filler material 42. In some embodiments, the container 1002 comprises one or more sutures 34 or threads (previously referred sutures will also be called threads from here on—the meaning of both is intended to be the same). In some embodiments, the one or more threads 34 fulfill two roles: compressing the container 1002 in its role as the anchor and/or the vessel for the osteoconductive bone-filler material, and optionally tying adjacent tissue to the implant, thereby attaching together the adjacent tissue and the bone where the implant is positioned. In some embodiments, the bone void-filler implant 1000 is attached and/or mounted to an anchor inserter 1004, as is usually done in the art with regular all-suture/soft tissue bone anchors.

Exemplary Osteoconductive Bone-Filler Material 42

In some embodiments, one or more osteoconductive bone-filler materials are used for the repair of the relevant bones. In some embodiments, osteoconductive bone-filler material of the bone void-filler implant causes the bone void-filler implant to osseointegrate with the bone. In some embodiments, as mentioned above, the osteoconductive bone-filler material includes a biodegradable or non-biodegradable matrix. For example, osteoconductive bone-filler material 42 may comprise a polyester braid tube, distributed by Secant group (Telford, Pa., USA), calcium phosphate spheres distributed by Himed (Old Bethpage, N.Y., USA).

In some embodiments, osteoconductive bone-filler material 42 comprises one or more organic materials, for example, bone marrow, bone marrow stem cells, osteogenic cells, preosteoblasts, osteoblasts, mesenchymal stem cells, bone marrow mesenchymal stem cells and pluripotent stem cells. In some embodiments, organic material is extracted from the patient prior to the implantation of the bone implant assembly, in general, and prior to the implantation of the void bone-filler implant 1000, in particular. In some embodiments, the material inserted is an autologous bone, harvested during procedure. In some embodiments, the diameter of the harvested bone material, optionally in the form of a roll, depends on the size of the bone marrow needle that is used, for example a 11G needle that harvests a roll having a diameter of from about 2.3 mm to about 2.4 mm. In some embodiments, the length of the bone roll depends on drilling depth, for example, the length of the roll can be from about 10 mm to about 40 mm. In some embodiments, the harvested material is optionally crushed before being inserted into the container 1002.

Exemplary Container 1002

In some embodiments, the container 1002 comprises a tubular sleeve. In some embodiments, the tubular sleeve is made of one or more of braided Polyester, Braided UHMWPE (Ultra high molecular weight polyethylene), braided Polyethylene, biodegradable materials such as PLA, PLLA, PGA, PLGA and PHB, and any combination thereof. In some embodiments, the tubular sleeve comprises a woven or braided mesh. In some embodiments, the tubular sleeve comprises a porous material, for example, the tubular sleeve comprises pores having sizes of from about 0.5 mm (height)×0.5 mm (width) to about 3 mm (height)×3 mm (width). Optionally from about 0.3 mm (height)×0.3 mm (width) to about 5 mm (height)×5 mm (width). Optionally from about 0.1 mm (height)×0.1 mm (width) to about 10 mm (height)×10 mm (width). In some embodiments, the size of the height and the size of the width are the same, for example 1 mm×1 mm, 1.5 mm×1.5 mm, 2 mm×2 mm. In some embodiments, the size of the height and the size of the width are not the same, for example 1 mm×1.5 mm, 0.5 mm×2 mm, 1.5 mm×2 mm. In some embodiments, the tubular sleeve is made of filaments having a diameter of from about 0.3 mm to about 0.6 mm. Optionally from about 0.1 mm to about 0.8 mm. Optionally from about 0.05 mm to about 1 mm.

In some embodiments, when defining the structure of the tubular sleeve, which comprises a woven or braided mesh, the horizontal row of loops or stitches running across the width of the knitted fabric corresponds to course of the knitted fabric. In the art, the numbers of course in an inch in a knitted fabric is called course per inch (CPI). On the other hand, the column of loops running lengthwise the fabric is known as wales. In the art, numbers of wales in an inch in knitted fabric is called wales per inch (WPI). In some embodiments, the tubular sleeve comprises an average of from about 20 CPI to about 30 CPI; optionally from about 15 CPI to about 40 CPI; optionally from about 10 CPI to about 50 CPI, for example 24 CPI, 27 CPI, 34 CPI. In some embodiments, the tubular sleeve comprises an average of from about 10 WPI to about 20 WPI; optionally from about 8 WPI to about 30 WPI; optionally from about 5 WPI to about 50 WPI, for example 16 WPI, 18 WPI, 23 WPI.

Figure 21:
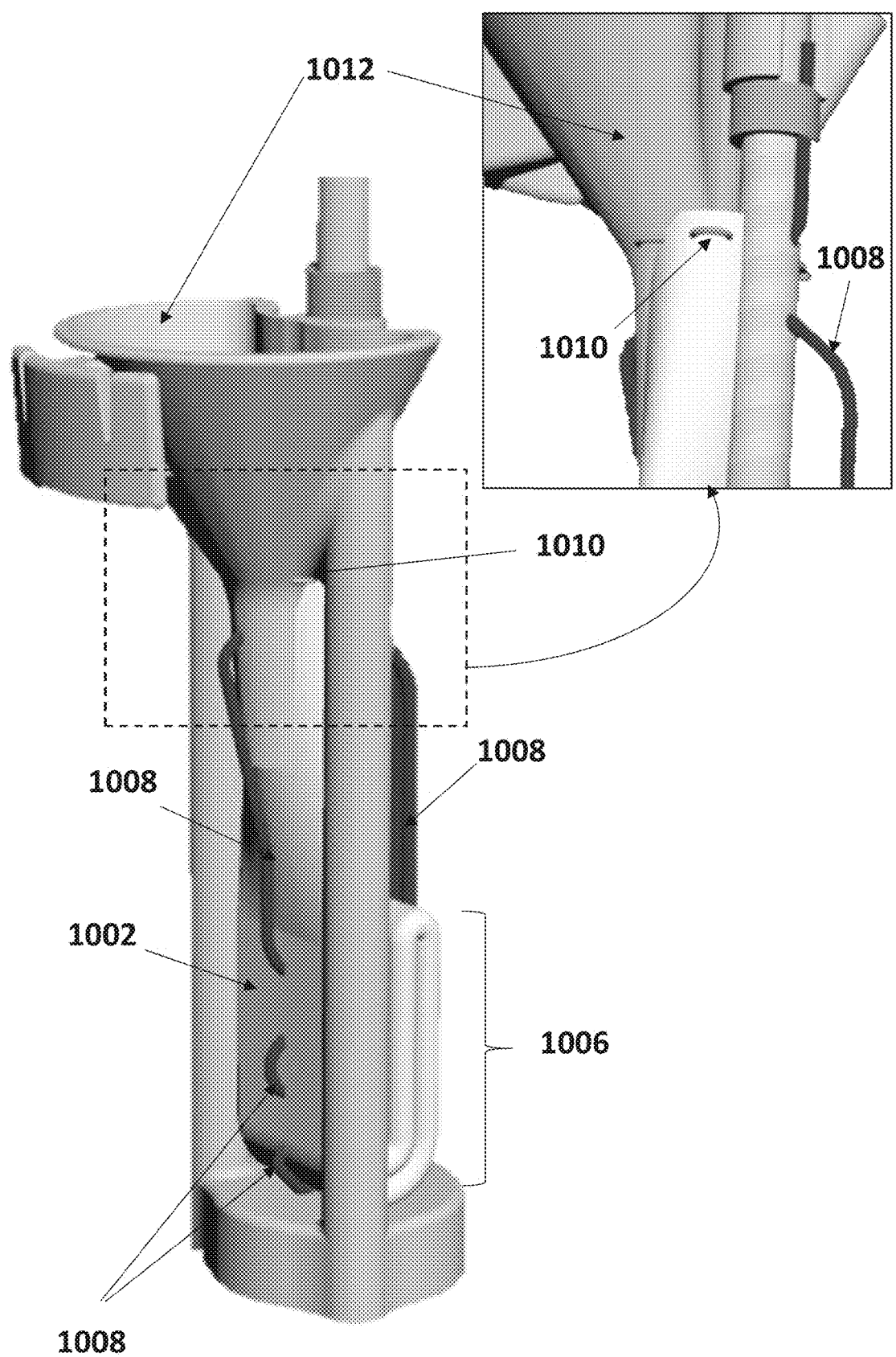
FIG. 21 is a schematic representation of an exemplary void bone-filler implant with an exemplary funnel, according to some embodiments of the invention.

In some embodiments, at least part of the tubular sleeve is used as an anchoring part of the void bone-filler implant. In some embodiments, the tubular sleeve comprises a distal end and a proximal end. In some embodiments, the distal end is folded so the tubular body is folded on itself (see 1006), as shown for example in FIG. 21. In some embodiments, one or more longitudinal threads 1008 pass through from one side of the proximal end of the tubular sleeve, along the body of the tubular sleeve, closing the distal end (which is folded) of the tubular sleeve and again along the body of the tubular sleeve until it reaches the other side of the proximal end of the tubular sleeve, as shown for example in FIG. 21, which thereby form at least two longitudinal thread portions. In some embodiments, the proximal end comprises one or more horizontal threads 1010 configured to close the proximal end of the tubular sleeve after the one or more osteoconductive bone-filler material is inserted therein.

Figure 22:
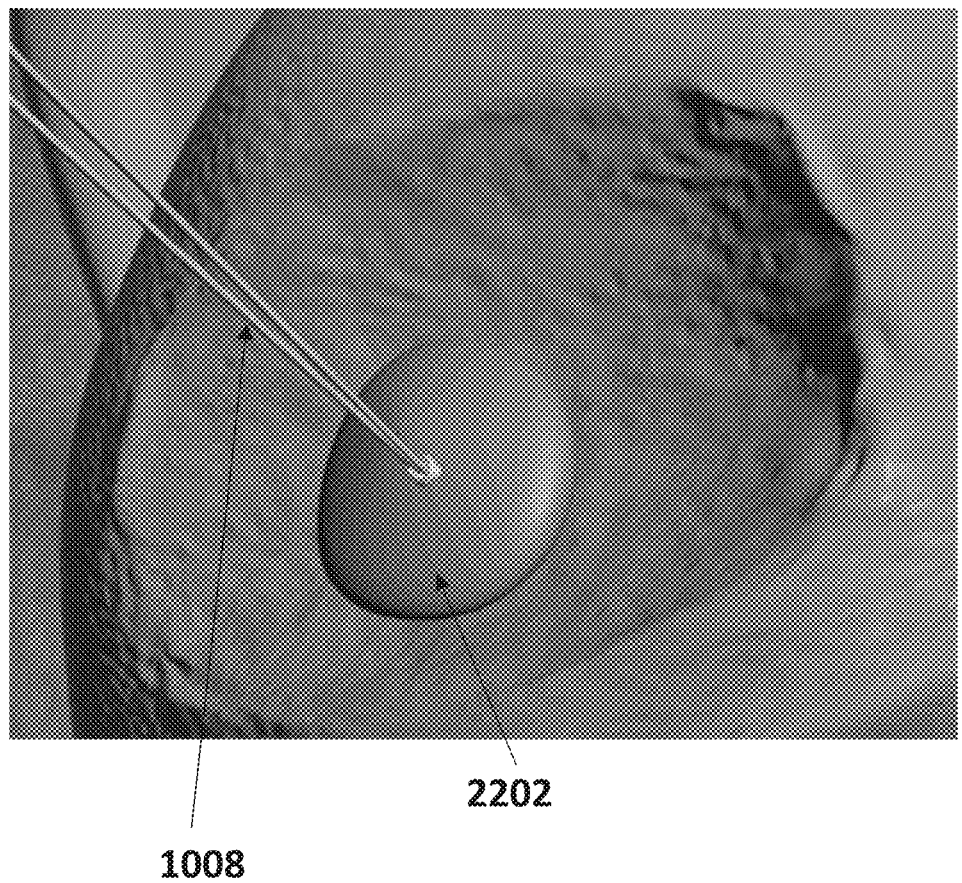
FIG. 22 is a schematic representation of an exemplary void bone-filler implant once implanted in a bone, according to some embodiments of the invention.

In some embodiments, container 1002 is configured to transition from an elongate, low-profile delivery configuration (as shown for example in FIGS. 20 and 21) to a shortened radially-expanded deployment configuration 2202 (as shown for example in FIG. 22). In some embodiments, the shortened radially-expanded deployment configuration causes the container to be pressed against the bone and/or the anchor in the bone. In some embodiments, the shortened radially-expanded deployment configuration is caused, for example, upon distal performing one more knots using the at least two longitudinal thread portions, as will be further explained below.

In some embodiments, the shortened radially-expanded deployment configuration is maintained by means of an attachment mechanism located between the anchor and the container. For example, a male-female attachment mechanism, a screw connection mechanism, organic glues, sutures, and/or any other known attaching mechanism known in the art.

In some embodiments, in order to facilitate the explanations, the implant comprises two sections: a distal folded side, which acts as the anchor for the implant in the bone (referred also as "the anchor") and a proximal side, which comprises the container with the material that will fill the lesion in the bone (referred also as "bone filler" that fills the lesion). In some embodiments, the abovementioned description is valid for both the anchoring section inside the bone and the container section above the bone.

In some embodiments, the threads 1008 are arranged such that when one or more knots are formed upon knotting together the at least two longitudinal thread portions of the one or more longitudinal threads are within a proximal portion of the tubular sleeve, such that the one or more knots attach the container 1002 top the surface of the bone.

Exemplary Filling and Preparing the Container 1002 with Osteoconductive Bone-Filler Material 42

In some embodiments, as explained above, one or more organic materials are used as the osteoconductive bone-filler material 42. In some embodiments, when autologous organic material is used, organic material is harvested from the same subject that the implant will be used on. In some embodiments, once the organic material is harvested, it is then inserted into the container 1002, optionally using a dedicated funnel 1012, as shown for example in FIG. 21. In some embodiments, once the organic material is inserted, the container 1002 is closed/sealed using for example the one or more horizontal threads 1010.

Exemplary Procedure

Figure 23:
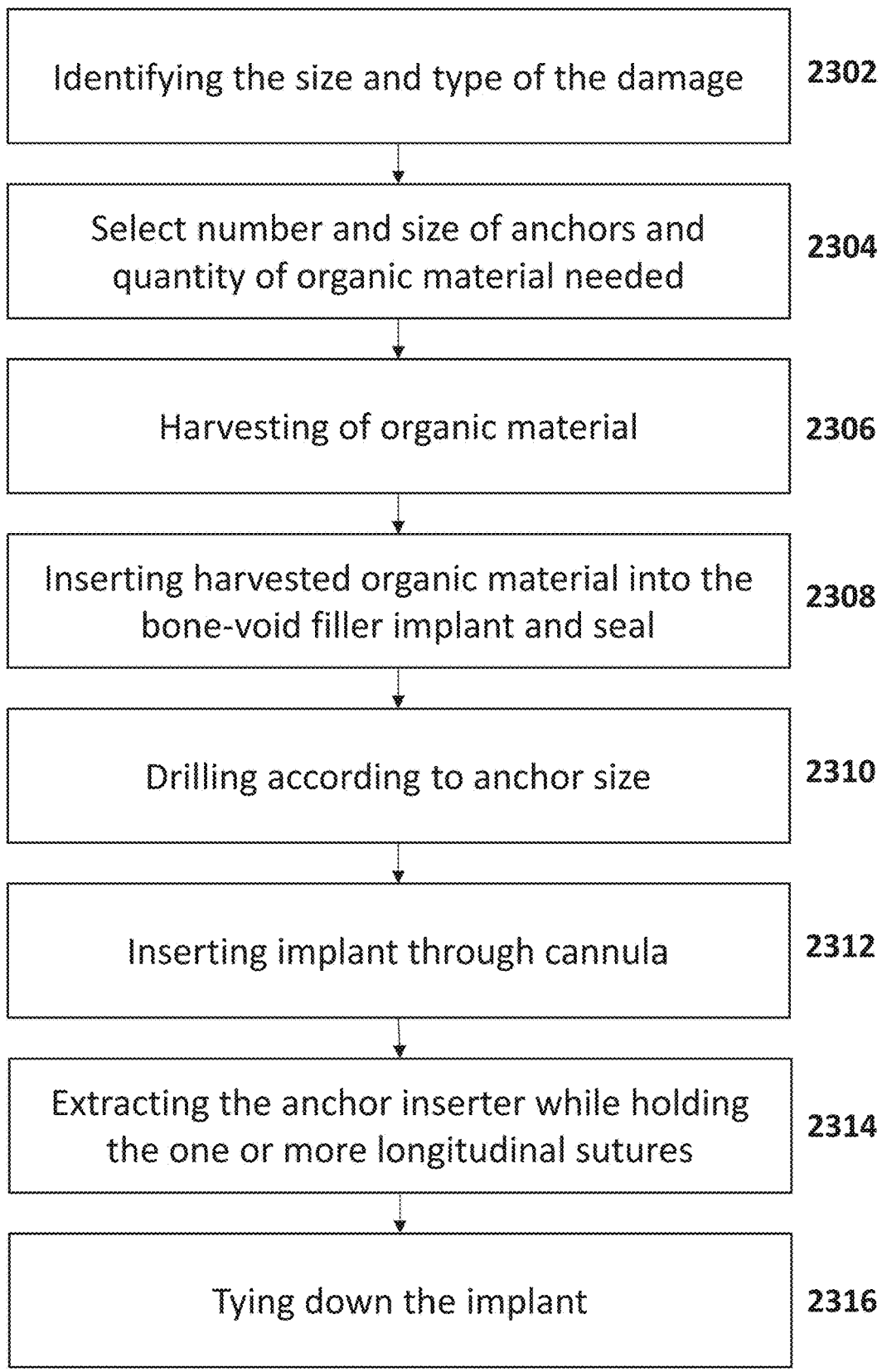
FIG. 23 is a flowchart of an exemplary procedure, according to some embodiments of the invention.
Figure 24A:
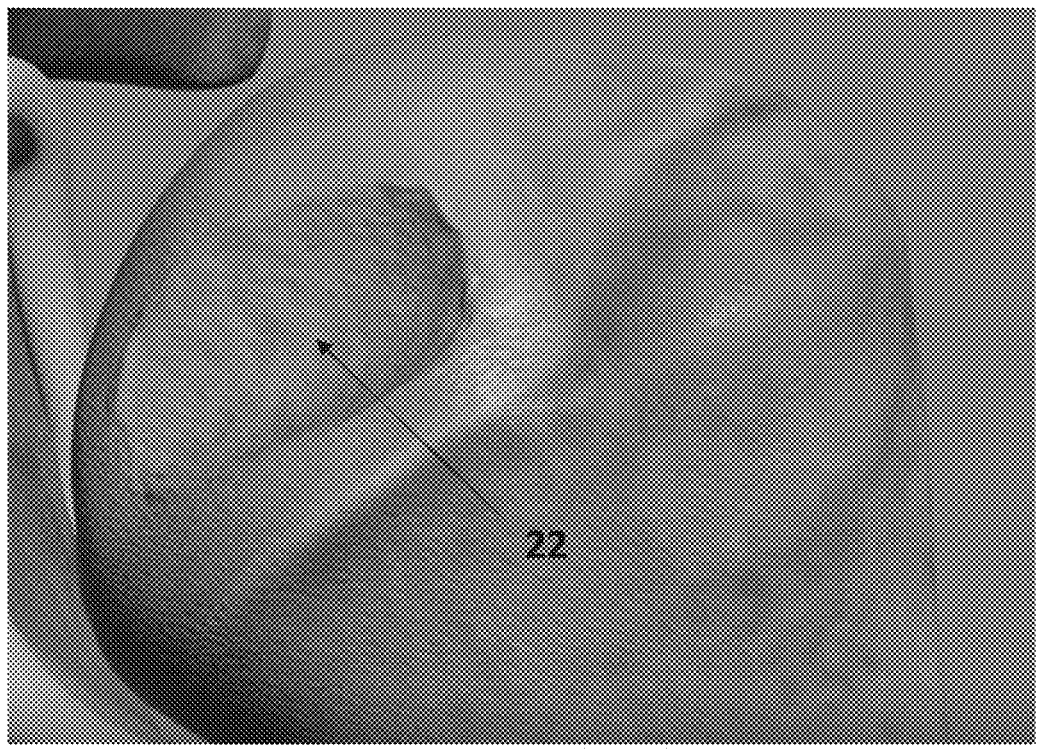
Figure 24B:
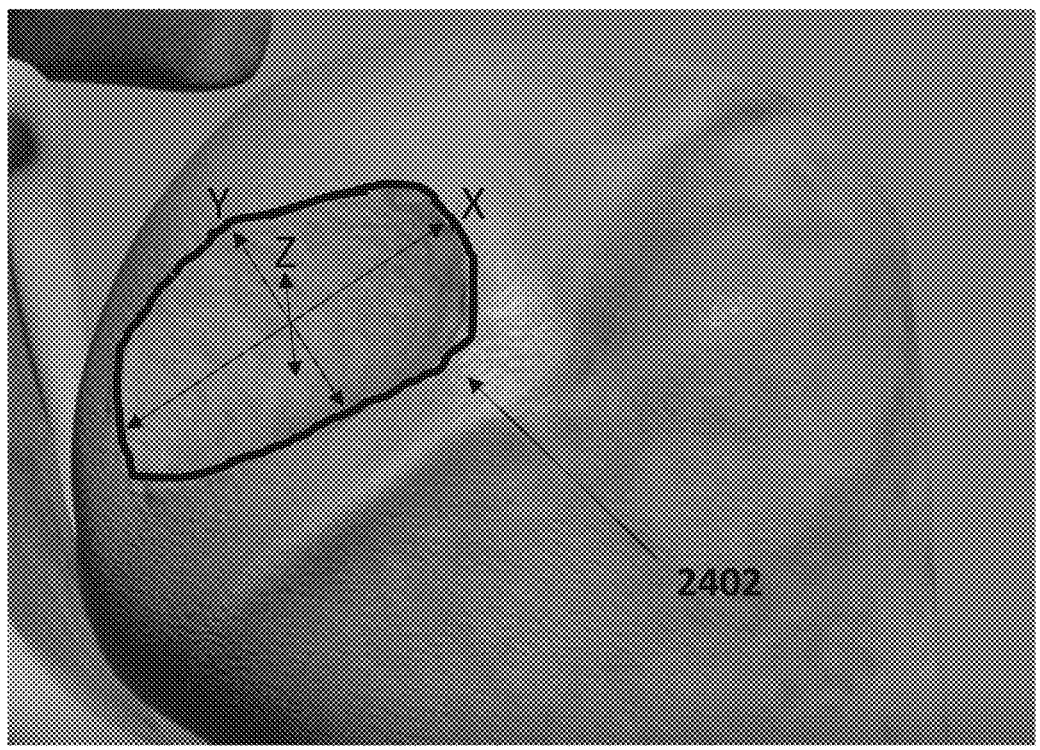

In the following paragraphs an exemplary procedure will be described. For the explanations an exemplary procedure to treat a Hill-Sachs lesion 22 will be used. It should be understood that the same or similar procedures can be used to treat other types of lesions. Referring now to FIG. 23 showing a flowchart of an exemplary procedure, according to some embodiments of the invention. Additionally, referring to FIGS. 24a-24x, showing schematic illustrations of exemplary different steps performed during the exemplary procedure. In some embodiments, an exemplary procedure of treating a bone lesion comprises:

1. Identifying the size and type of the damage 2302, for example a Hill-Sachs lesion 22 and/or a labral tear, by using for example CT and/or MRI, as schematically shown in FIG. 24a and FIG. 24b. In some embodiments, during the identification the bone defect size (see 2402 in FIG. 24b) and/or percentage is calculated.

2. Selection of implants/anchors and quantity of organic material 2304. In some embodiments, a selection of type and number of anchors is chosen, based on the identified bone defect size and/or percentage is calculated. In some embodiments, a calculation of the quantity of how much organic material is needed according to the size of defects and number of planned anchors to be deployed is performed. For example: approximately one harvesting for one container. Optionally two harvesting per container. Optionally between one and three harvestings per container. Optionally more.

Figure 24C:
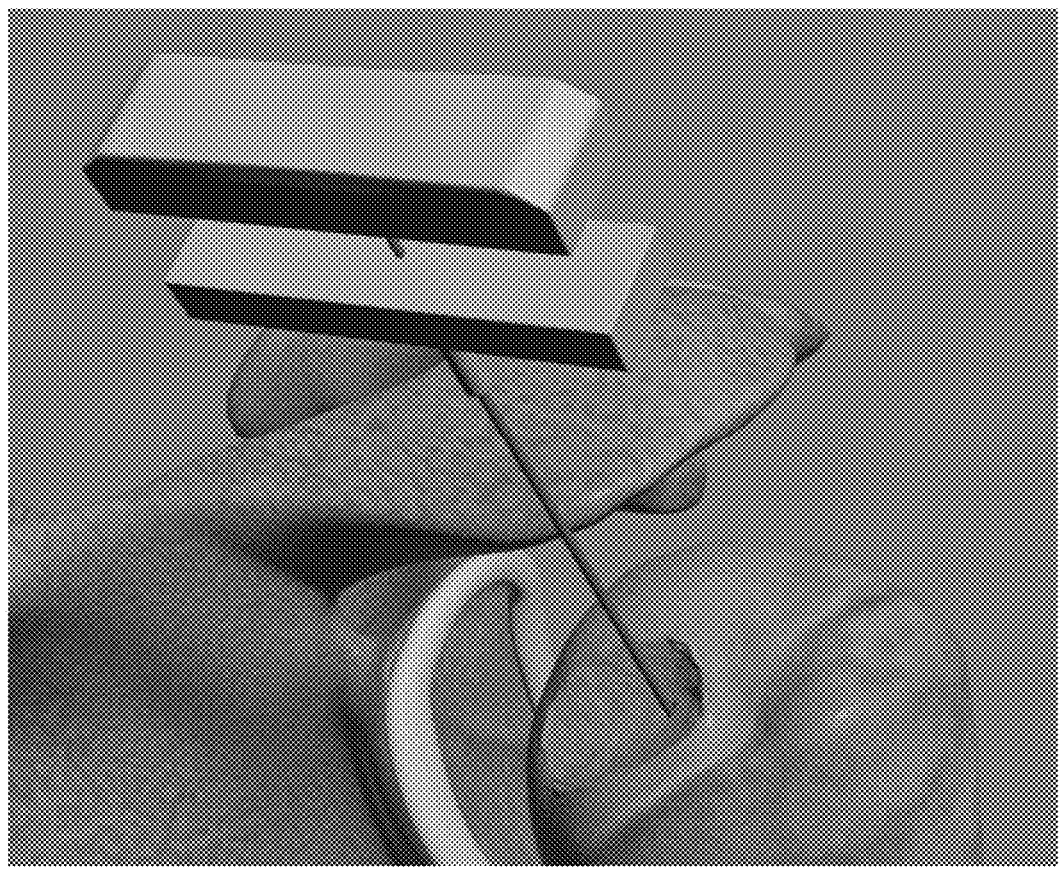
Figure 24D:
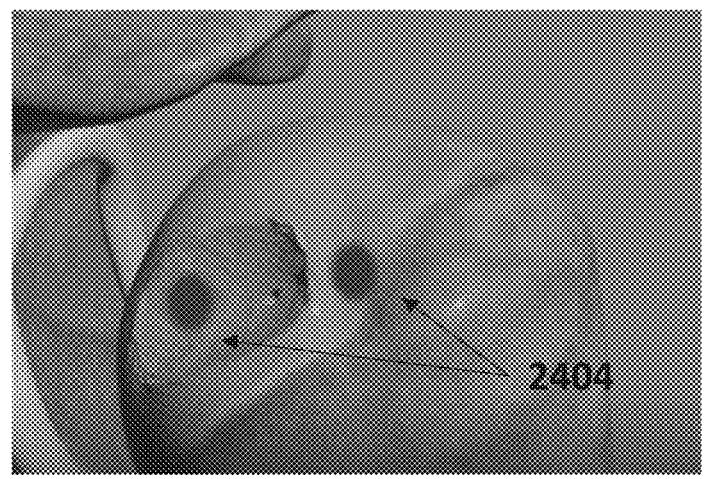

3. Harvesting of organic material. In some embodiments, for example, when bone marrow is used as organic material, harvesting is performed according to the quantity of organic material calculated before, as schematically shown in FIG. 24c. In some embodiments, a cannula 2412 with see through capability (window—Stainless steel/Clear plastic—see through) is introduced to the area of the harvesting (as shown for example in FIG. 24k). In some embodiments, when the area of harvesting and implanting is one and the same, the same cannula 2412 is used for the whole procedure. An example of harvesting areas 2404 on the bone to be repaired are shown in FIG. 24d. In some embodiments, the harvesting is performed from a non-joint area. In some embodiments, the harvesting is performed for example at the HSL (Hill-Sachs lesion) or at the bare area near the footprint.

Figure 24I:
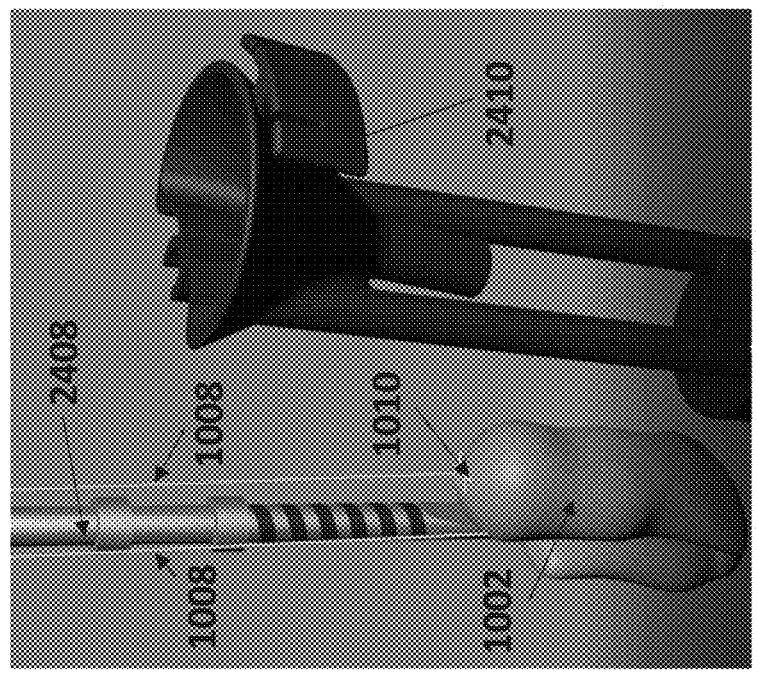
Figure 24H:
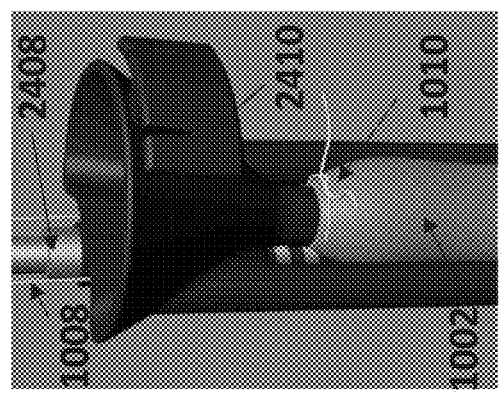
Figure 24G:
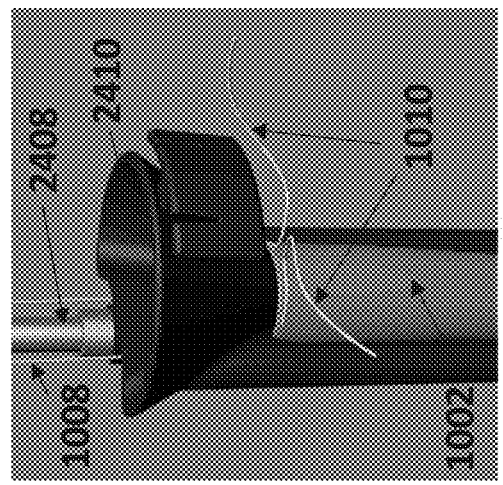
Figure 24J:
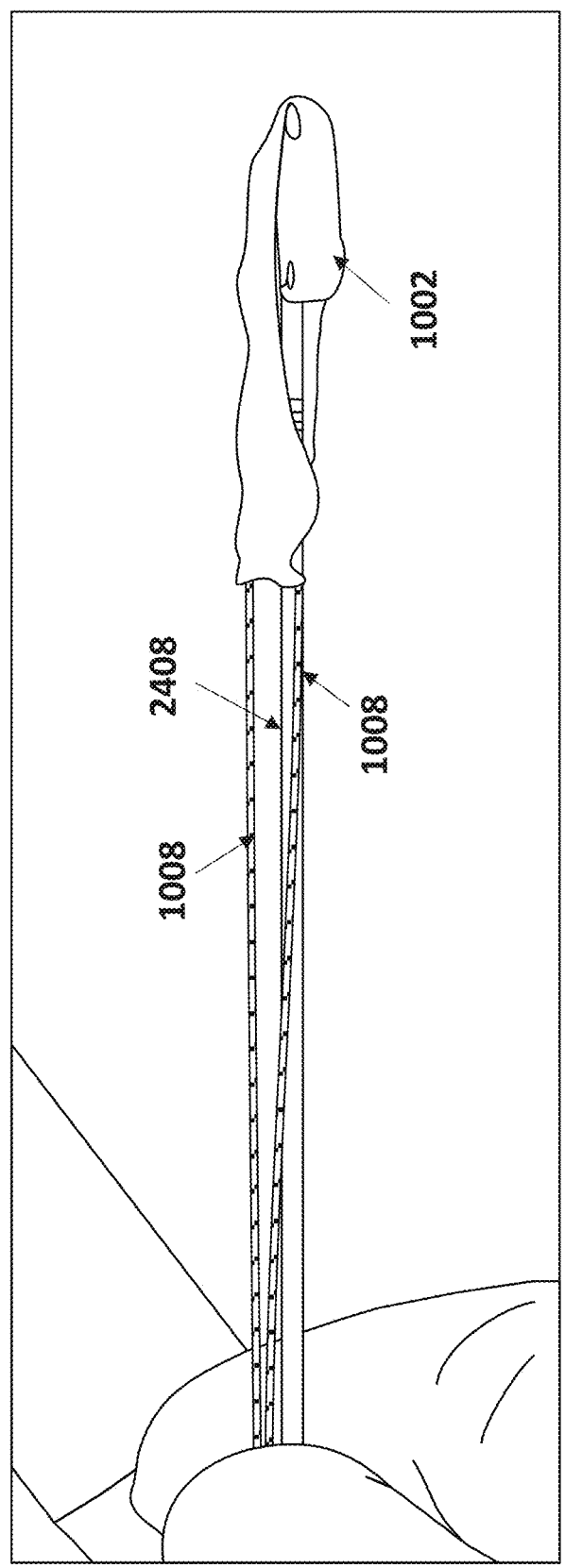

4. Inserting harvested organic material into the bone-void filler implant 2308. In some embodiments, once the organic material 2406 has been harvested, it is inserted into the container 1002 of the bone void-filler implant 1000, through its proximal end. In some embodiments, the container 1002 is already mounted onto an anchor inserter 2408. In some embodiments, the insertion of the organic material 2406 is optionally performed using a dedicated funnel 2410. FIGS. 24e and 24f schematically show the insertion of the organic material 2406 into the container 1002 using the dedicated funnel 2410. In some embodiments, after inserting the organic material into the container 1002, the proximal end is sealed using for example the one or more horizontal threads 1010, as schematically shown in FIGS. 24g and 24h. In some embodiments, the funnel 2410 is then removed, as schematically shown in FIG. 24i, leaving the device ready be used on the subject. FIG. 24j shows a picture of an exemplary device ready to be used on a subject, according to some embodiments of the invention.

5. Drilling according to anchor size 2310. In some embodiments, when the area of harvesting is not the same as the area of implantation, a cannula 2412 with see through capability (window—Stainless steel/Clear plastic—see through) is introduced to the area where the implant is going to be inserted, as shown for example in FIG. 24k. In some embodiments, using a drill 2414, a hole 2416 is drilled to the required depth according to the chosen anchor, as shown for example in FIGS. 24l and 24m. In some embodiments, once the hole is drilled, the drill is extracted from the cannula.

Figure 24O:
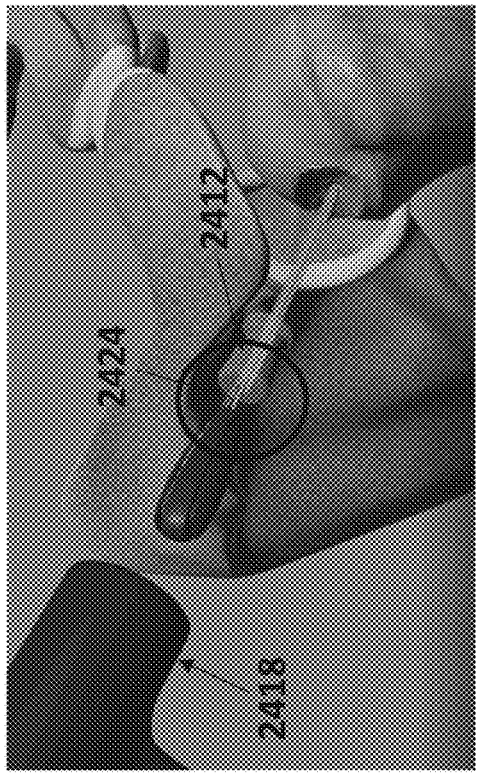
Figure 24Q:
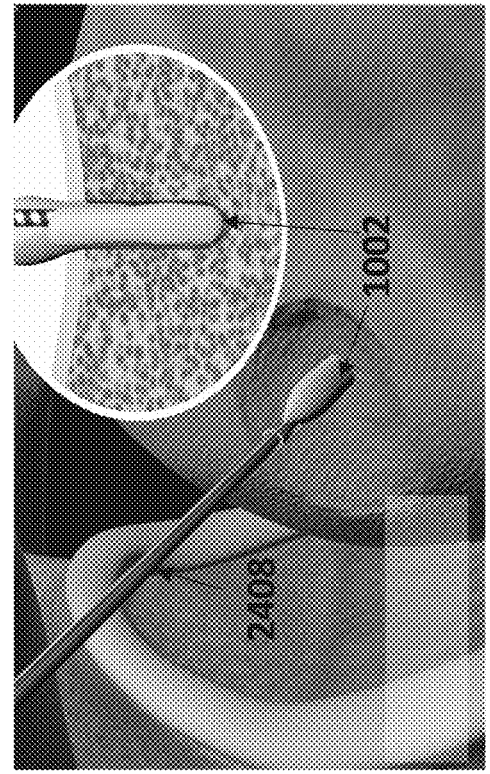
Figure 24N:
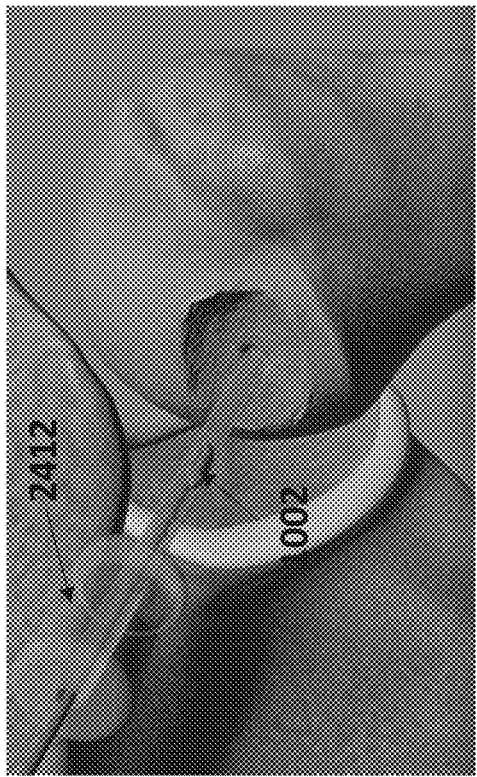
Figure 24P:
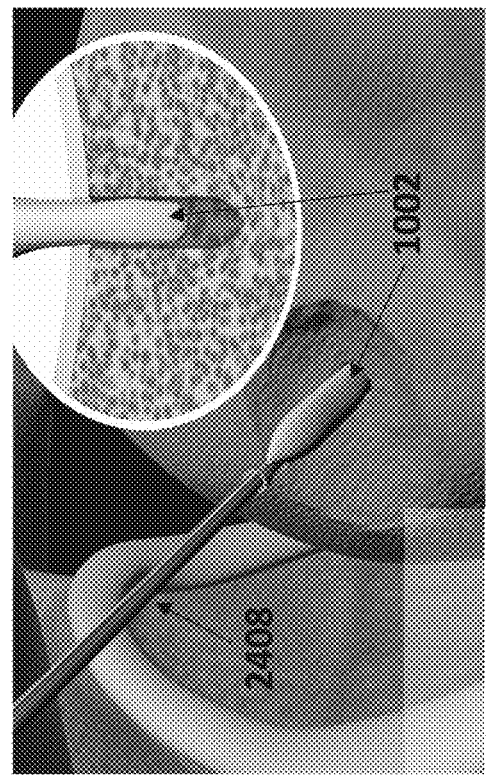

6. Inserting implant through cannula 2312. In some embodiments, the void bone-filler implant mounted on the anchor inserter 2408 is inserted into the cannula 2412, and, optionally using a hammer 2418, the distal end of the implant, which act as the anchor, is inserted according to the depth defined by the user, for example, by setting the depth to which the anchor inserter meets the cannula's back end (see 2424 in FIG. 24o), as schematically shown for example in FIGS. 24n, 24o, 24p and 24q.

Figure 24R:
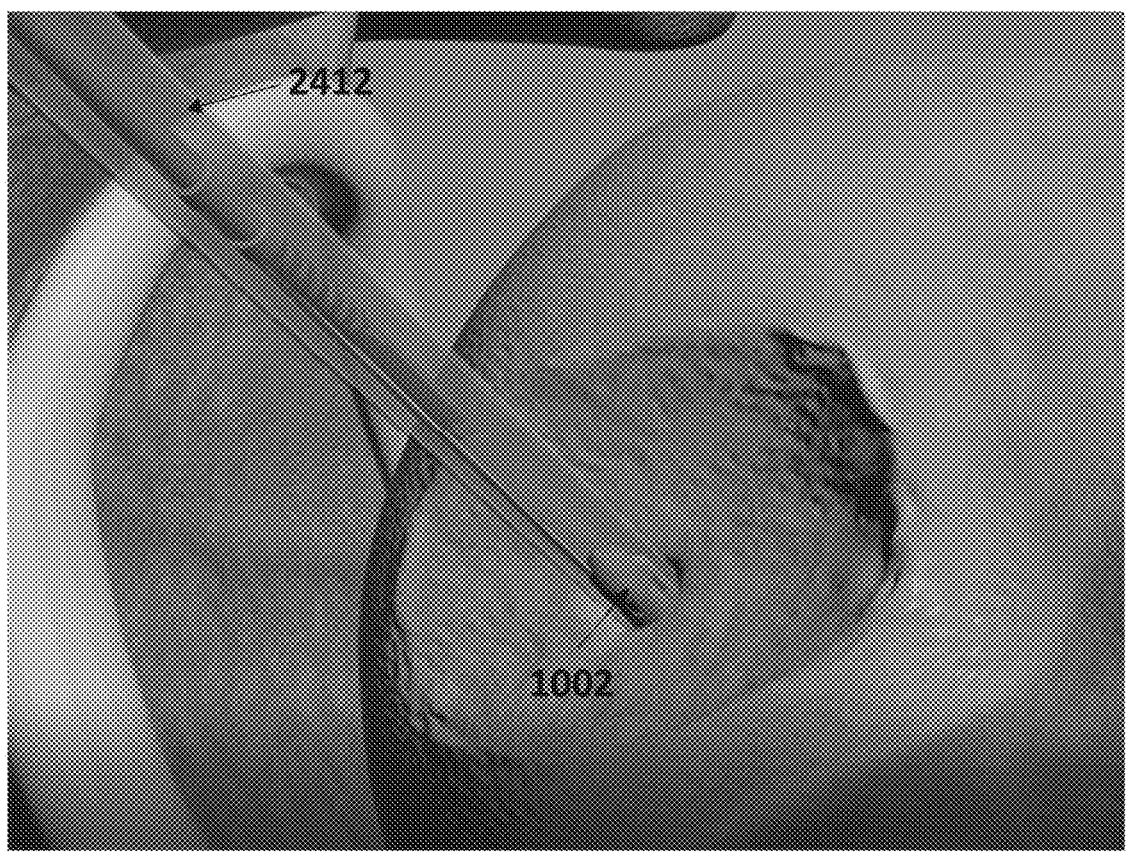
Figure 24S:
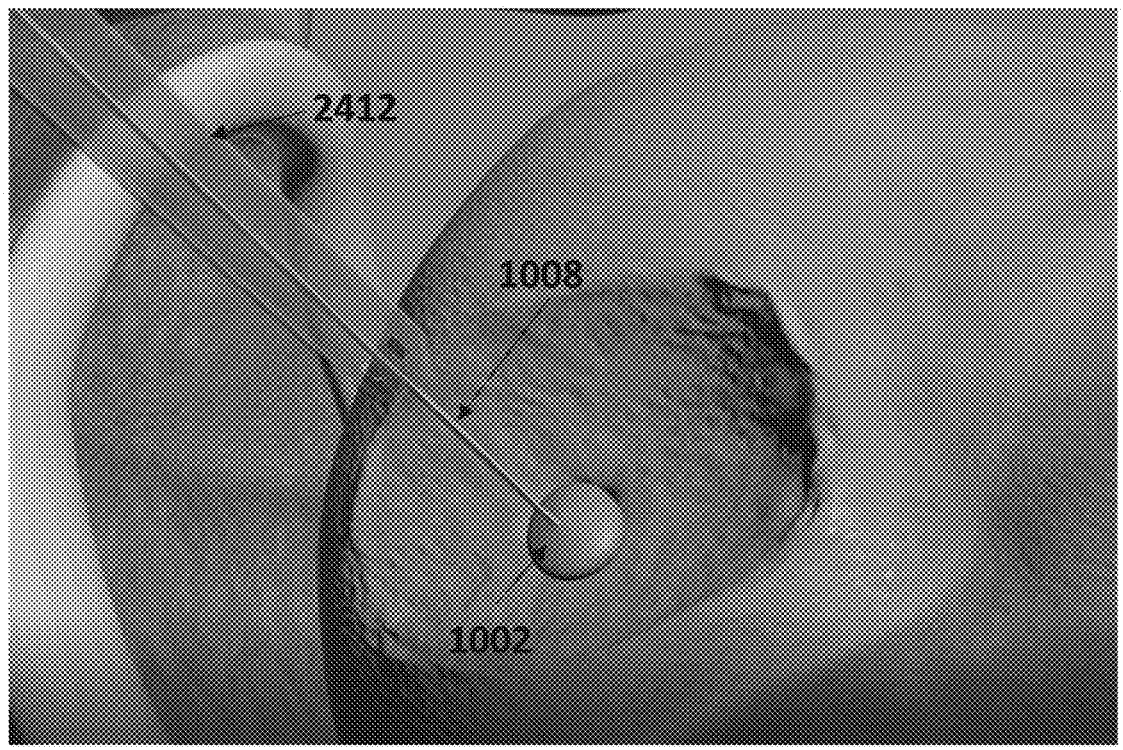

7. Extracting the anchor inserter while holding the one or more longitudinal threads 2314. In some embodiments, the anchor inserter 2408 is then removed while holding the one or more longitudinal threads 1008, as shown for example in FIG. 24r. In some embodiments, optionally, the cannula 2412 is then extracted, as shown for example in FIG. 24s. In some embodiments, the cannula 2412 is only extracted at the end of the procedure.

Figure 24T:
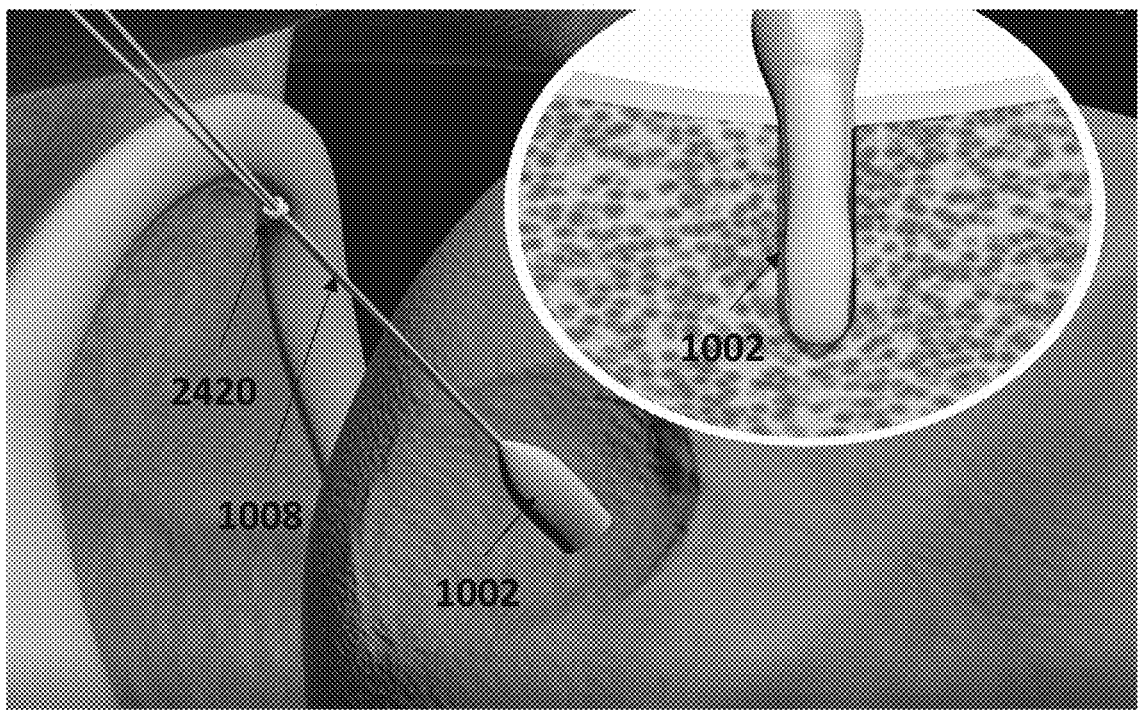
Figure 24U:
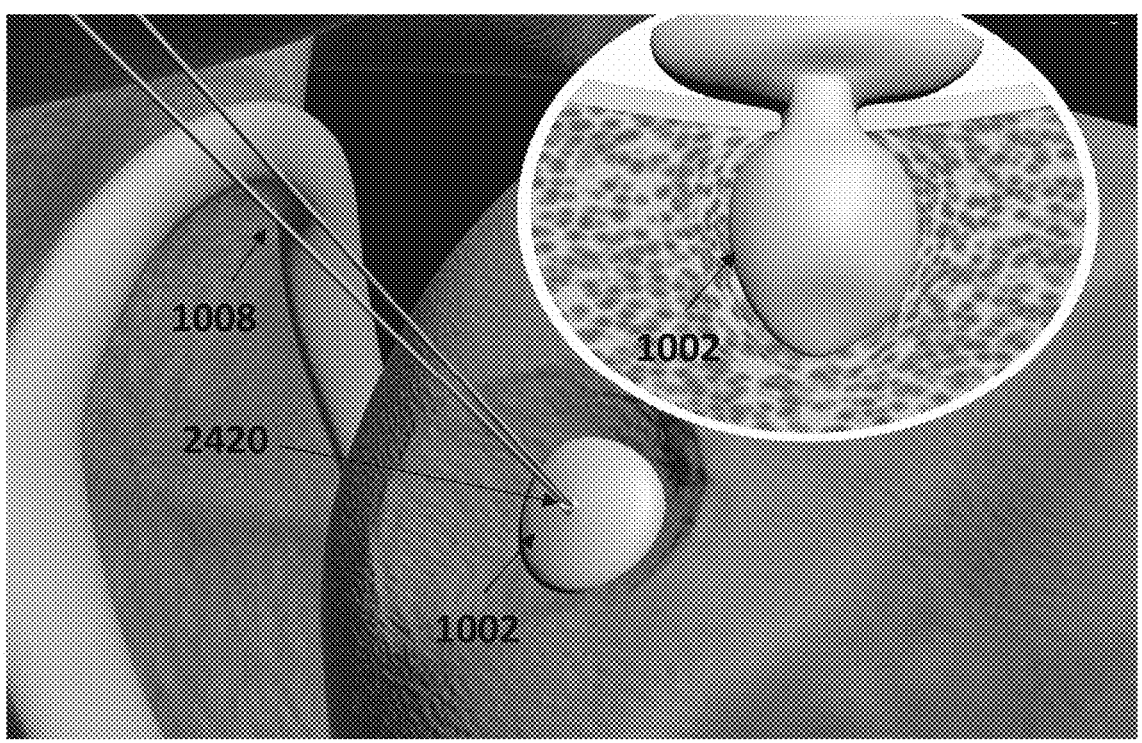

8. Tying down the implant 2316. In some embodiments, using the one or more longitudinal threads 1008, the implant is tied down by performing one or more knots 2420, as shown for example in FIGS. 24t and 24u. In some embodiments, the action of tying down the implant will perform two distinct actions: on one side will activate the anchoring action of the implant, and on the other side, will extend radially the container 1002 so as to cover as much area on the surface of the bone.

In some embodiments, optionally, multiple implants are implanted in the bone, as shown for example in FIG. 24v.

In some embodiments, after a while, the organic material in the container 1002 will induce the filling of the lesion 2422, as schematically shown in FIGS. 24w and 24x.

Exemplary Procedure for Glenoid Rim

Referring now to FIGS. 25a-25l, showing schematic illustrations of an exemplary procedure for the glenoid rim, according to some embodiments of the invention. Numbering of same parts as in FIGS. 24a-24x were kept in FIGS. 25a-25l. In some embodiments, when a repair in the glenoid rim is necessary, similar and/or additional actions are performed when compared to the procedure disclosed above, for example:

1. Preparing glenoid rim at the site of the Bankart defect.

2. Bringing the cannula 2412 to the location and inserting the drill 2414 to drill a hole in the bone, as shown for example in FIGS. 25a and 25b.

3. Inserting the anchor inserter 2408 with the implant 1000 mounted on it in the cannula and, optionally using a hammer 2418, the anchor is inserted, as shown for example in FIGS. 25c and 25d.

4. Releasing the one or more longitudinal threads 1008 from the anchor inserter 2408 and extracting the anchor inserter 2408, as shown for example in FIGS. 25e and 25f.

5. Tying down the implant using the one or more longitudinal threads 1008, by performing one or more knots 2420, as shown for example in FIGS. 25g and 25h.

6. In some embodiments, more than one bone-void filler implant 1002 is used, as shown for example in FIG. 25i, where two bone-void filler implant 1002 are shown.

7. Suturing 2502 labral tear 2504 to glenoid anchors using threads that are attached to glenoid anchors, as shown for example in FIG. 25j.

8. Checking stability and view joint congruity.

Figure 25A:
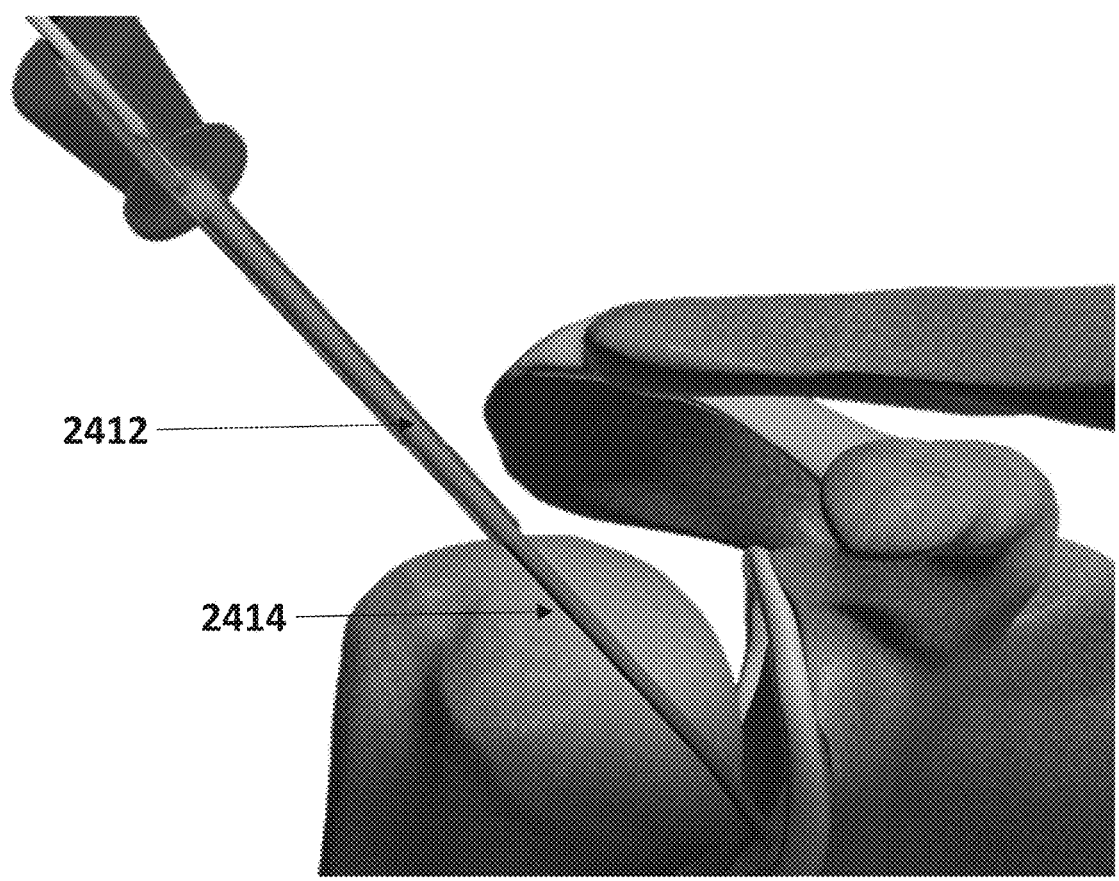
FIGS. 25a, 25b, 25c, 25d, 25e, 25f, 25g, 25h, 25i, 25j, 25k and 25l are schematic illustrations of an exemplary procedure, according to some embodiments of the invention.
Figure 25B:
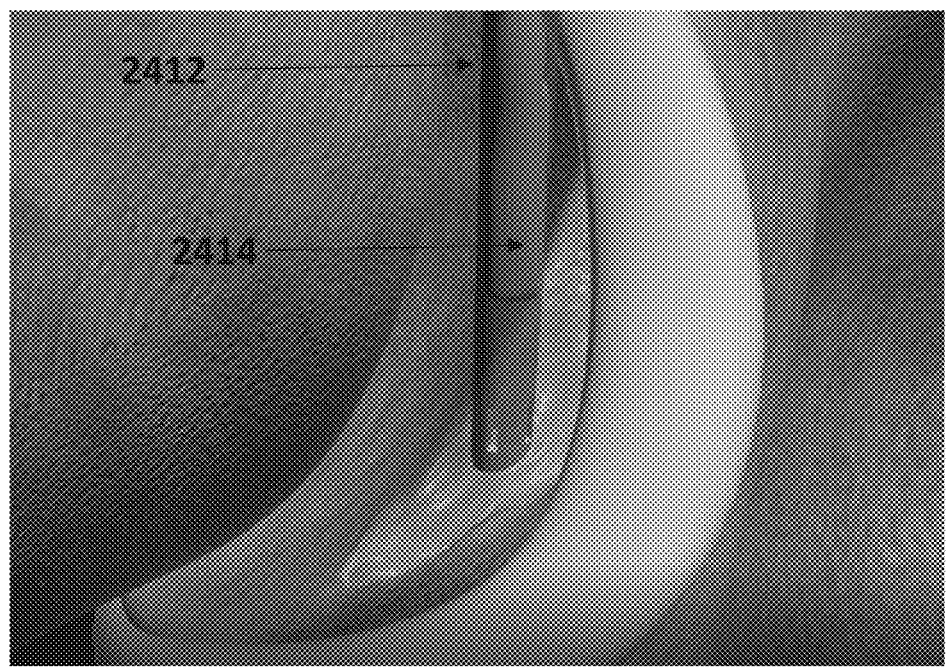
Figure 25C:
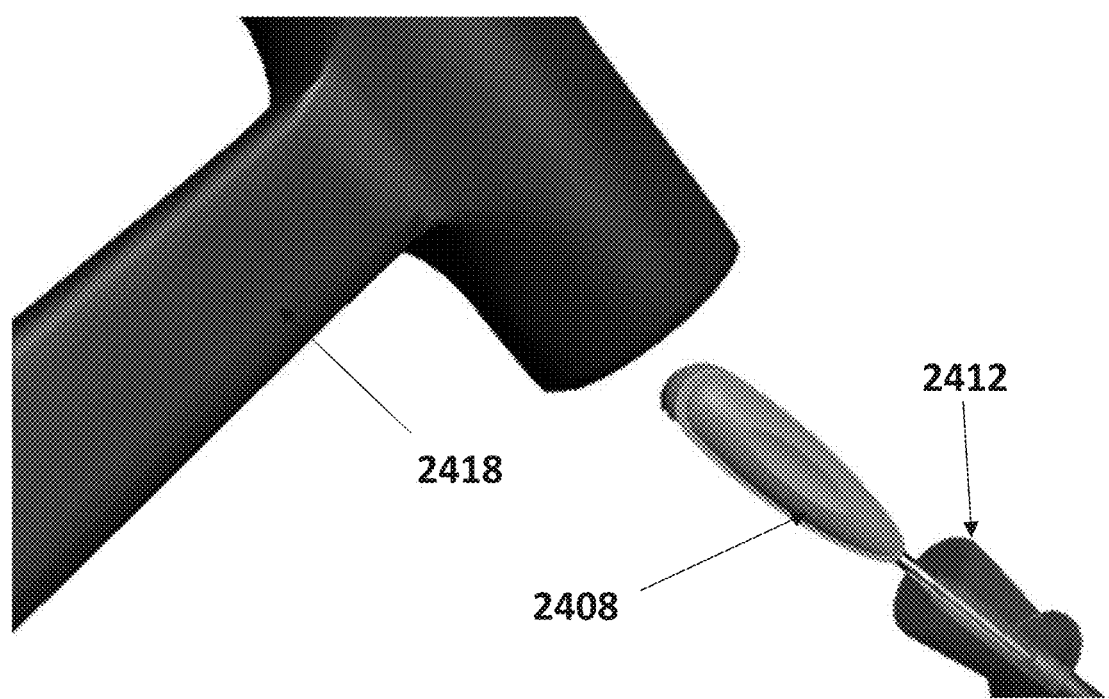
Figure 25D:
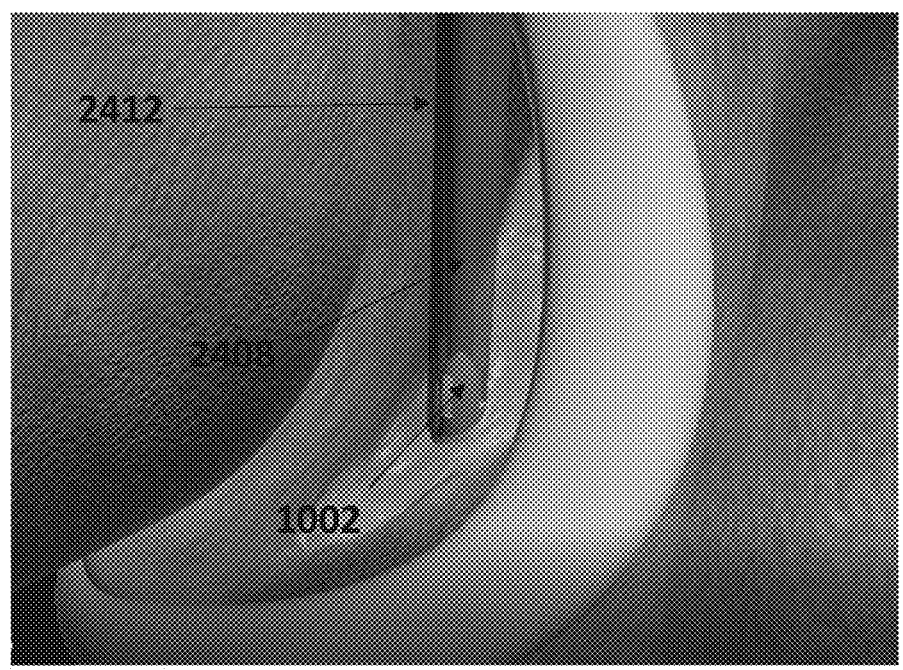
Figure 25E:
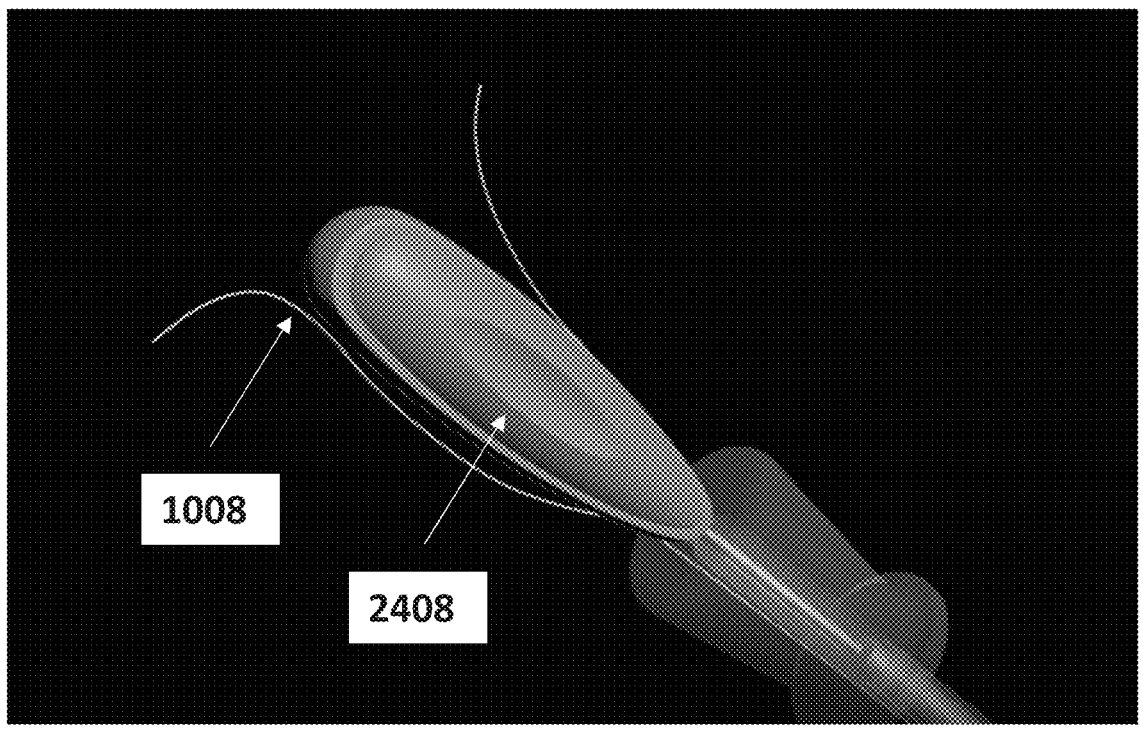
Figure 25F:
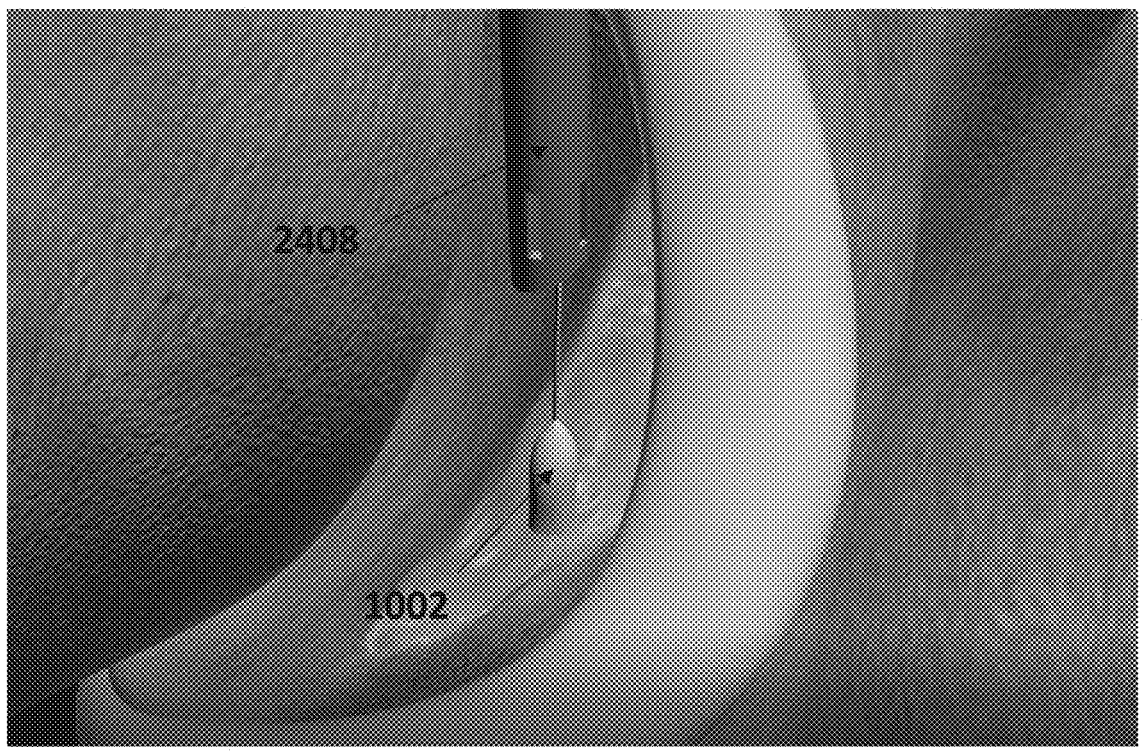
Figure 25G:
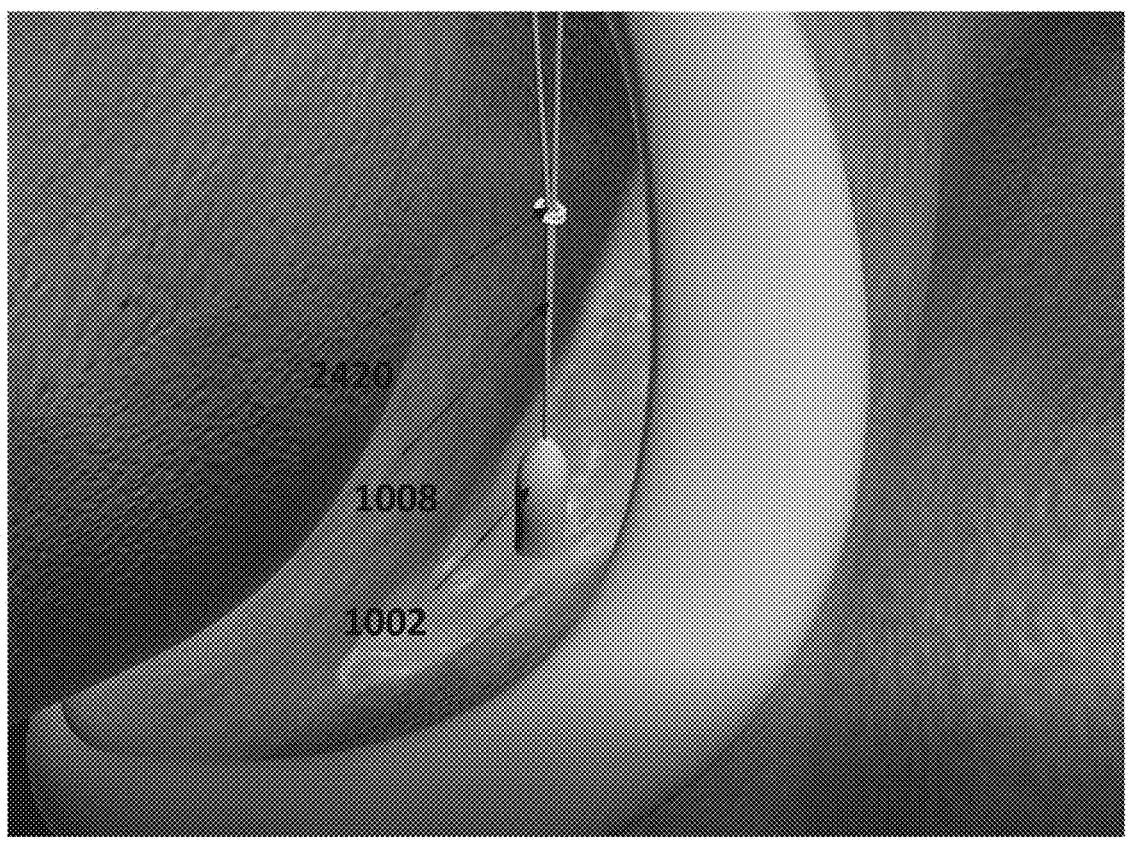
Figure 25H:
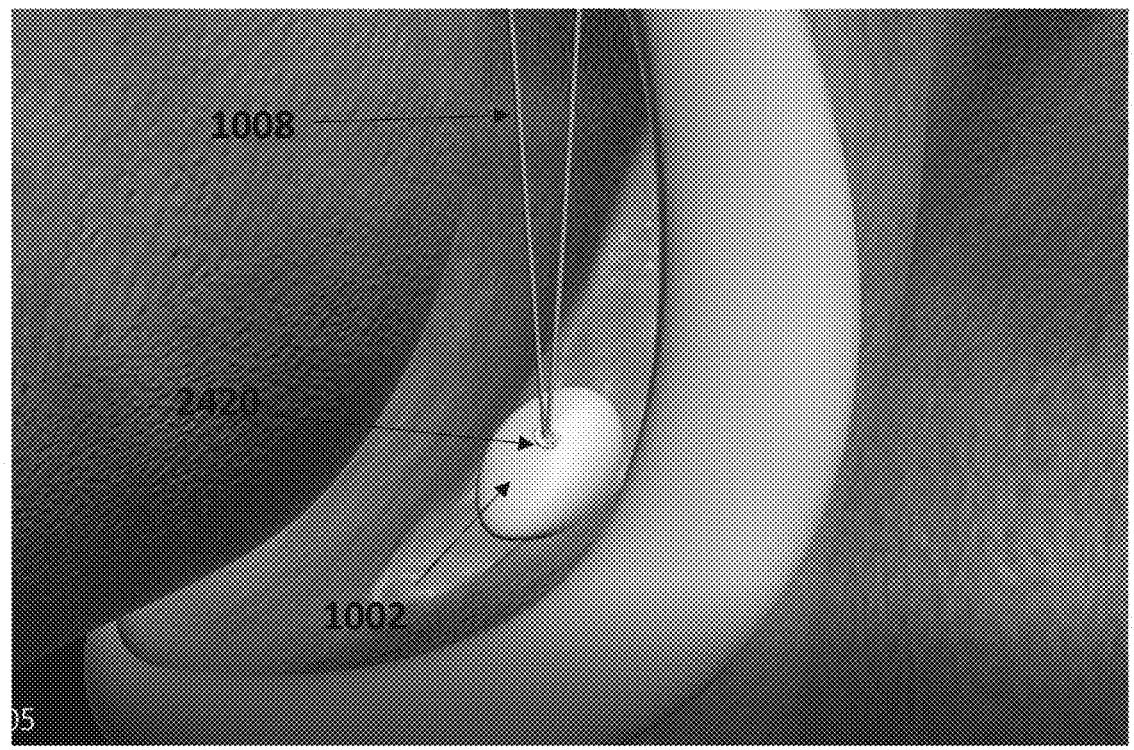
Figure 25I:
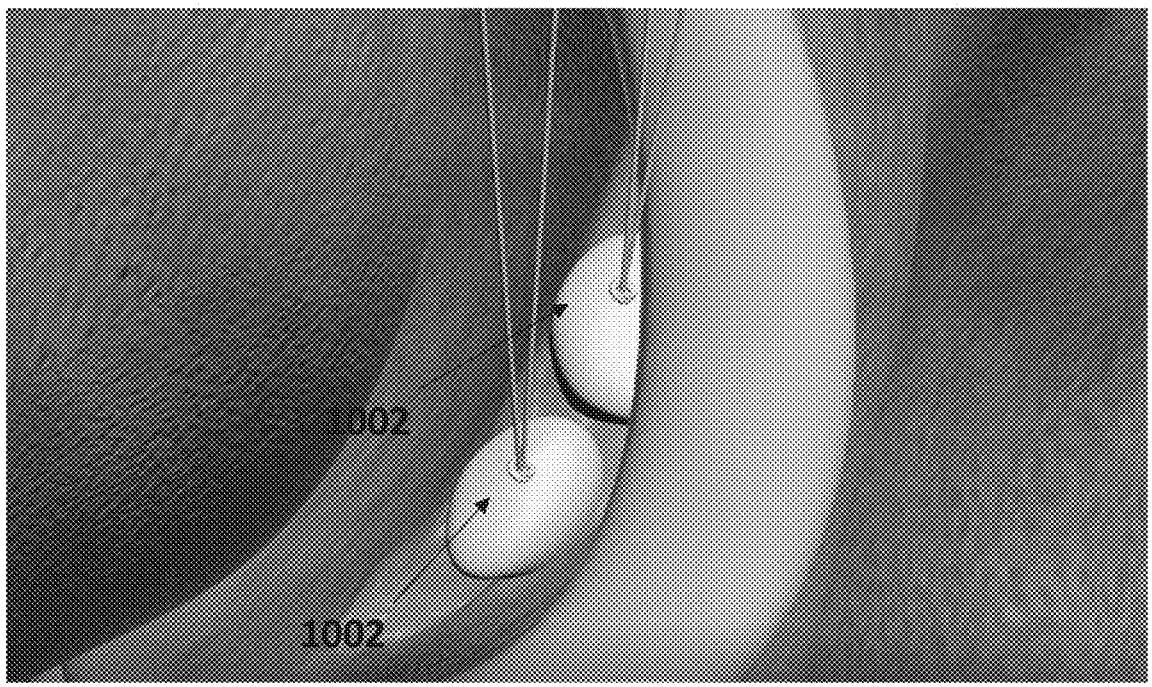
Figure 25J:
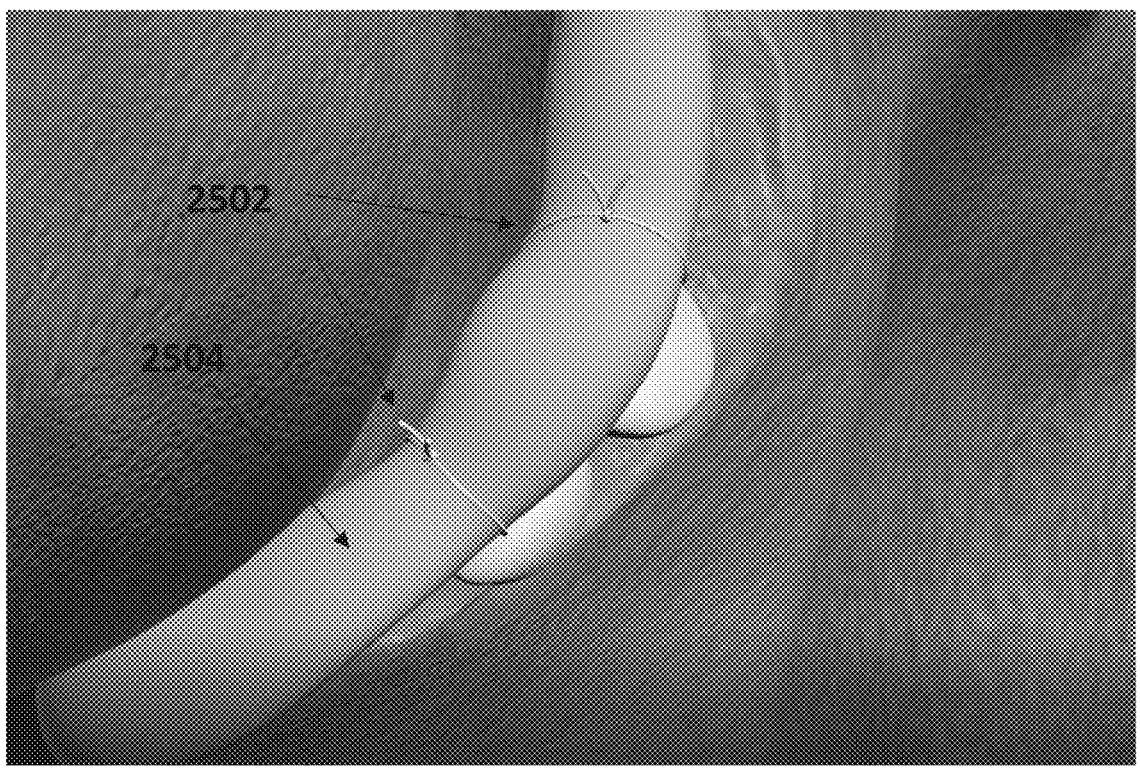
Figure 25K:
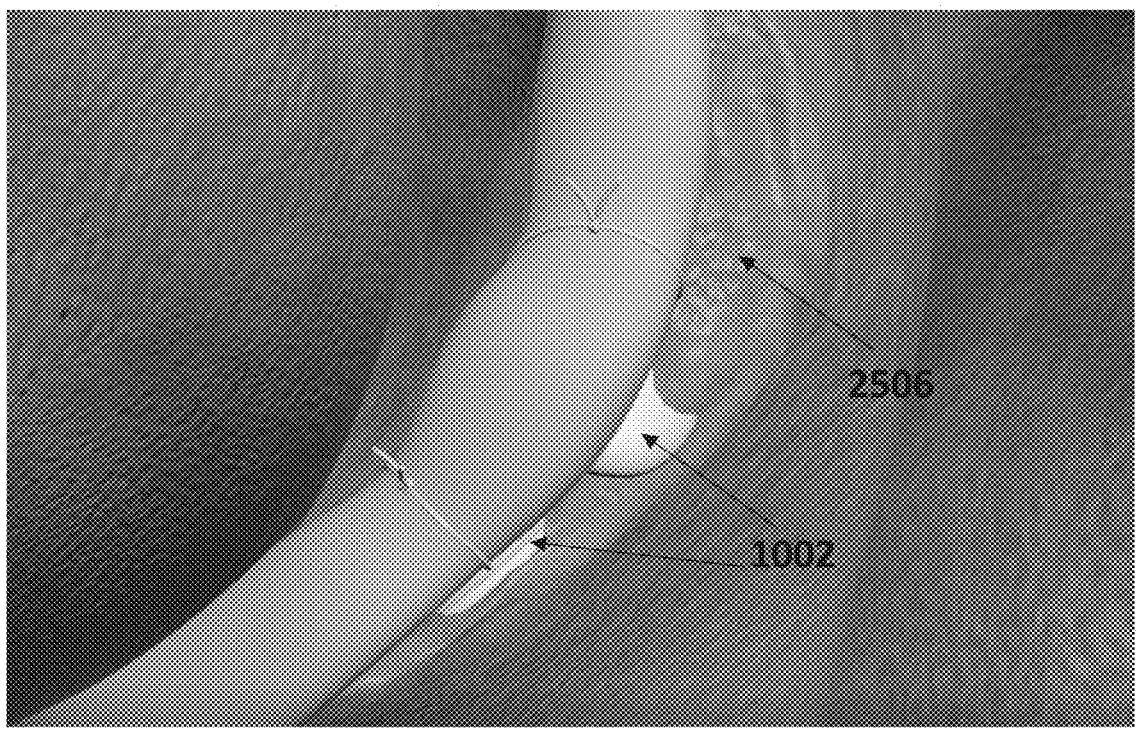
Figure 25L:
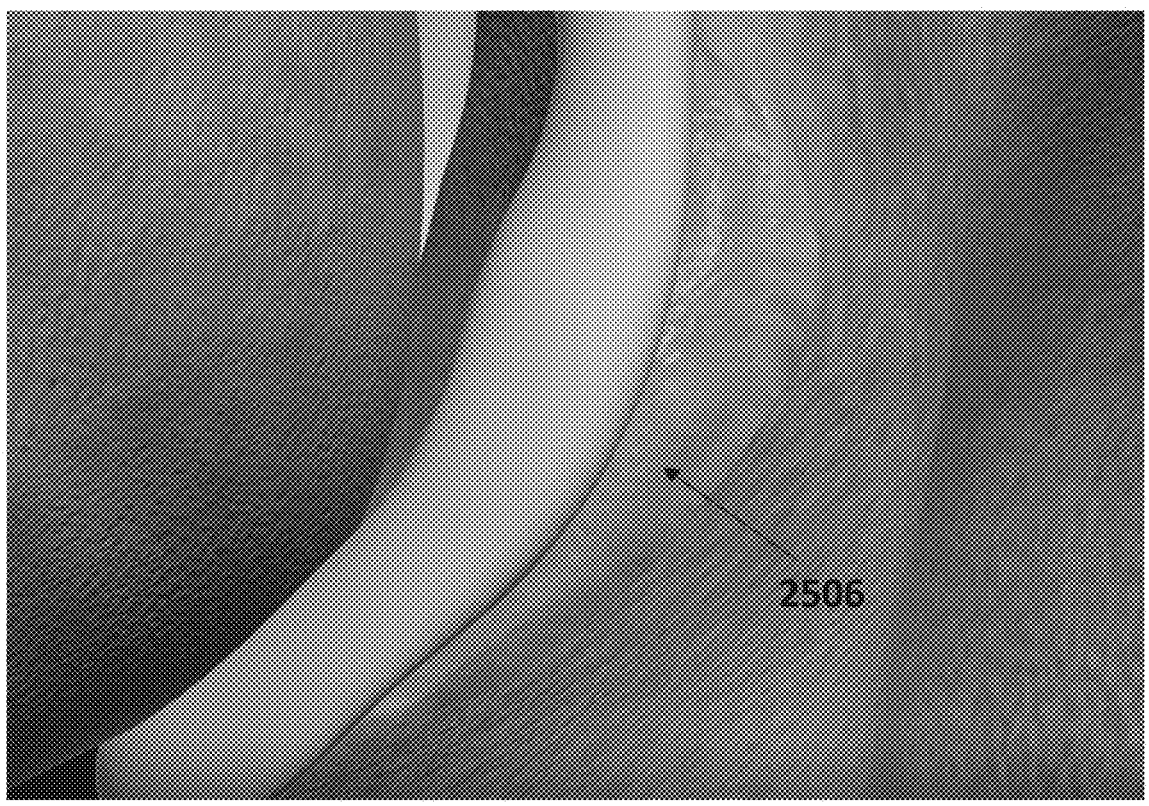

9. In some embodiments, after a while, the organic material in the container 1002 will induce the filling of the lesion 2506, as schematically shown in FIGS. 25k and 25l.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for treating a lesion in a joint with a bone-implant; said bone implant comprising:
    a bone anchor sized and configured to be inserted in a bore of a bone, within or adjacent to said lesion and further configured to keep said bone-implant in place on said bone,
    a container sized and configured to be disposed within said lesion and outside of said bore,
    an osteoconductive bone-filler material inside said container, and
    one or more sutures fixed to and extending proximally from said bone anchor, the method comprising:
    a. implanting said bone anchor of said bone-implant in said bore;
    b. transitioning at least a portion of said container from an elongate, low-profile delivery configuration to a shortened radially-expanded deployment configuration such that said container at least partially fills said lesion, and said bone-filler material located in said container causes said bone-implant to osseointegrate with said bone,
    wherein said one or more sutures passes through one or more holes defined in said container,
    wherein said implanting comprises distal sliding of said container along said one or more sutures toward said bone anchor.

2. The method according to claim 1, wherein said transitioning comprises tying down said one or more sutures.

3. The method according to claim 2, wherein said tying down comprises compressing said container against said bone.

4. The method according to claim 1, further comprising, after said transitioning, knotting together two or more longitudinal sutures portions of said one or more sutures.

5. The method according to claim 1, further comprising, before implanting said bone anchor, drilling a hole in said bone to generate said bore in said bone.

6. The method according to claim 5, wherein implanting said bone anchor, comprises implanting said bone anchor, in said lesion while said container is disposed outside said bore.

7. The method according to claim 5, wherein said drilling is performed within or adjacent to said lesion.

8. The method according to claim 5, wherein said implanting comprises implanting said bone anchor, of said bone-implant in said bore while disposing said container with bone-void filler material partially within said bore and partially outside of said bore.

9. The method according to claim 1, wherein said lesion is a Hill-Sachs lesion on a humeral head.

10. The method according to claim 1, wherein said lesion is a Bankart lesion characterized by detachment of a labrum from a glenoid rim, and said method further comprises passing through a distal glenoid-facing surface of the elongate labrum said one or more sutures.

11. The method according to claim 10, further comprising suturing the detached labrum to a proximal portion of said bone-implant using said one or more sutures.

12. The method according to claim 1, wherein said implanting comprises implanting more than one bone-implant.

13. The method according to claim 1, wherein said implanting comprises implanting more than one of said bone anchor.

14. The method according to claim 1, the method further comprising providing said container made of a biodegradable material.

* * * * *